US008324257B2

(12) United States Patent
Ahrendt et al.

(10) Patent No.: US 8,324,257 B2
(45) Date of Patent: Dec. 4, 2012

(54) MITOTIC KINESIN INHIBITORS AND METHODS OF USE THEREOF

(75) Inventors: Kateri Ahrendt, Boulder, CO (US); Robert Kirk Delisle, Longmont, CO (US); Jeremy Hans, Boulder, CO (US); Joseph P. Lyssikatos, Piedmont, CA (US); John E. Robinson, Commerce City, CO (US); Eli M. Wallace, Lyons, CO (US); Qian Zhao, Superior, CO (US)

(73) Assignee: Array Biopharma Inc., Boulder, CO (US)

( * ) Notice: Subject to any disclaimer, the term of this patent is extended or adjusted under 35 U.S.C. 154(b) by 617 days.

(21) Appl. No.: 12/444,221

(22) PCT Filed: Oct. 3, 2007

(86) PCT No.: PCT/US2007/080246
§ 371 (c)(1),
(2), (4) Date: Apr. 3, 2009

(87) PCT Pub. No.: WO2008/042928
PCT Pub. Date: Apr. 10, 2008

(65) Prior Publication Data
US 2010/0041719 A1    Feb. 18, 2010

Related U.S. Application Data

(60) Provisional application No. 60/848,915, filed on Oct. 3, 2006.

(51) Int. Cl.
*A01N 43/82* (2006.01)
*A61K 31/41* (2006.01)
*C07D 285/08* (2006.01)
(52) U.S. Cl. .......................... 514/363; 514/364; 548/128
(58) Field of Classification Search .................. 514/363, 514/364; 548/128
See application file for complete search history.

(56) References Cited

U.S. PATENT DOCUMENTS

| 2,702,803 | A  | 2/1955  | Ainsworth      |
|-----------|----|---------|----------------|
| 4,782,072 | A  | 11/1988 | Stillings      |
| 4,927,822 | A  | 5/1990  | Brown et al.   |
| 5,668,159 | A  | 9/1997  | Jin et al.     |
| 5,958,957 | A  | 9/1999  | Andersen et al.|
| 5,972,937 | A  | 10/1999 | Gaster et al.  |
| 5,972,978 | A  | 10/1999 | Andersen et al.|
| 6,159,938 | A  | 12/2000 | Gyorkos et al. |
| 6,235,762 | B1 | 5/2001  | Takasugi et al.|
| 7,115,642 | B2 | 10/2006 | Singh et al.   |
| 7,220,745 | B2 | 5/2007  | Singh et al.   |
| 7,326,790 | B2 | 2/2008  | Singh et al.   |
| 7,425,636 | B2 | 9/2008  | Murakata et al.|
| 7,449,486 | B2 | 11/2008 | Hans et al.    |
| 2002/0002193 | A1 | 1/2002 | Yu et al.      |
| 2003/0229054 | A1 | 12/2003 | Belliotti et al. |
| 2004/0167188 | A1 | 8/2004 | Xin et al.     |
| 2004/0248950 | A1 | 12/2004 | Ishizuka et al. |
| 2005/0004186 | A1 | 1/2005 | Barrett et al. |
| 2005/0009877 | A1 | 1/2005 | Lu             |
| 2005/0070538 | A1 | 3/2005 | Cheng et al.   |
| 2005/0075375 | A1 | 4/2005 | Vourloumis et al. |
| 2005/0119484 | A1 | 6/2005 | Breslin et al. |
| 2007/0112044 | A1 | 5/2007 | Murakata et al. |
| 2007/0155804 | A1 | 7/2007 | Murakata et al. |
| 2007/0276017 | A1 | 11/2007 | Murakata et al. |
| 2008/0153887 | A1 | 6/2008 | Cox et al.     |

FOREIGN PATENT DOCUMENTS

| EP | 0531906 A1 | 3/1993 |
| EP | 1004241 A1 | 5/2000 |
| JP | 2005-232016 | 9/2005 |
| WO | 98/38177 A1 | 9/1998 |
| WO | 01/56994 A1 | 8/2001 |
| WO | 2004/111023 A1 | 12/2004 |
| WO | 2005/092304 A2 | 10/2005 |

OTHER PUBLICATIONS

International Search Report for Co-Pending PCT Application Serial No. PCT/US2007/08246.
Bryn et al., "Chapter 11: Hydrates and Solvates" Solid-State Chemistry of Drugs, Second Edition, 1999, pp. 233-247.
Lala et al., "Role of Nitric Oxide in Tumor Progression: Lessons from Experimental Tumors" Cancer and Metastasis Reviews, 1998, 17(1), pp. 91-106.
Golub et al., "Molecular Classification of Cancer: Class Discovery and Class Prediction by Gene Expression Monitoring", Science, 1999, vol. 286, pp. 537-537.
Askari et al., "Thiadiazoles and Thiadizolines, Part 1, Reaction of Thiourea and Ethylenethiourea with Chlorodiazabutadienes: A New Route to 4-amidino-1,3,4-thiadiazolines"; Database CAPLUS on STN, Chem. Abstr., Accession No. 1981:174996, Journal of the Chemical Society, Perkin Transactions 1: Organic and Bio-Organic Chemistry; 1981; pp. 360-365 abstract; vol. 2.
Coleman et al., "Inhibitors of the Mitotic Kinesin Spindle Protein" Expert Opin. Ther. Patents, (2004) 14(12): 1659-1667.

*Primary Examiner* — Samira Jean-Louis
(74) *Attorney, Agent, or Firm* — John R. Moore, Esq.; Corey M. Williams, Esq.; Viksnins Harris & Padys PLLP

(57) ABSTRACT

This invention relates to inhibitors of mitotic kinesins, particularly KSP, and methods for producing these inhibitors. The invention also provides pharmaceutical compositions comprising the inhibitors of the invention and methods of utilizing the inhibitors and pharmaceutical compositions in the treatment of various disorders.

37 Claims, No Drawings

MITOTIC KINESIN INHIBITORS AND METHODS OF USE THEREOF

PRIORITY OF INVENTION

This application claims priority to U.S. Provisional Application No. 60/848,915 that was filed on 3 Oct. 2006, which is hereby incorporated herein by reference in its entirety.

BACKGROUND OF THE INVENTION

Description of the State of the Art

Among the therapeutic agents used to treat cancer are the taxanes aid vinca alkaloids, which act on microtubules. Microtubules are the primary structural elements of the mitotic spindle, which is responsible for distribution of replicate copies of the genome to each of the two daughter cells that result from cell division. It is presumed that disruption of the mitotic spindle by those drugs results in inhibition of cancer cell division and induction of cancer cell death. However, microtubules form other types of cellular structures, including tracks for intracellular transport in nerve processes. Because drugs such as taxanes and vinca alkaloids do not specifically target mitotic spindles, they have side effects that limit their usefulness.

Improvements in the specificity of agents used to treat cancer is of considerable interest, in part because of the improved therapeutic benefits that would be realized if the side effects associated with administration of these agents could be reduced. Traditionally, dramatic improvements in the treatment of cancer have been associated with identification of therapeutic agents acting through novel mechanisms. Examples include not only the taxanes, but also the camptothecin class of topoisomerase I inhibitors. From both of these perspectives, mitotic kinesins are attractive targets for new anti-cancer agents.

Mitotic kinesins are enzymes essential for assembly and function of the mitotic spindle but are not generally part of other microtubule structures such as nerve processes. Mitotic kinesins play essential roles during all phases of mitosis. These enzymes are "molecular motors" that transform energy released by hydrolysis or ATP into mechanical force that drives the directional movement of cellular cargoes along microtubules. During mitosis, kinesins organize microtubules into the bipolar structure that is the mitotic spindle. Kinesins mediate movement of chromosomes along spindle microtubules, as well as structural changes in the mitotic spindle associated with specific phases of mitosis. Experimental perturbation of mitotic kinesin function causes malformation or dysfunction of the mitotic spindle, frequently resulting in coil cycle arrest and cell death.

Among the identified mitotic kinesins is kinesin spindle protein ("KSP"). KSP belongs to an evolutionarily conserved kinesin subfamily of plus end-directed microtubule motors that assemble into bipolar homotetramers consisting of antiparallel homodimers. During mitosis, KSP associates with microtubules of the mitotic spindle. Microinjection of antibodies directed against KSP into human cells prevents spindle pole separation during prometaphase, giving rise to monopolar spindles and causing mitotic arrest and induction of programmed cell death. KSP and related kinesins in other non-human organisms bundle antiparallel microtubules and slide them relative to one another, thus forcing the spindle poles apart. KSP may also mediate in anaphase B spindle elongation and focusing of microtubules at the spindle pole.

Mitotic kinesins are therefore attractive targets for the discovery and development of novel mitotic chemotherapeutics.

Compounds that inhibit mitotic kinesins are known, for example, International Patent Applications WO 2004/111024, WO 2005/035512. WO 2006/031348, WO 2006/044825, and WO 2006/119146.

Thiadiazoles are known, for example, WO 2004/111023, WO 2005/061707, WO 2006/101102, WO 2006/101103, WO 2006/101104, WO2006/101105, and U.S. Pat. No. 6,235,762.

SUMMARY OF THE INVENTION

The invention provides compounds that inhibit mitotic kinesins, in particular the mitotic kinesin KSP. The compounds are useful as therapeutic agents, for example, for inhibiting the assembly or function of microtubule structures, including the mitotic spindle.

In one embodiment, the invention provides a compound of the invention that is a compound of Formula I:

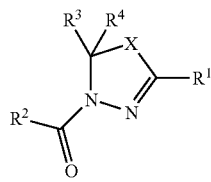

I or a salt thereof, wherein $R^1$-$R^4$ and X have any of the values defined herein.

In another embodiment, the invention provides a composition comprising a compound of the invention and a pharmaceutically acceptable carrier.

In another embodiment, the invention provides a method for inhibiting the proliferation of cells, comprising contacting said cells with an effective amount of a compound of the invention.

In another embodiment, the invention provides a method for inhibiting the proliferation of cells in an animal, comprising administering an effective amount of a compound of the invention to the animal.

In another embodiment, the invention provides a method for inhibiting abnormal cell growth, comprising contacting the abnormal cells with an effective amount of a compound of the invention.

In another embodiment, the invention provides a method for inhibiting abnormal cell growth in an animal, comprising administering an effective amount of a compound of the invention to the animal.

In another embodiment, the invention provides a method for inhibiting one or more kinesins, comprising contacting the one or more kinesins with an effective amount of a compound of the invention.

In another embodiment, the invention provides a method for inhibiting one or more kinesins in an animal, comprising administering an effective amount of a compound of the invention to the animal.

In another embodiment, the invention provides a method for treating a microtubule-mediated condition in an animal, comprising administering an effective amount of a compound of die invention to the animal.

In another embodiment, the invention provides a method for inhibiting mitotic spindle formation in an animal, comprising administering an effective amount of a compound of the invention to the animal.

In another embodiment, the invention provides a method of treating a fungal or other eukaryote infection in an animal, comprising administering an effective amount of a compound of the invention to the animal.

In another embodiment, the invention provides a kit for treating an abnormal cell growth condition, wherein said kit comprises:

a) a compound of the invention; and
b) instructions for use.

In another embodiment, the invention provides a compound of the invention for use in therapy.

In another embodiment, the invention provides the use of a compound of the invention in the manufacture of a medicament for inhibiting the proliferation of cells in an animal.

In another embodiment, the invention provides the use of a compound of the invention in the manufacture of a medicament for inhibiting abnormal cell growth in an animal.

In another embodiment, the invention provides the use of a compound of the invention in the manufacture of a medicament for inhibiting one or more kinesins in an animal.

In another embodiment, the invention provides the use of a compound of the invention in the manufacture of a medicament for treating a microtuble-mediated condition in an animal.

In another embodiment, the invention provides the use of a compound of the invention in the manufacture of a medicament for inhibiting mitotic spindle formation in all animal.

In another embodiment, the invention provides the use of a compound of the invention in the manufacture of a medicament for treating a fungal or other eukaryote infection in an animal.

Additional advantages, other embodiments, and novel features of this invention are set forth in part in the description that follows.

DETAILED DESCRIPTION OF THE INVENTION

Definitions

The term "alkyl" as used herein refers to a saturated linear or branched-chain monovalent hydrocarbon radical having one to ten carbon atoms, wherein the alkyl radical may be optionally substituted with one or more substituents. Examples of alkyl groups include, but are not limited to, methyl, ethyl, n-propyl, isopropyl, butyl, isobutyl, sec-butyl, tert-butyl, pentyl, isopentyl, neopentyl, tert-pentyl, hexyl, 2-hexyl, 3-hexyl, 3-methoxypentyl, heptyl, octyl and the like.

The term "alkylene" as used herein refers to a linear or branched saturated divalent hydrocarbon radical of one to ten carbon atoms, wherein the alkylene radical may be optionally substituted with one or more substituents. Examples of alkylene groups include, but are not limited to, methylene, ethylene, propylene, 2-methylpropylene, pentylene and the like.

The term "alkenyl" refers to a linear or branched-chain monovalent hydrocarbon radical having two to ten carbon atoms and at least one double bond, and includes, but is not limited to, ethenyl, propenyl, 1-but-3-enyl, 1-pent-3-enyl, 1-hex-5-enyl and the like, wherein the alkenyl radical may be optionally substituted with one or more substituents. The term includes radicals having "cis" and "trans" orientations, or alternatively, "E" and "Z" orientations.

The term "alkenylene" refers to a linear or branched divalent hydrocarbon radical of two to ten carbons containing at least one double bond, wherein the alkenylene radical may be optionally substituted with one or more substituents. Examples include, but are not limited to, ethenylene, propenylene and the like.

The term "alkynyl" refers to a linear or branched monovalent hydrocarbon radical of two to ten carbon atoms containing at least one triple bond. Examples include, but are not limited to, ethynyl, propynyl, butynyl, pentyn-2-yl and the like, wherein the alkynyl radical may be optionally substituted with one or more substituents.

The term "alkynylene" refers to a linear or branched divalent hydrocarbon radical of two to ten carbons containing at least one triple bond, wherein the alkynylene radical may be optionally substituted with one or more substituents.

The term "animal" includes birds and mammals (e.g. domestic mammals and humans).

The term "cycloalkyl" refers to a saturated or partially unsaturated monocyclic monovalent hydrocarbon radical having front three to ten carbon atoms, as well as to a polycyclic (e.g., bicyclic or tricyclic) monovalent hydrocarbon radical, such as a saturated or partially unsaturated monocyclic hydrocarbon radical fused to one or more other saturated or partially unsaturated monocyclic radicals. Examples of cycloalkyl groups include, but are not limited to, cyclopropyl, cyclobutyl, cyclopentyl, cyclohexyl, cycloheptyl and the like. The cycloalkyl may be optionally substituted at one or more substitutable positions with one or more substituents. Bicyclic cycloalkyls include those having 7 to 12 ring atoms arranged, for example, as a bicyclo[4,5], [5,5], [5,6] or [6,6] system, or as bridged systems such as bicyclo[2.2.1]heptane, bicyclo[2.2.2]octane, aid bicyclo[3.2.2]nonane.

The term "heterocycle" refers to a 3 to 8 membered saturated or partially unsaturated monocyclic ring comprising one or more heteroatoms selected from $N(R^x)$, O, or S; or an ortho-fused bicyclic ring of about eight to twelve ring atoms derived therefrom, particularly a benz-derivative or one derived by fusing a propylene, trimethylene, or tetramethylene diradical thereto; wherein each $R^x$ is independently absent or is H, O, $(C_1-C_4)$alkyl, —C(=O)$(C_1-C_4)$alkyl, phenyl or benzyl. Examples of heterocycles include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, and imidazolidinyl.

The term "heteroaryl" refers to a monocyclic aromatic ring containing five or six ring atoms consisting of carbon and one to four heteroatoms each selected from the group consisting of non-peroxide oxygen, sulfur, and $N(R^x)$, or an ortho-fused bicyclic heterocycle of about eight to ten ring atoms derived therefrom, particularly a benz-derivative or one derived by fusing a propylene, trimethylene, or tetramethylene diradical thereto; wherein each $R^x$ is independently absent or is H, O, $(C_1-C_4)$alkyl, —C(=O)$(C_1-C_4)$alkyl, phenyl or benzyl. Examples of heteroaryl groups include, but are not limited to, pyridinyl, imidazolyl, pyrimidinyl, pyrazolyl, triazolyl, pyrazinyl, tetrazolyl, furyl, thienyl, isoxazolyl, thiazoyl, oxazoyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl.

The term "aryl" refers to a phenyl ring or an ortho-fused bicyclic carbocycle having about nine to ten ring atoms wherein at least one ring is aromatic, particularly a benz-derivative or one derived by fusing a propylene, trimethylene, or tetramethylene diradical thereto. Examples of aryl include phenyl, naphthyl, dihydronaphthyl, and tetrahydronaphthyl.

The term "halo" refers to fluoro, bromo, chloro, or iodo.

The term "microtuble-mediated condition" includes, but is not limited to, cellular proliferative diseases, for example cancer, hyperplasias, restenosis, cardiac hypertrophy, immune disorders, infectious disease, fungal or other eukaryote infections, and inflammatory disease.

The term "abnormal cell growth" refers to cell growth that is independent of normal regulatory mechanisms (e.g., loss of contact inhibition). This includes, but is not limited to the abnormal growth of: (1) tumor cells (tumors) that proliferate by expressing a mutated tyrosine kinase or overexpression of a receptor tyrosine kinase; (2) benign and malignant cells of other proliferative diseases in which aberrant tyrosine kinase activation occurs; (3) any tumors that proliferate by receptor tyrosine kinases; (4) any tumors that proliferate by aberrant serine/threonine kinase activation; and (5) benign and malignant cells of other proliferative diseases in which aberrant serine/threonine kinase activation occurs.

The term "treating," includes reversing, alleviating, inhibiting the progress of, or preventing the disorder or condition to which such term applies, or one or more symptoms of such disorder or condition. The term "treatment," as used herein, unless otherwise indicated, refers to the act of "treating" as defined immediately above.

Compounds of the Invention

In general, the invention relates to compounds of Formula I:

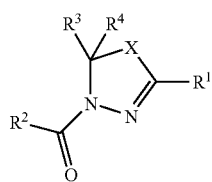

and to salts thereof, wherein:

X is O or S;

$R^1$ and $R^3$ are each independently aryl or heteroaryl, wherein said aryl and heteroaryl are each optionally substituted with one or more groups independently selected from halo, cyano, nitro, fluoromethyl, difluoromethyl, trifluoromethyl, difluoromethoxy, trifluoromethoxy, azido, —$OR^a$, $NR^aR^b$, —C(=O)$R^a$, —C(=O)$OR^a$, —$NR^aC$(=O)$OR^d$, —C(=O)$NR^aR^b$, ($C_1$-$C_{10}$)alkyl, (C3-$C_{10}$)cycloalkyl, ($C_2$-$C_{10}$)alkenyl, and ($C_2$-$C_{10}$)alkynyl;

$R^2$ is ($C_1$-$C_{10}$)alkyl, ($C_2$-$C_{10}$)alkenyl, ($C_2$-$C_{10}$)alkynyl, ($C_3$-$C_{10}$)cycloalkyl, $NR^jR^k$, aryl heterocycle, or heteroaryl, wherein each ($C_1$-$C_{10}$)alkyl, ($C_2$-$C_{10}$)alkenyl, ($C_2$-$C_{10}$)alkynyl, ($C_3$-$C_{10}$)cycloalkyl, C(=$NR^h$)$R^i$, aryl, and heteroaryl of $R^2$ is optionally substituted with one or more $R^o$;

$R^4$ is Z—$NR^g$—C(=$NR^h$)$R^i$, Z—$NR^g$—C(=$NR^h$)$NR^j$ $R^k$, Z—C(=$NR^h$)$NR^jR^k$, Z—O—$NR^g$C(=$NR^h$)$NR^jR^k$, Z—O—$NR^g$—C(=$NR^h$)$R^i$, Z—$NR^m$—$NR^n$—C(=$NR^h$) $R^i$, Z—O—$NR^jR^k$, Z—O—Z—C(=$NR^h$)$NR^jR^k$, Z—O—N=C($R^r$)$_2$, Z—$NR^g$—C(=$CHR^q$)$NR^jR^k$, or Z—$NR^m$— $NR^n$—C(=$NR^h$)$NR^jR^k$, provided that when $R^4$ is Z—O— $NR^gC$(=$NR^h$)$NR^jR^k$, Z—O—$NR^g$—C(=$NR^h$)$R^i$, or Z—O—$NR^jR^k$, then $R^j$ and $R^g$ are not $OR^p$;

Z is ($C_1$-$C_{10}$)alkylene, ($C_2$-$C_{10}$)alkenylene, or ($C_2$-$C_{10}$)alkynylene, each optionally substituted with one or more halo;

$R^a$, $R^b$, and $R^c$ are each independently selected from H, ($C_1$-$C_{10}$)alkyl, ($C_2$-$C_{10}$)alkenyl, ($C_2$-$C_{10}$)alkynyl, ($C_3$-$C_{10}$) cycloalkyl, aryl, heteroaryl, heterocycle and aryl($C_1$-$C_3$) alkyl, wherein each $R^a$ mid $R^b$ is optionally substituted with one or more groups independently selected from oxo (with the proviso that it is not on an aromatic ring), halo, cyano, nitro, —$OR^e$, —$NR^eR^f$, difluoromethyl, trifluoromethyl, difluoromethoxy, trifluoromethoxy, azido, ($C_1$-$C_{10}$)alkyl, and ($C_3$-$C_{10}$)cycloalkyl; or any $NR^aR^b$ taken together form a heterocycle, wherein said heterocycle is optionally substituted with one or more groups independently selected from oxo (with the proviso that it is not on an aromatic ring), halo, cyano, nitro, $OR^e$, —$NR^eR^f$, difluoromethyl, trifluoromethyl, difluoromethoxy, trifluoromethoxy, azido, ($C_1$-$C_{10}$)alkyl, and ($C_3$-$C_{10}$)cycloalkyl; or any $NR^bR^c$ taken together form a heterocyclic ring, wherein said heterocycle ring is optionally substituted with one or more oxo (with the proviso that it is not on an aromatic ring), halo, cyano, nitro, $OR^e$, —$NR^eR^f$, difluoromethyl, trifluoromethyl, difluoromethoxy, trifluoromethoxy, azido, ($C_1$-$C_{10}$)alkyl, and ($C_3$-$C_{10}$)cycloalkyl; or $R^a$ and $R^d$ together with the atoms to which they are attached form a heterocycle; or $R^a$ and $R^g$ together with the atoms to which they are attached form a heterocycle;

$R^d$ is ($C_1$-$C_{10}$)alkyl, ($C_2$-$C_{10}$)alkenyl, ($C_3$-$C_{10}$)cycloalkyl, aryl, heteroaryl, heterocycle or aryl($C_1$-$C_3$)alkyl, wherein each $R^d$ is optionally substituted with one or more groups independently selected from oxo (with the proviso that it is not on an aromatic ring), halo, cyano, nitro, $OR^e$, —$NR^eR^f$, difluoromethyl, trifluoromethyl, difluoromethoxy, trifluoromethoxy, azido, ($C_1$-$C_{10}$)alkyl, and ($C_3$-$C_{10}$)cycloalkyl; or $R^a$ and $R^d$ together with the atoms to which they are attached form a heterocycle;

$R^e$ and $R^f$ are independently selected from H, ($C_1$-$C_{10}$) alkyl, ($C_2$-$C_{10}$)alkenyl, ($C_2$-$C_{10}$)alkynyl, and ($C_3$-$C_{10}$)cycloalkyl; or $NR^eR^f$ taken together form a heterocycle.

$R^g$, $R^m$ and $R^n$ are independently H, $OR^p$, or ($C_1$-$C_{10}$)alkyl, or $R^i$ and $R^m$ together with the atoms to which they are attached form a heterocycle; or $R^g$ and $R^j$ together within the atoms to which they are attached form a heterocycle; or $R^a$ and $R^g$ together with the atoms to which they are attached form a heterocycle; or $R^i$ amid $R^n$ together with the atoms to which the) are attached form a heterocycle; or $R^m$ and $R^n$ together with the atoms to which they are attached form a heterocycle; or $R^j$ and $R^m$ together with the atoms to which they are attached form a heterocycle; or $R^j$ and $R^n$ together with the atoms to which they are attached form a heterocycle;

$R^h$ is H, —$OR^p$, cyano, —C(=O)N($R^p$)$_2$, —C(=O)$R^p$, or alkyl optionally substituted with one or more groups independently selected from halo, cyano, —$OR^p$, —N($R^p$)$_2$, and aryl; or $R^h$ and $R^j$ together with the atoms to which they are attached form a heterocycle; or $R^h$ and $R^i$ together with the atoms to which they are attached form a heterocycle;

$R^i$ is H or ($C_1$-$C_{10}$)alkyl optionally, substituted with one or more groups independently selected from halo, nitro, cyano, —$OR^p$, —N($R^p$), and aryl; or $R^i$ and $R^m$ together with the atoms to which they are attached form a heterocycle; or $R^h$ and $R^i$ together with the atoms to which they are attached form a heterocycle; or $R^i$ and $R^n$ together with the atoms to which they are attached form a heterocycle;

$R^j$ and $R^k$ are independently H, —$OR^p$, C(=O)$R^p$, heterocycle, aryl, heteroaryl, ($C_3$-$C_6$)cycloalkyl or ($C_1$-$C_{10}$)alkyl optionally substituted with one or more groups independently selected from halo, cyano, —$OR^p$, —N($R^p$)$_2$, and aryl; or —$NR^jR^k$ together form a heterocycle; or $R^g$ and $R^j$ together with the atoms to which they are attached form a heterocycle; or $R^h$ and $R^j$ together with the atoms to which they, are attached form a heterocycle; or $R^j$ and $R^k$ together with the atoms to which they are attached form a heterocycle; or $R^j$ and $R^m$ together with the atoms to which they are attached form a heterocycle; or $R^j$ and $R^n$ together with the atoms to which they are attached form a heterocycle;

each $R^o$ is independently oxo (provided it is not on a nitrogen, oxygen or an unsaturated carbon), halo, cyano, nitro, azido, —$NR^aR^h$, —C(=O)$R^a$, —C(O)O$R^a$, —OC(=O)$R^a$, —$NR^aC$(=O)O$R^d$, —C(=O)$NR^aR^b$, —$NR^aC$(=O)$NR^b$(O$R^c$), —$NR^aC$(=O)$NR^bR^c$, —$NR^aC$(NCN)$NR^bR^c$, —O$R^a$, ($C_1$-$C_{10}$)alkyl, ($C_3$-$C_{10}$)cycloalkyl, ($C_2$-$C_{10}$)alkenyl, ($C_2$-$C_{10}$)alkyl, aryl, heteroaryl, aryl($C_1$-$C_3$)alkyl, heteroaryl($C_1$-$C_3$)alkyl, heterocycle, heterocycle($C_1$-$C_3$)alkyl, or —OP(=O)(O$R^a$)$_2$, wherein said ($C_1$-$C_{10}$)alkyl, ($C_3$-$C_{10}$)cycloalkyl, ($C_2$-$C_{10}$)alkenyl, ($C_2$-$C_{10}$)alkynyl, aryl, heteroaryl, aryl($C_1$-$C_3$)alkyl, heteroaryl($C_1$-$C_3$)alkyl, heterocycle and heterocycle($C_1$-$C_3$)alkyl are optionally substituted with one or more groups independently selected from oxo (with the proviso that it is not on an aromatic ring), halo, cyano, nitro, hydroxy —O$R^a$, $NR^aR^b$, difluoromethyl, trifluoromethyl, difluoromethoxy, trifluoromethoxy, azido, —C(=O)$R^a$, —C(=O)O$R^n$, —OC(=O)$R^a$, —$NR^aC$(=O)O$R^b$, —C(=O)$NR^aR^b$, —$NR^aC$(=O)$NR^bR^c$, and —$NR^aC$(NCN)$NR^bR^c$;

each $R^p$ is independently H, ($C_1$-$C_{10}$)alkyl, —P(=O)(OH)$_2$, acetyl, 2-aminopropanoyl, aminoacetyl, or methoxycarbonyl;

each $R^q$ is independently ($C_1$-$C_{10}$)alkyl, ($C_2$-$C_{10}$)alkenyl, ($C_2$-$C_{10}$)alkynyl, ($C_3$-$C_{10}$)cycloalkyl, halo, cyano, nitro, —$NR^aR^b$, —C(=O)$R^p$, or O$R^p$; and each $R^r$ is independently ($C_1$-$C_{10}$)alkyl, ($C_2$-$C_{10}$)alkenyl, ($C_2$-$C_{10}$)alkynyl, ($C_3$-$C_{10}$)cycloalkyl, aryl, or aryl($C_1$-$C_3$)alkyl; or —C($R^r$)$_2$ together form a ($C_3$-$C_{10}$)cycloalkyl.

Compounds of Formula I include compounds wherein $R^1$ and $R^3$ are each independently aryl or heteroaryl, wherein said aryl and heteroaryl are each optionally substituted with one or more groups independently selected from halo, cyano, nitro, difluoromethyl, trifluoromethyl, difluoromethoxy, trifluoromethoxy, azido, —O$R^a$, —$NR^aR^b$, —C(=O)$R^a$, —C(=O)O$R^a$, —$NR^aC$(=O)O$R^d$, —C(=O)$NR^aR^b$, ($C_1$-$C_{10}$)alkyl, (C3-$C_{10}$)cycloalkyl, ($C_2$-$C_{10}$)alkenyl, and ($C_2$-$C_{10}$)alkynyl.

Certain compounds of the invention can exist as two or more tautomeric forms. A "tautomer" is one of two or more structural isomers that exist in equilibrium and are readily converted from one isomeric form to another, such as structures formed by the movement of a hydrogen from one site to another within the same molecule. Other tautomeric forms of the compounds man interchange, for example, via enolization/de-enolization and the like. Accordingly, the present invention includes all tautomeric forms of compounds of Formula I.

The compounds of the invention may also possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers, diastereomers mixtures, racemic or otherwise, thereof. Accordingly, this invention also includes all such isomers, including diastereomeric mixtures and pure enanatiomers of the compounds. Diastereomeric mixtures can be separated into their individual diastereomers on the basis of their physical chemical differences by methods known to those skilled in the art, for example, by chromatography or fractional crystallization. Enantiomer mixtures be separated by any suitable method, e.g. by converting the enantiomers into a diastereomeric mixture by reaction with an appropriate optically active compound (e.g., alcohol), separating the diastereomers, and converting (e.g., hydrolyzing) the individual diastereomers to the corresponding pure enantiomers. The methods for the determination of stereochemistry and the separation of stereoisomers are well known in the art (see discussion in Chapter 4 of "Advanced Organic Chemistry", 4th edition, J. March, John Wiley and Sons, New York, 1992).

In one embodiment of the invention, X is S.

In one embodiment of the invention, $R^1$ is aryl that is optionally substituted with one or more groups independently selected from halo, cyano, difluoromethyl, trifluoromethyl, difluoromethoxy, trifluoromethoxy, —O$R^a$, —$NR^aR^b$, —C(=O)$R^a$, —C(=O)O$R^a$, —$NR^aC$(=O)O$R^d$, —C(=O)$NR^aR^b$, ($C_1$-$C_{10}$)alkyl, ($C_3$-$C_{10}$)cycloalkyl, ($C_2$-$C_{10}$)alkenyl, and ($C_2$-$C_{10}$)alkynyl.

In one embodiment of the invention, $R^1$ is phenyl that is optionally substituted with one or more groups independently selected from halo, cyano, difluoromethyl, trifluoromethyl, difluoromethoxy, trifluoromethoxy, —O$R^a$, —$NR^aR^b$, —C(=O)$R^a$, —C(=O)O$R^a$, —$NR^aC$(=O)O$R^d$, —C(=O)$NR^aR^b$, ($C_1$-$C_{10}$)alkyl, ($C_3$-$C_{10}$)cycloalkyl, ($C_2$-$C_{10}$)alkenyl, and ($C_2$-$C_{10}$)alkynyl.

In one embodiment of the invention, $R^1$ is phenyl that is optionally substituted with one or more groups independently selected from halo, cyano, difluoromethyl, trifluoromethyl, difluoromethoxy, trifluoromethoxy, —O$R^a$, —$NR^aR^b$, —C(=O)$R^a$, —C(=O)O$R^a$, and ($C_1$-$C_{10}$)alkyl.

In one embodiment of the invention, $R^1$ is phenyl that is optionally substituted with one or more halo.

In one embodiment of the invention, $R^1$ is 2,5-difluorophenyl.

In one embodiment of the invention, $R^2$ is ($C_1$-$C_{10}$)alkyl, optionally substituted with one or more $R^o$.

In one embodiment of the invention, each $R^o$ is independently oxo, —$NR^aR^b$, —O$R^a$, ($C_3$-$C_{10}$)cycloalkyl, aryl, or —OP(=O)(O$R^a$)$_2$.

In one embodiment of the invention, $R^2$ is 1-methoxyethyl, 1-hydroxyethyl, isopropyl, tert-butyl, ethyl, propyl, 1-methylpropyl, 1-ethylpropyl, 1-hydroxypropyl, 1-hydroxy-2-methylpropyl, 1-hydroxy-2,2-dimethylpropyl, α-hydroxycyclopropylmethyl, α-aminocyclopropylmethyl, α-(N-methylamino)cyclopropylmethyl, 1-ethoxyethyl, 1-trifluoromethoxyethyl, 1-(cyclopropyloxy)ethyl, 1-methoxy-2-methylpropyl, 1-hydroxy-1-methylethyl, 1-methoxy-1-methylethyl, 1-methoxypropyl, 1-methoxy-2,2-dimethylpropyl, 1-(2-methylpropoxy)ethyl, 1-(isopropoxy)ethyl, 1-(tert-butoxy)ethyl, 1-(2-methoxyethoxy)ethyl, 1-(phenoxy)ethyl, 1-(2-pyridyloxy)ethyl, 1-(3-pyridyloxy)ethyl, 1-(benzyloxy)ethyl, α-methoxybenzyl, 2-methoxyethyl, 1-(N-acetylamino)-2-methylpropyl, 1-amino-2-methylpropyl, acetyl, 3-aminopropyl, 2-amino-1,1-dimethylethyl, 1-amino-2-methylpropyl, 1-amino-2,2-dimethylpropyl, 1-methoxycyclopropylmethyl, 1-methoxyethyl, or

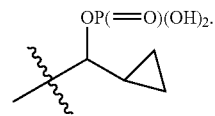

In one embodiment of the invention, $R^2$ is $NR^jR^k$.

In one embodiment of the invention, $R^2$ is N-methoxy-N-methylamino, N-methoxy-N-ethylamino, N-ethoxy-N-methylamino, N-ethoxy-N-ethylamino, N-t-butoxy-N-methylamino, N-isopropoxy-N-ethylamino, N-ethoxy-N-isopropylamino, N-ethoxy-N-t-butylamino, N,N-dimethylamino, N-hydroxy-N-methylamino, methylamino, N-(4-piperidyl)-N-methylamino, N-(1-acetylpiperid-4-yl)-N-methylamino, N-(3-aminopropyl)-N-methylamino, N-hydroxymethyl-N-methylamino, N-phosphorylmethyl-N-methylamino, N-hydroxylmethyl-N-ethylamino, N-(2-hydroxyethyl)-N-ethylamino, N-3-hydroxypropyl)-N-ethylamino, N-(4-hydroxybutyl)-N-ethylamino, N-(2-aminoethyl)-N-ethylamino, N-(3-aminopropyl)-N-ethylamino, N-(4-aminobutyl)-N-ethylamino, 1-azetidinyl, 1-pyrrolidinyl, 1-piperidino, or 4-morpholino.

In one embodiment of the invention, $R^2$ is $(C_3-C_{10})$cycloalkyl optionally substituted with one or more $R^o$.

In one embodiment of the invention, $R^2$ is cyclobutyl, cyclopentyl, 1-methylcyclopropyl, 1-trifluoromethylcyclopropyl, 1-hydroxycyclopropyl, 1-methoxycyclopropyl or 2-fluorocyclohexyl.

In one embodiment of the invention, $R^2$ is $C(=NR^h)R^i$.

In one embodiment of the invention, $R^2$ is 1-hydroxyiminoethyl or 1-methoxyiminoethyl.

In one embodiment of the invention, $R^2$ is heterocycle, aryl, or heteroaryl, wherein each $R^2$ is optionally substituted with one or more $R^o$.

In one embodiment of the invention, $R^2$ is 3-pyridyl, 2-pyridyl, 3-methyl-2-furyl, 2-methyl-5-thiazolyl, 3-aminophenyl, 5-methyl-2-thienyl, or tetrahydrofuranyl.

In one embodiment of the invention, $R^2$ is 1-methoxyethyl, 1-hydroxyethyl, or N-methoxy-N-methylamino.

In one embodiment of the invention, $C(=O)R^2$ is (S)-2-methoxypropanoyl or (S)-2-hydroxypropanoyl.

In one embodiment of the invention, $R^3$ is aryl that is optionally substituted with one or more groups independently selected from halo, cyano, nitro, difluoromethyl, trifluoromethyl, difluoromethoxy, trifluoromethoxy, azido, $—OR^a$, $NR^aR^b$, $—C(=O)R^a$, $—C(=O)OR^a$, $—NR^aC(=O)OR^d$, $—C(=O)NR^aR^b$, $(C_1-C_{10})$alkyl, $(C_3-C_{10})$cycloalkyl, $(C_2-C_{10})$alkenyl, and $(C_2-C_{10})$alkynyl.

In one embodiment of the invention, $R^3$ is phenyl that is optionally substituted with one or more groups independently selected from halo, cyano, nitro, difluoromethyl, trifluoromethyl, difluoromethoxy, trifluoromethoxy, azido, $—OR^a$, $—NR^aR^b$, $—C(=O)R^a$, $—C(=O)OR^a$, $—NR^aC(=O)OR^d$, $—C(=O)NR^aR^b$, $(C_1-C_{10})$alkyl, $(C_3-C_{10})$cycloalkyl, $(C_2-C_{10})$alkenyl, and $(C_2-C_{10})$alkynyl.

In one embodiment of the invention, $R^3$ is phenyl.

In one embodiment of the invention, $R^4$ is $Z—NR^g—C(=NR^h)R^i$, $Z—NR^gC(=NR^h)NR^jR^k$, $Z—NR^m—NR^n—C(=NR^h)R^i$, $Z—R^g—C(=CHR^q)NR^jR^k$, or $Z—NR^m—NR^n—C(=NR^h)NR^jR^k$.

In one embodiment of the invention, $R^4$ is $Z—C(=NR^h)NR^jR^k$.

In one embodiment of the invention, $R^4$ is $Z—O—NR^gC(=NR^h)NR^jR^k$, $Z—O—NR^g—C(=NR^h)R^i$, $Z—O—NR^jR^k$, $Z—O—Z—C(=NR^h)NR^jR^k$, or $Z—N=C(R^r)_2$.

In one embodiment, $R^h$ is CN, $C(O)NH_2$, $C(O)Me$, OMe, $CH_3$ or H.

In one embodiment, $R^g$ is H.

In one embodiment, $R^j$ and $R^k$ are independently H, $CH_3$ or $C(O)Me$.

In one embodiment of the invention, $R^4$ is selected from the following structures:

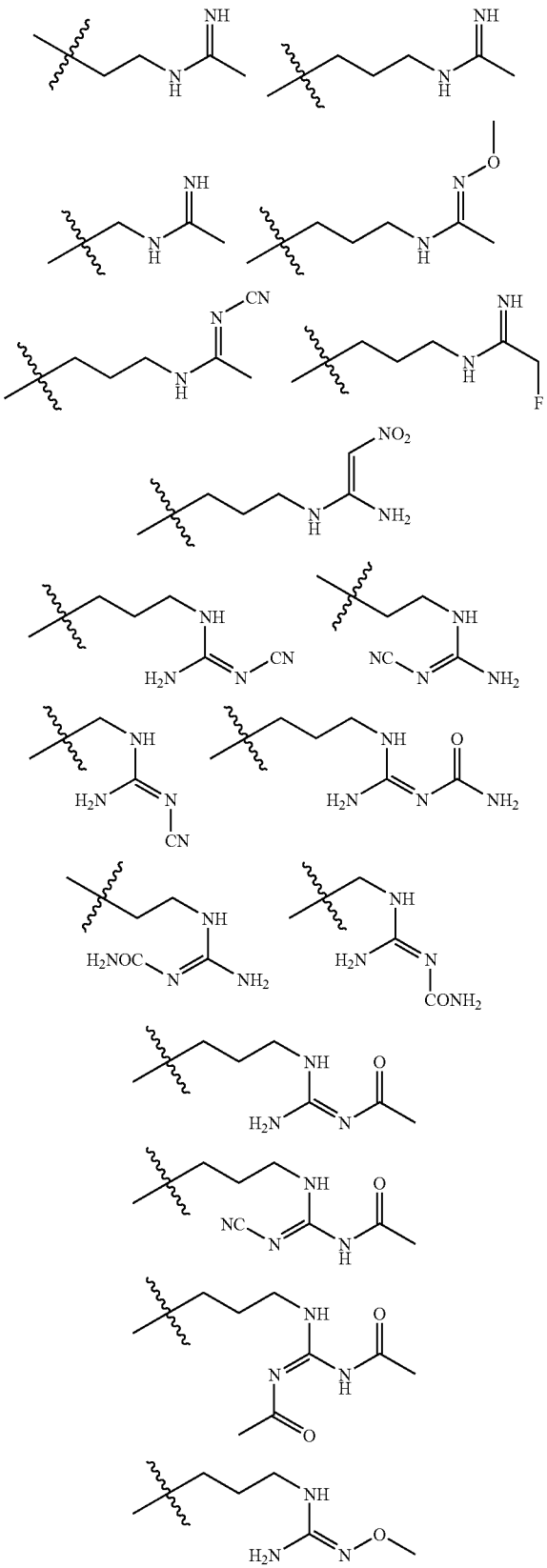

-continued
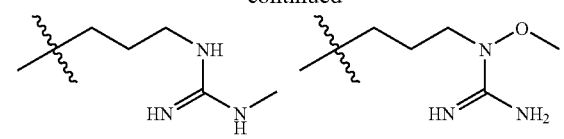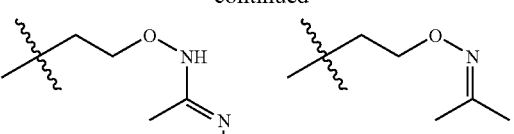
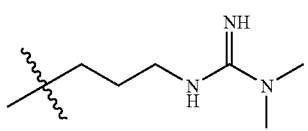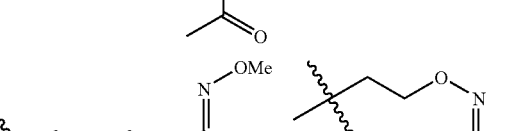
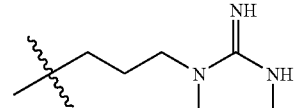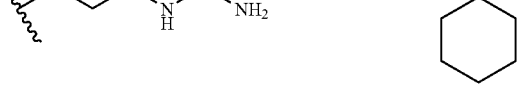
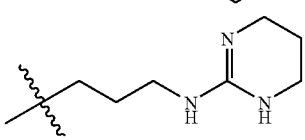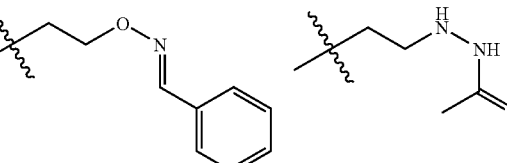
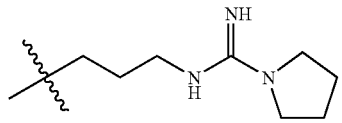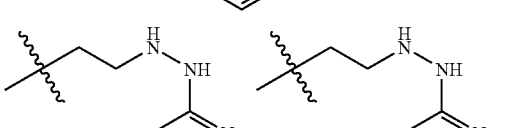
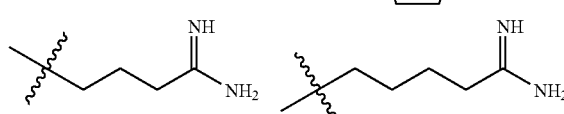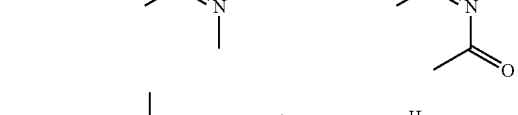
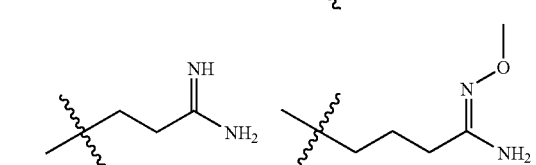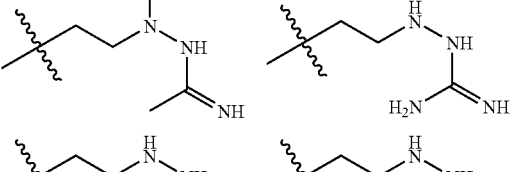
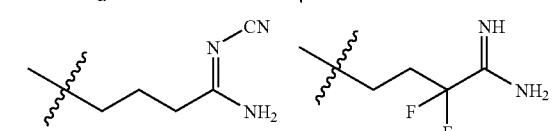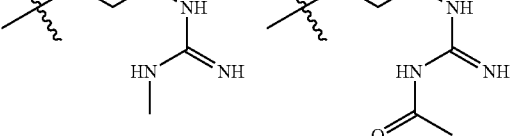
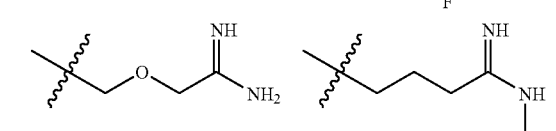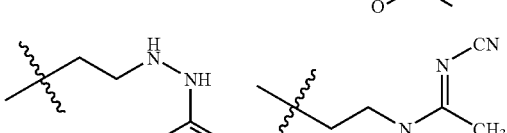
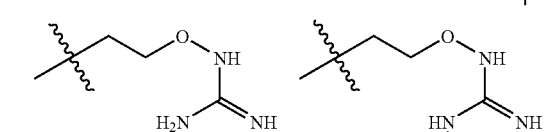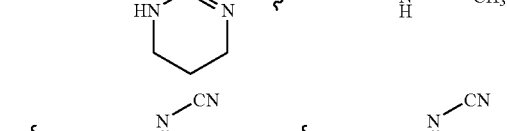
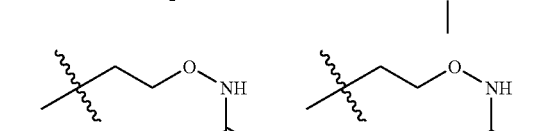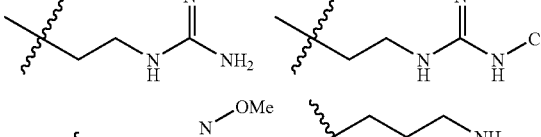
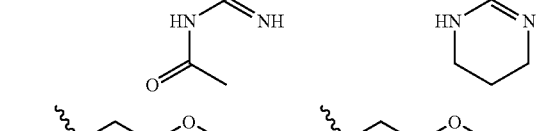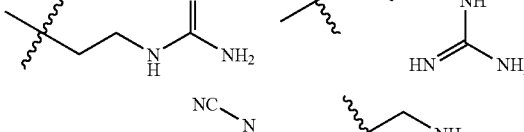
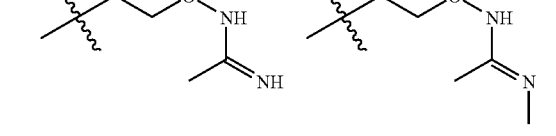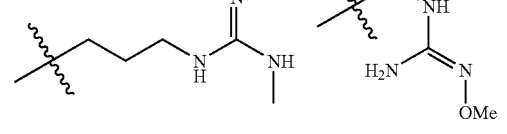

-continued

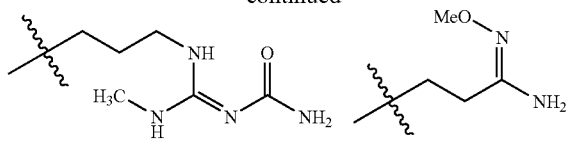

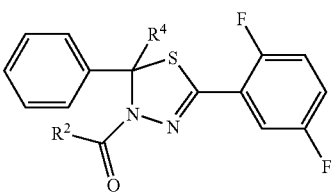

In one embodiment of the invention, $R^4$ has the following structure:

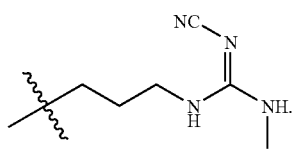

In one embodiment of the invention, Z is $(C_1-C_{10})$alkylene optionally substituted with one or more halogens.

In one embodiment of the invention, Z is ethylene, propylene, methylene, or —$CH_2CH_2CF_2$—.

In another embodiment of the invention, compounds of Formula II are provided:

$$\text{II}$$

wherein $R^2$ and $R^4$ are as defined above.

Salts

The compounds of the invention include salts of the compounds of Formula I. Such salts may be useful as intermediates for preparing and/or purifying compounds of Formula I and/or for separating enantiomers of compounds of Formula I. In one particular embodiment, the invention provides a pharmaceutically acceptable salt of a compound of Formula I.

The term "pharmaceutically acceptable salt," includes salts that are not biologically or physiologically undesirable. A compound of Formula I may posses a sufficiently acidic functional group, a sufficiently basic functional group, or both so that it can form a salt. Examples of such salts include those prepared by reaction of a compound with an organic or inorganic acid or base. Since a single compound of Formula I may include more than one acidic or basic moiety, the compounds of the present invention may include mono, di or tri-salts in a single compound.

Salts may be prepared by any suitable method, for example, by treatment of the free acid with an inorganic or organic base, or by ion exchange chromatography.

Compound Preparation

The compounds may be prepared using techniques available in the art using starting materials that are readily available or that can be synthesized using methods known in the art. For example, the compounds can be prepared the reaction routes illustrated in Schemes I-VII below.

In the preparation of some analogues such as described in Schemes I-VII, the use of appropriate protecting groups for functionality contained within the various substituents may be desirable. In these cases, protection and deprotection of said functionality can be accomplished using standard methods known by and available to those skilled in the art. For a general description of protecting groups and their use, see T. W. Greene, Protective Groups in Organic Synthesis, John Wiley & Sons, New York, 1991.

For illustrative purposes, Schemes I-VII show general methods for preparing die compounds of the present invention as well as key intermediates. For a more detailed description of the individual reaction steps, see the Examples section below. Those skilled in the art will appreciate that other synthetic routes may be used to synthesize the compounds of the invention.

Although specific starting materials and reagents are depicted in the Schemes and discussed below, other starting materials and reagents can be substituted to provide a variety of derivatives and/or reaction conditions. In addition, many of the compounds prepared by the methods described below can be further modified in light of this disclosure using conventional chemistry well known to those skilled in the art to provide other compounds of Formula I.

Scheme I

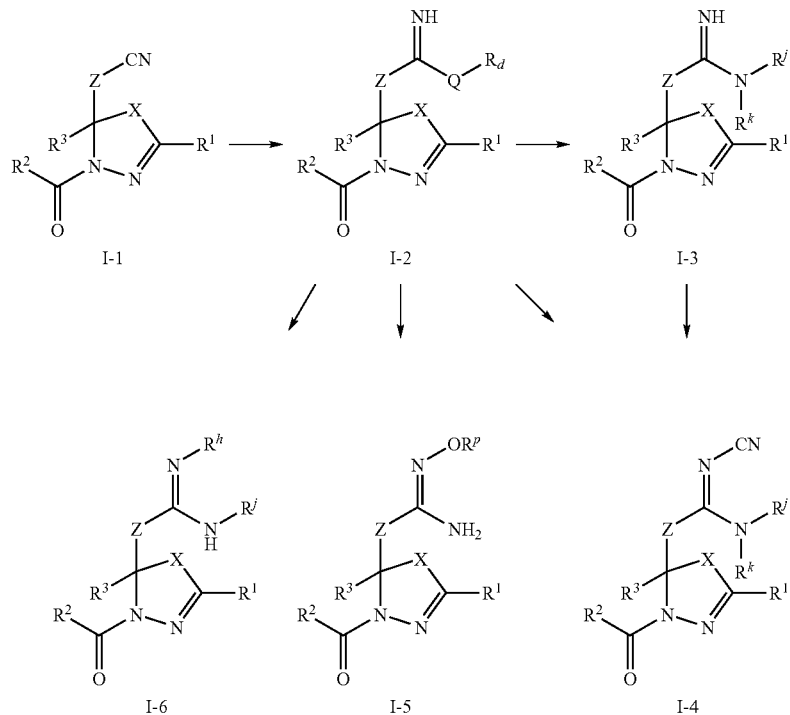

Scheme I illustrates a method of preparing compounds of Formulas I-3, I-4, I-5, I-6 and I-7. I-1 can be synthesized in a manner similar to that previously described (U.S. Patent Application 60/620,048, published as WO 2006/044825). Nitrile I-1 can be converted to imidate I-2 wherein Q is oxygen by treatment with an anhydrous solution of HCl in methanol, ethanol or other appropriate alcohol at lowered or ambient temperatures. I-1 can be concerted to thioimidate I-2 wherein Q is sulfur by treatment with HCl and the appropriate thiol in neat thiol or a suitable solvent such as methanol, ethanol, ether or benzene. In one embodiment, I-1 is subjected to anhydrous ethanolic HCl at 0° C. and allowed to warm to room temperature to afford the hydrochloride salt of I-2 wherein Q is oxygen and $R_d$ is ethyl. I-2 can then be converted to amidine I-3 by treatment with ammonia or the appropriate amine in ethanol, methanol or other appropriate solvent. Preferably, I-2 is treated with an amine in methanol at room temperature to afford I-3 or a tautomer thereof. I-4 can be obtained by subjecting the hydrochloride salt I-2 to cyanamide in alcoholic solvent, followed by treatment with triethylamine or other suitable base and the appropriate amine. Alternatively, I-4 can be generated from I-3 by treatment with cyanogen bromide or cyanogen chloride and triethylamine or other suitable base in an appropriate solvent such as ethanol, acetonitrile, chloroform or DMF. I-5 is synthesized from I-2 by treatment with an alkoxyamine, hydroxylamine, or a salt thereof in the presence of triethylamine or other suitable base in ethanol, methanol, or other suitable solvent. Preferably, I-2, wherein Q is oxygen and $R_d$ is ethyl, is treated with the appropriate alkoxyamine hydrochloride in ethanol at room temperature to afford I-5 wherein $R^p$ is alkyl. I-6 can be produced from I-2 by subjecting I-2 to the appropriate monosubstituted amine at room temperature or elevated temperature in ethanol, methanol, or other appropriate solvent.

Scheme II

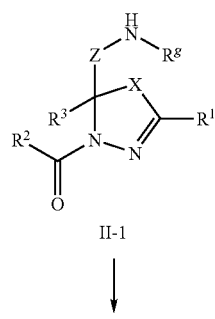

II-1

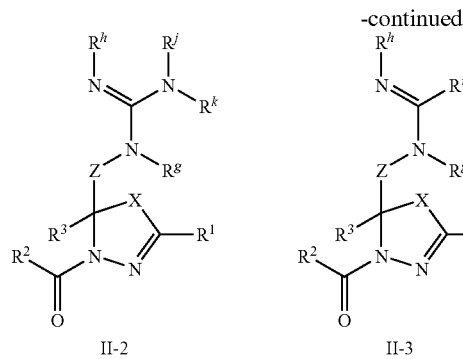
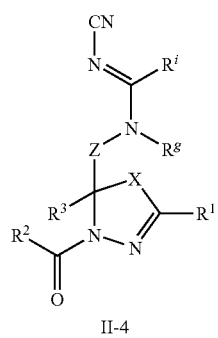

Scheme II illustrates a method of preparing compounds of Formulas II-2, II-3 and II-4. Amines of the Formula II-1 are prepared as previously described (U.S. patent application 60/620,048, published as WO 2006/044825). Amine II-1 can be converted to II-2 by treatment with a guanidinylating reagent such as, but not limited to, a substituted or unsubstituted S-methylisothiourea, carbodiimide, 3,5-dimethyl-1H-pyrazole-1-carboxamidine or aminoiminomethanesulfonic acid reagent in an appropriate solvent and at elevated temperature if necessary.

Alternatively, II-2 can be prepared by subjecting II-1 to a N-protected guanidinylating reagent such as, but not limited to, di-Boc-S-methylisothiourea, di-CBz-triflylguanidine, or N,N'-bis(tert-butoxycarbonyl)-1H-pyrazole-1-carboxamidine in a suitable solvent followed by subsequent removal of the protecting groups under the appropriate conditions to provide II-2 or a tautomer thereof. In one embodiment, amine II-1 is treated with N,N'-bis(tert-butoxycarbonyl)-1H-pyrazole-1-carboxamidine in tetrahydrofuran, followed by treatment with hydrochloric acid in dioxane to remove the tert-butoxycarbonyl protecting groups to afford II-2 or a tautomer thereof wherein $R^g$, $R^h$ and $R^j$ are hydrogen. Compound II-3 can be obtained from amine II-1 by treatment with the appropriate imidate or imidate salt in combination with a suitable base, in an alcoholic solvent at elevated temperature. Preferably, amine II-1 is treated with the hydrochloride salt of an ethyl imidate and triethylamine in refluxing anhydrous ethanol to afford II-3 or a tautomer thereof. Compound II-4 is prepared by treatment of amine II-1 with the appropriate cyanoimidate or cyanoimidate salt in combination with a suitable base, in an alcoholic solvent. Preferably, amine II-1 is treated with an N-cyano ethyl imidate hydrochloride and triethylamine in anhydrous ethanol to afford II-4 or a tautomer thereof.

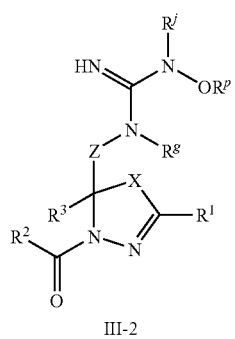

Scheme III illustrates a method of preparing compounds of Formula III-2. Amine II-I can be converted to compound III-1 by treatment with cyanogen bromide or cyanogen chloride in the presence of a suitable base and appropriate solvent. In one embodiment, amine II-1 is treated with cyanogen bromide and triethylamine in methylene chloride. Compound III-2 can be prepared by treatment of compound III-1 with excess of an alkoxyamine or alkoxyamine salt in the presence of an appropriate base in a suitable solvent optionally at elevated temperatures. Preferably, III-1 is treated with excess alkoxyamine hydrochloride salt and triethylamine in ethanol at reflux temperature to provide III-2 or a tautomer thereof.

Scheme III

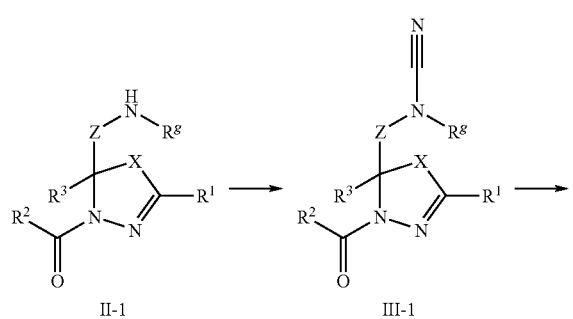

Scheme IV

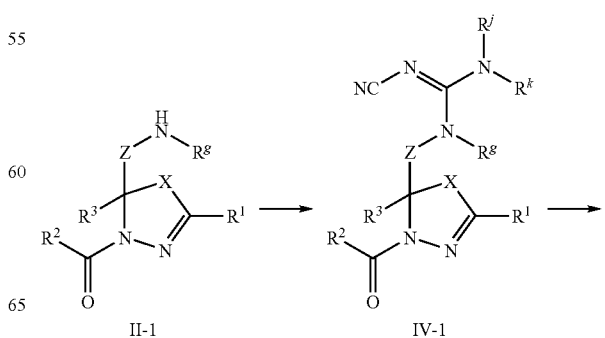

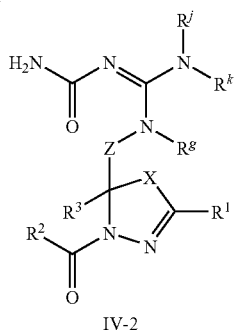

IV-2

Scheme IV illustrates a method of preparing compounds of Formulas IV-1 and IV-2. Compound IV-1 can be prepared in one step from amine II-1 by treatment with a cyano-guanidinylating reagent such as, but not limited to, an N-cyanocarbamimidate, an S-alkyl-N-cyanocarbamimidothioate or dicyanamide salt. Alternatively, compound IV-1 can be synthesized in a two-step procedure from II-1 by initial treatment with a reagent including, but not limited to an N-cyanocarbonimidate or an N-cyanocarbonimidodithioate, optionally in the presence of a suitable base, followed by subsequent treatment with ammonia or the appropriate amine. In one embodiment, the hydrochloride salt of amine II-1 is subjected to diphenylcyanocarbonimidate and triethylamine in isopropanol at room temperature, followed by treatment with ammonia or the appropriate amine in methanol at reflux temperature. Compound IV-2 can be prepared by treatment of compound IV-1 with acid and water in a suitable solvent. Preferably, compound IV-1 is treated with hydrochloric acid in methanol and water to provide compound IV-2 or a tautomer thereof Scheme V illustrates a method of preparing compounds of Formulas V-2 and V-3. Alkoxyamines of the Formula V-I can be prepared by a similar route to the preparation of amines of the Formula II-1 using the appropriate N-protected ketone precursor. Compound V-2 can be prepared by treatment of alkoxyamine V-1 with the appropriate imidate or imidate salt in combination with a suitable base, in an alcoholic solvent at elevated temperature. Preferably, alkoxyamine V-1 is treated with the hydrochloride salt of an ethyl imidate and triethylamine in refluxing absolute ethanol to afford V-2 or a tautomer thereof. Compound V-3 can be prepared by treatment of alkoxyamine V-1 with a guanidinylating reagent such as, but not limited to, a substituted or unsubstituted S-methyl isothiourea, carbodiimide, 3,5-dimethyl-1H-pyrazole-1-carboxamidine or aminoiminomethanesulfonic acid reagent in the appropriate solvent and at elevated temperature if necessary. Alternatively, V-3 can be prepared by subjecting V-1 to a N-protected guanidinylating reagent such as, but not limited to, di-Boc-S-methylisothiourea, di-CBz-trifylguanidine, or N,N'-bis(tert-butoxycarbonyl)-1H-pyrazole-1-carboxamidine in a suitable solvent followed by removal of the protecting groups under the appropriate conditions to provide V-3 or a tautomer thereof. In one embodiment, alkoxyamine V-1 is treated with N,N-bis(tert-butoxycarbonyl)-1H-pyrazole-1-carboxamidine in tetrahydrofuran, followed by treatment with hydrochloric acid in dioxane to remove the tert-butoxycarbonyl protecting groups to afford V-3 or a tautomer thereof wherein $R^h$, $R^j$ and $R^k$ are hydrogen.

Scheme VI

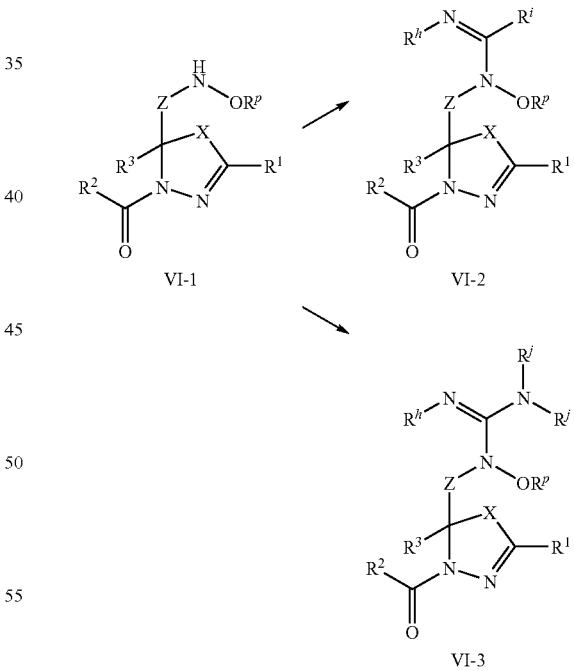

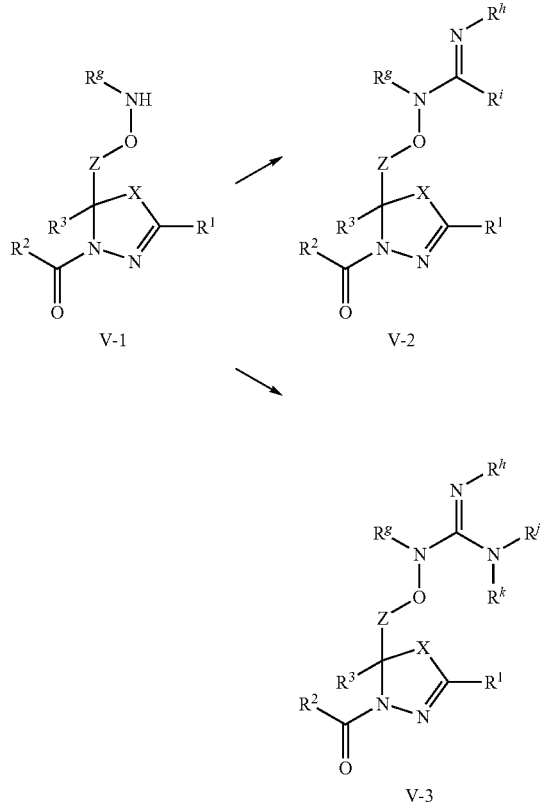

Scheme VI illustrates a method of preparing compounds of Formulas VI-2 and VI-3. Alkoxyamines of the Formula VI-I can be prepared by a similar route to the preparation of amines of the Formula II-1 using the appropriate N-protected ketone precursor. Compound VI-2 can be prepared by treatment of alkoxyamine VI-1 with the appropriate imidate or imidate salt in combination with a suitable base, in an alcoholic solvent at elevated temperature. In one embodiment, alkoxyamine VI-1 is treated with the hydrochloride salt of an ethyl imidate and triethylamine in refluxing absolute ethanol to afford VI-2 or a tautomer thereof. Compound VI-3 can be prepared by treatment of alkoxyamine VI-1 with a guanidinylating reagent such as, but not limited to, a substituted or unsubstituted S-methylisothiourea, carbodiimide, 3,5-dimethyl-1H-pyrazole-1-carboxamidine or aminoiminomethanesulfonic acid reagent in the appropriate solvent and at elevated temperature if necessary. Alternatively, Vi-3 can be prepared by subjecting VI-1 to a N-protected guanidinylating reagent such as, but not limited to, di-Boc-S-methylisothiourea, di-CBz-trifylguanidine, or N,N'-bis(tert-butoxycarbonyl)-1H-pyrazole-1-carboxamidine in a suitable solvent followed by removal of the protecting groups under the appropriate conditions to provide VI-3 or a tautomer thereof. In one embodiment, alkoxyamine VI-1 is treated with N,N'-bis(tert-butoxycarbonyl)-1H-pyrazole-1-carboxamidine in tetrahydrofuran, followed by treatment with hydrochloric acid in dioxane to remove the tert-butoxycarbonyl protecting groups to afford VI-3 wherein $R^h$, $R^i$ and $R^j$ are hydrogen.

Scheme VII

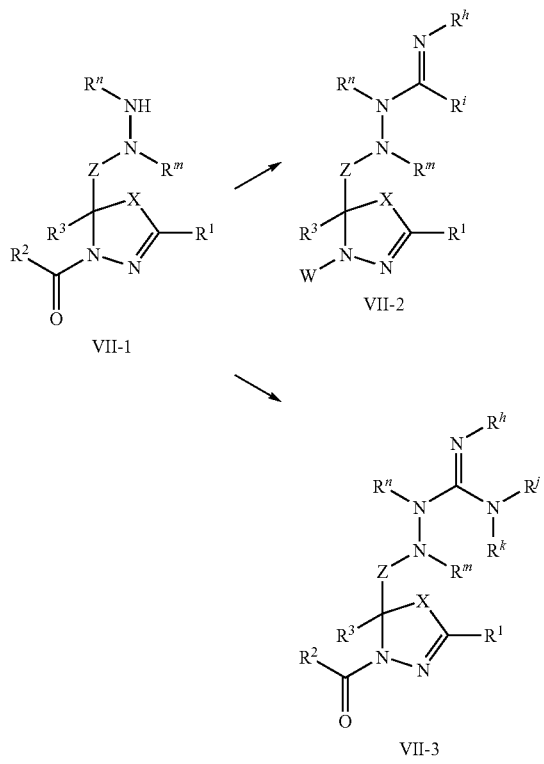

Scheme VII illustrates a method of preparing compounds of the Formulas VII-2 and VII-3. Hydrazines of the Formula VII-1 can be prepared by a similar route to the preparation of amines of the Formula II-1 using the appropriate N-protected ketone precursor. Compound VII-2 can be prepared by treatment of hydrazine VII-1 with the appropriate imidate or imidate salt in combination with a suitable base, in an alcoholic solvent at elevated temperature. Preferably, hydrazine VII-1 is treated with the hydrochloride salt of an ethyl imidate and triethylamine in refluxing absolute ethanol to afford VII-2 or a tautomer thereof. Compound VII-3 can be prepared by treatment of hydrazine VII-1 with a guanidinylating reagent such as, but not limited to, a substituted or unsubstituted S-methylisothiourea, carbodiimide, 3,5-dimethyl-1H-pyrazole-1-carboxamidine or aminoiminomethanesulfonic acid reagent in the appropriate solvent and at elevated temperature if necessary. Alternatively, VII-3 can be prepared by subjecting VII-1 to a N-protected guanidinylating reagent such as, but not limited to, di-Boc-S-methylisothiourea, di-CBz-trifylguanidine, or N,N'-bis(tert-butoxycarbonyl)-1H-pyrazole-1-carboxamidine in a suitable solvent followed by removal of the protecting groups under the appropriate conditions to provide VII-3 or a tautomer thereof. In one embodiment, hydrazine VII-1 is treated with N,N'-bis(tert-butoxycarbonyl)-1H-pyrazole-1-carboxamidine in tetrahydrofuran, followed by treatment with hydrochloric acid in dioxane to remove the tert-butoxycarbonyl protecting groups to afford VII-3 wherein $R^h$, $R^j$ and $R^k$ are hydrogen.

In one embodiment, the invention provides a method for preparing a compound of Formula I or a salt thereof comprising:

a) deprotecting a corresponding compound that comprises one or more protecting groups;

b) for a salt of a compound of Formula I, forming a salt from a corresponding compound of Formula I;

c) for a compound of Formula I, % wherein $R^4$ is Z—C(=NH)$NR^jR^k$, by reacting a corresponding compound wherein $R^4$ is Z—C(=NH)$OR_d$, wherein $R_d$ is $(C_1\text{-}C_{10})$alkyl with a corresponding amine $HNR^jR^k$;

d) for a compound of Formula I, wherein $R^4$ is Z—C(=NCN)$NR^jR^k$, reacting a corresponding compound wherein $R^4$ is Z—C(=NH)$OR_d$, wherein $R_d$ is $(C_1\text{-}C_{10})$alkyl with cyanamide followed by treatment with a corresponding amine $HNR^jR^k$;

e) for a compound of Formula I, % wherein $R^4$ is Z—C(=$NOR^p$)$NH_2$, reacting a corresponding compound wherein $R^4$ is Z—C(=NH)$OR_d$, wherein $R_d$ is $(C_1\text{-}C_{10})$alkyl with a corresponding amine $NH_2(OR^p)$;

f) for a compound of Formula I, wherein $R^4$ is Z—$NR^g$—C(=$NR^h$)$NR^jR^k$, reacting a corresponding compound wherein $R^4$ is Z—$NHR^g$ with a guanidinylating reagent;

g) for a compound of Formula I, wherein $R^4$ is Z—$NR^g$—C(=$NR^h$)$NR^jR^k$, reacting a corresponding compound wherein $R^4$ is Z—$NHR^g$ with an N-protected guanidinylating reagent, followed by deprotection;

h) for a compound of Formula I, wherein $R^4$ is Z—$NR^g$—C(=$NR^h$)$R^i$, reacting a corresponding compound wherein $R^4$ is Z—$NHR^g$ with a corresponding imidate or imidate salt;

i) for a compound of Formula I, wherein $R^4$ is Z—$NR^g$—C(=NCN)$R^i$, reacting a corresponding compound wherein $R^4$ is Z—$NHR^g$ with a corresponding cyanoimidate or cyanoimidate salt;

j) for a compound of Formula I, wherein $R^4$ is Z—$NR^g$—C(=NH)$NR^j(OR^p)$, treating a corresponding compound wherein $R^4$ is Z—$NR^g$—CN with a corresponding alkoxyamine or alkoxyamine salt;

k) for a compound of Formula I, wherein $R^4$ is Z—$NR^g$—C(=$NR^h$)$NR^jR^k$, wherein $R^h$ is aminocarbonyl, treating a corresponding compound wherein $R^h$ is cyano with acid in an aqueous solvent;

l) for a compound of Formula I, wherein $R^4$ is Z—O—$NR^g$—C(=$NR^h$)$R^i$, treating a corresponding compound wherein $R^4$ is Z—O—$NHR^g$ with a corresponding imidate or imidate salt;

m) for a compound of Formula I, wherein $R^4$ is Z—O—$NR^gC$(=$NR^h$)$NR^jR^k$, treating a corresponding compound wherein $R^4$ is Z—O—$NHR^g$ with a corresponding guanidinylating reagent;

n) for a compound of Formula I, wherein $R^4$ is Z—O—$NR^gC$(=$NR^h$)$NR^jR^k$, treating a corresponding compound wherein $R^4$ is Z—O—NHR$^g$ with an N-protected guanidinylating reagent, followed by deprotection;

o) for a compound of Formula I, wherein $R^4$ is Z—N(OR$^p$)C(=NR$^h$)R$^i$, treating a corresponding compound wherein $R^4$ is Z—NH(OR$^p$) with a corresponding imidate or imidate salt.

p) for a compound of Formula I, wherein $R^4$ is Z—N(OR$^p$)C(=NR$^h$)NR$^j$R$^k$, treating a corresponding compound wherein $R^4$ is Z—NH(OR$^p$) with a corresponding guanidinylating reagent;

q) for a compound of Formula I, wherein $R^4$ is Z—N(OR$^p$)C(=NR$^h$)NR$^j$R$^k$, treating a corresponding compound wherein $R^4$ is Z—NH(OR$^p$) with a corresponding N-protected guanidinylating reagent, followed by deprotection;

r) for a compound of Formula I, wherein $R^4$ is Z—NR$^m$—NR$^n$—C(=NR$^h$)R$^i$, treating a corresponding compound wherein $R^4$ is Z—NR$^m$—NR$^n$—H with a corresponding imidate or imidate salt;

s) for a compound of Formula I, wherein $R^4$ is Z—NR$^m$—NR$^n$—C(=NR$^h$)NR$^j$R$^k$, treating a corresponding compound wherein $R^4$ is Z—NR$^m$—NR$^n$H with a corresponding guanidinylating reagent; or t) for a compound of Formula I, wherein $R^4$ is Z—NR$^m$—NR$^n$—C(=NR$^h$)NR$^j$R$^k$, treating a corresponding compound wherein $R^4$ is Z—NR$^m$—NR$^n$—H with a corresponding N-protected guanidinylating reagent, followed by deprotection.

Use

The compounds of the invention find use in a variety of applications. As will be appreciated by those skilled in the art, mitosis may be altered in a variety of ways. That is, one can affect mitosis either by increasing or decreasing the activity of a component in the mitotic pathway. Stated differently, mitosis may be affected (e.g., disrupted) by distributing equilibrium, either by inhibiting or activating certain components. Similar approaches may be used to alter meiosis.

In one embodiment, the compounds of the invention are used to modulate mitotic spindle formation, thus causing prolonged cell cycle arrest in mitosis. The term "modulate mitotic spindle formation" means altering mitotic spindle formation, including increasing and decreasing spindle formation. The term "mitotic spindle formation" refers to organization of microtubules into bipolar structures by mitotic kinesins. "Mitotic spindle dysfunction" refers to mitotic arrest and monopolar spindle formation.

The compounds of the invention are useful to bind to and/or modulate the activity of a mitotic kinesin. In an embodiment, the mitotic kinesin is a member of the bimC subfamily of mitotic kinesins as described in U.S. Pat. No. 6,284,480. In a further embodiment, the mitotic kinesin is human KSP, although the activity of mitotic kinesins from other organisms may also be modulated by the compounds of the present invention. In this context, modulate means either increasing or decreasing spindle pole separation, causing malformation, i.e., splaying, of mitotic spindle poles, otherwise causing morphological perturbation of the mitotic spindle. Also included within the definition of KSP for these purposes are variants and/or fragments of KSP. In addition, other mitotic kinesins may be inhibited by the compounds of the present invention.

The compounds of the invention are useful for treating diseases and conditions caused by abnormal cell growth or cellular proliferation. Disease states that can be treated by the methods and compositions provided herein include, but are not limited to, cancer, autoimmune disease, arthritis, graft rejection, inflammatory bowel disease, and proliferation induced after medical procedures, including, but not limited to, surgery, angioplasty, and the like. It is appreciated that in some cases the cells may not be in a hyperproliferative or hypoproliferative state (abnormal state), but still require treatment. For example, during wound healing, cells may be proliferating "normally", but proliferation enhancement may be desired. Similarly, in the agriculture arena, cells may be in a "normal" state, but proliferation modulation may be desired to enhance a crop by directly enhancing growth of a crop, or by inhibiting the growth of a plant or organism that adversely affects the crop. Thus, in one embodiment, the invention herein includes application to cells or individuals that are afflicted or may eventually become afflicted with any one of these disorders or states.

The compounds of the present invention may also be useful as antifungal agents, by modulating the activity of the fungal members of the bimC kinesin subgroup, as described in U.S. Pat. No. 6,284,480.

It is believed that the compounds of the present invention can render abnormal cells more sensitive to treatment with radiation for purposes of killing and/or inhibiting the growth of such cells. Accordingly, this invention further relates to a method for sensitizing abnormal cells in an animal to treatment with radiation, which comprises administering to the animal an amount of a compound of the invention, which amount is effective in sensitizing abnormal cells to radiation treatment.

Although the compounds of the invention are particularly useful as therapeutic agents for use in warn-blooded animals (including humans), they are also useful whenever it is required to inhibit the effects of KSP kinesin. Thus, they are also useful as pharmacological standards in the development of new biological tests and in the search for new pharmacological agents.

Combinations

The compounds of this invention may be used alone or in combination with other therapeutic agents. Accordingly, in one embodiment, the invention provides a method for treating a disorder in a mammal that comprises administering to said mammal a therapeutically effective amount of a compound of the present invention in combination with another therapeutic agent, e.g., an anti-tumor agent, radiation therapy, an inhibitor of one or more mitotic kinesins, a PPAR-γ agonist, a PPAR-δ agonist, a gene therapy agent; an inhibitor of inherent multi-drug resistance (e.g. p-glycoprotein inhibitors), an anti-emetic agent, an immunologic-enhancing agent, an agent useful in the treatment of anemia, or an agent useful in the treatment of neutropenia.

In one embodiment, the invention also provides a composition comprising 1) a compound of the invention; 2) another therapeutic agent; and 3) a pharmaceutically acceptable carrier.

Anti-tumor agents that can be administered or formulated with compounds of die invention include, but are not limited to:

(i) antiproliferative/anti-neoplastic drugs and combinations thereof, as used in medical oncology, such as alkylating agents (for example, cisplatin, carboplatin, cyclophosphamide, nitrogen mustard, melphalan, chlorambucil, busulphan and nitrosoureas); anti-metabolites (for example, antifolates such as such as fluoropyrimidines like 5-fluorouracil and tegafur, raltitrexed, methotrexate, cytosine arabinside, hydroxyurea, or, one of the preferred anti-metabolites disclosed in European Patent Application No. 239362 such as N-(5-[N-(3,4-dihydro-2-methyl-4-oxoquinazolin-6-ylm-ethyl)-N-methylamino]-2-thenoyl)-L-glutamic acid); antitumor antibiotics (for example, anthracyclines like adriamycin, bleomycin, doxorubicin, daunomycin, epirubicin, idarubicin, mitomycin-C, dactinomycin and mithramycin); antimitotic agents (for example, vinca alkaloids like vincristine, vinblastine, vindesine and vinorelbine and taxoids like taxol and taxotere); and topoisomerase inhibitors (for example epipodophyllotoxins like eptoposide and teniposide, amsacrine, topotecan and campothecin);

(ii) cytostatic agents such as anti-estrogens (for example, tamoxifen, toremifene, raloxifene, droloxifene and iodoxyfene), estrogen receptor down regulators (for example, fulvestratrant), anti-androgens (for example, bicalutamide, flutamide, nilutamide, cyproxerone acetate and Casodex® (4'-cyano-3-(4-fluorophenylsulphonyl)-2-hydroxy-2-methyl-3'-(trifluoromethyl)propionanilide)), LHRH antagonists or LHRH agonists (for example, goserelin, leuporelin and buserelin), progestogens (for example, megestrol acetate), aromatase inhibitors (for example, anastrozole, letrozole, vorazole and exemestane) and inhibitors of 5α-reductase such as finasteride;

(iii) agents that inhibit cancer cell invasion (for example, metalloproteinase inhibitors like marimastat and inhibitors of urokinase plasminogen activator receptor function);

(iv) inhibitors of growth factor function like growth factor antibodies, growth factor receptor antibodies (for example, the anti-erbB2 antibody trastumuzab [Herceptin®] and the anti-erbB1 antibody cetuximab [C225]), farnesyl transferase inhibitors, tyrosine kinase inhibitors and serine-threonine kinase inhibitors (for example, inhibitors of the epidermal growth factor family tyrosine kinases such as N-(3-chloro-4-fluorophenyl)-7-methoxy-6-(3-morpholinopropoxy) quinazolin-4-amine (gefitinib, AZD1839). N-(3-ethynylphenyl)-6,7-bis(2-methoxyethoxy)quinazolin-4-amine (erlotinib, OSI-774) and 6-acylamido-N-(3-chloro-4-fluorophenyl)-7-(3-morpholinopropoxy)quinazolin-4-amine (CI 1033)), inhibitors of the platelet-derived growth factor family and inhibitors of the hepatocyte growth factor family;

(v) anti-angiogenic agents such as those that inhibit the effects of vascular endothelial growth factor (for example, the anti-vascular endothelial cell growth factor antibody bevacizumab [Avastin®], compounds such as those disclosed in PCT Publication Nos. WO 97/22596, WO 97/30035, WO 97/32856, and WO 98/13354) and compounds that work by other mechanisms (for example, linomide, inhibitors of integrin αvβ3 function, MMP inhibitors, COX-2 inhibitors and angiostatin);

(vi) vascular damaging agents such as Combretastatin A4 and compounds disclosed in PCT Publication Nos. WO 99/02166, WO 0/40529, WO 00/41669, WO 01/92224, WO 02/04434, and WO 02/08213;

(vii) antisense DNA or RNA therapies (for example, those that are directed to the targets listed above such as ISIS 2503, and anti-ras antisense);

(viii) gene therapy approaches, including for example GVAX™, approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy;

(ix) interferon;

(x) immunotherapy approaches, including for example ex-vivo and in-vivo approaches to increase the immunogenicity of patient tumor cells, such as transfection with cytokines such as interleukin 2, interleukin 4 or granulocyte-macrophage colony stimulating factor, approaches to decrease T-cell anergy, approaches to using transfected immune cells such as cytokine-transfected dendritic cells, approaches using cytokine-transfected tumor cell lines and approaches using anti-idiotypic antibodies; and (xi) miscellaneous agents such as intercalating antibiotics, signal transduction inhibitors, cell cycle inhibitors, enzyme inhibitors, retinoid receptor modulators, proteasome inhibitors, biological response modifiers, anti-hormones, targeted antibodies, HMG-CoA reductase inhibitors, and prenyl-protein transferase inhibitors.

Inhibitors of mitotic kinesins that can be administered or formulated with compounds of the invention are described in PCT Publication Nos. WO 00/130,768, WO 01/30768, WO 01/98278, WO 03/050,064, WO 03/050,122, WO 03/049, 527, WO 03/049,679, WO 03/049,678, WO 03/39460 WO 03/079,973, WO 03/088,903, WO 03/094,839, WO 03/097, 053, WO 03/099,211, WO 03/099,286, WO 03/103,575, WO 03/105,855, WO 03/106,426, WO 04/032,840, WO 04/034, 879, WO 04/037,171, WO 04/039,774, WO 04/055,008, WO 04/058,148, WO 04/058,700 and WO 04/064,741.

PPAR-γ and PPAR-δ agonists that can be administered or formulated with compounds of the invention include proglitazone, rosiglatazone, gene therapy agents, and inhibitors or inherent multi-drug resistance (e.g. p-glycoprotein inhibitors).

Neutropenia treatment agents that can be administered or formulated with compounds of the invention include, for example, a hematopoietic growth factor, which regulates the production and function of neutrophils such as a human granulocyte colony stimulating factor, (G-CSF). An example of a G-CSF is filgrastim.

Immunologic-enhancing agents that can be administered or formulated with compounds of the invention include levamisole, isoprinosine and Zadaxin.

Pharmaceutical Compositions

The compounds of the invention may be administered by any convenient route, e.g. into the gastrointestinal tract (e.g. rectally or orally), the nose, lungs, musculature or vasculature or transdermally. The compounds may be administered in any convenient administrative form, e.g. tablets, powders, capsules, solutions, dispersions, suspensions, syrups, sprays, suppositories, gels, emulsions, patches etc. Such compositions may contain components conventional in pharmaceutical preparations, e.g. diluents, carriers, pH modifiers, sweeteners, bulking agents, and further active agents. If parenteral administration is desired, the compositions will be sterile and in a solution or suspension form suitable for injection or infusion. Such compositions form a further aspect of the invention.

According to another aspect, the present invention provides a pharmaceutical composition, which comprises a compound of Formula I or a pharmaceutically acceptable salt thereof, as defined hereinabove. In one embodiment, the pharmaceutical composition includes the compound of Formula I together with a pharmaceutically acceptable diluent or carrier.

Dosages

It will be understood that the specific dosage level and frequency of dosage for any particular subject may be varied and will depend upon a variety of factors including the activity of the specific compound of Formula I, the species, age, body weight, general health, sex and diet of the subject, the mode and time of administration, rate of excretion, drug combination, and severity of the particular condition, but can nevertheless be routinely determined by one skilled in the art.

Although the amount of a compound of this invention that is combined with one or more excipients to produce a single dosage form will necessarily vary depending upon the subject treated, the severity of the disorder or condition, the rate of administration, the disposition of the compound and the discretion of the prescribing physician, an effective dosage will typically be in the range of about 0.001 to about 100 mg per kg body %% eight per day, preferably about 0.5 to about 35 mg/kg/day, in single or divided doses. For a 70 kg human, this would amount to about 0.0035 to 2.5 g/day, preferably about 0.05 to about 2.5 g/day. In some instances, dosage levels below the lower limit of the aforesaid range may be more thian adequate, while in other cases still larger doses may be employed without causing any harmful side effect. For further information on routes of administration and dosage regimes, see Chapter 25.3 in Volume 5 of *Comprehensive Medicinal Chemistry* (Corwin Hansch; Chairman of Editorial Board), Pergamon Press 1990.

Kits

In another embodiment of the invention, an article of manufacture, or "kit", containing materials useful for the treatment of the disorders described above is provided. In one embodiment, the kit comprises a container comprising a compound of the invention. The kit may further comprise a label or package insert on or associated with the container. Suitable containers include, for example, bottles, vials, syringes, and blister packs.

The container may be formed from a variety of materials such as glass or plastic. The container may have a sterile access port (for example, the container may be an intravenous solution bag or a vial having a stopper pierceable by a hypodermic injection needle).

The label or package insert mats indicate that the composition is used for treating a given condition, such as cancer. In one embodiment, the label or package inserts indicates that the compound of the invention can be used to treat a disorder resulting from abnormal cell growth. The label or package insert may also indicate that the composition can be used to treat other disorders. Alternatively, or additionally, the kit may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the compound of the invention, and, if present, another therapeutic agent. For example, if the kit comprises a compound of the invention and a second therapeutic agent, the kit may further comprise directions for the simultaneous, sequential or separate administration of the compound of the invention and the second therapeutic agent to a patient in need thereof.

Accordingly this invention also provides a kit for treating an abnormal cell growth condition, wherein said kit comprises a) a compound of the invention; and b) instructions for use. In certain embodiments, the kit further comprises c) a second therapeutic agent (e.g. an agent having anti-hyperproliferative activity). In one embodiment, the compound of the invention and the second therapeutic agent are contained in separate containers. In another embodiment, the compound of the invention and the second therapeutic agent are in the same container.

Assays

The biological activities of the compounds of the invention can be evaluated with the following assays.

Enzyme Assay

The activity of the compounds of the present invention may be determined by the following procedure. The assays were conducted at 30° C. in a Costar 3695 (96-well, polystyrene, ½-area, clear) plate in a final volume of 50 µL. Hydrolysis of ATP was monitored in a system that coupled the product ADP to the oxidation of NADH using pyruvate kinase and lactate dehydrogenase. Assay mixtures contained the following: 20 mM K$^+$Pipes, pH 7.0, 0.01% Triton X-100, 2% DMSO, 25 mM KCl, 2 mM MgCl$_2$, 1 mM DTT, 25 µM ATP, 1 mM phospho(enol)pyruvate, 200 µM NADH, 7.9 U/mL pyruvate kinase, 9 U/mL lactate dehydrogenase, 0.25 µM bovine microtubules, 20 µM paclitaxel and 20 nM Eg5. The concentration of inhibitor was typically varied over the range of 10-200,000 nM. The reaction was monitored kinetically in an absorbance-based plate reader for a period of 10 minutes. Velocities were estimated from linear fits to the progress curves and were expressed as POC (percent of uninhibited control wells). IC$_{50}$'s were estimated from the POC data using a standard 4-parameter logistical model and compared to a control inhibitor run in each plate. In this assay, compounds of Examples 1-29 exhibited an IC$_{50}$ of less than 50 µM.

In this assay, compounds of Examples 1-29 exhibited an IC$_{50}$ of less than 1 µM.

Cell Viability Assay

The ability of the compounds of the present invention to inhibit cellular viability may be determined by the following procedure. Cells from a variety of established tumor cell lines, e.g. HeLa, were plated in Costar 3904 96-well plates, in growth medium, at a density that allowed for logarithmic growth over the period of the assay, and incubated at 37° C., 5% CO, overnight. The following day, compounds were added to the cells, at a final DMSO concentration of 0.5%. The concentration of inhibitor was typically varied over the range of 0.1-50,000 nM. Plates were then incubated as above. After a 72 to 96 hour incubation, 20 µL resazurin solution (Cell Titer Blue, Promega G8081) was added to all wells and the plates incubated for a further period of time. Viable cells convert resazurin to resorufin, a fluorescent end-product. The fluorescent signal was determined in a fluorescent plate reader at 560 nm excitation/590 nm emission. The POC (percent of uninhibited control signal) was determined for each well, and the EC$_{50}$ for inhibition of viability was determined from the inflection point of a standard 4-parameter logistical curve fitted to the values obtained. In this assay, compounds of Examples 1-29 exhibited an EC$_{50}$ of less than 50 µM.

The compounds of Examples 1-29 exhibited an EC$_{50}$ of less than 8.5 µM.

Mitotic Arrest Assay

Phosphorylation of Histone H3 on Ser10, which peaks in metaphase, is a well-established indicator of mitosis. Phosphorylation in excess of control cells is indicative of mitotic arrest. The ability of the compounds of the present invention to induce mitotic arrest was determined by the following procedure. Cells from a variety of established tumor cell lines, e.g. HeLa, were plated in Greiner 655946, 96-well, poly-D-lysine coated plates, in growth medium and incubated at 37° C., 5% CO$_2$ overnight. The following day, compounds were added to the cells at a final DMSO concentration of 0.5%. The concentration of inhibitor was typically varied over the range of 0.1-50,000 nM. Once compound was added to the cells, plates were incubated as above. After approximately 16 hours, cells were fixed with cold methanol. Plates were blocked and labeled with primary antibody to phospho-Histone H3 (Santa Cruz Biotechnologies SC-8656-R, 1

µg/mL) and to GapDH (RDI TRK-5G4-6C5). The cells were then labeled with secondary antibodies that were conjugated to fluorescent dyes emitting in the near infrared range (Molecular Probes Alexa 680, Rockland IR800) and scanned on a Licor Odyssey or Aerius. The integrated intensity of signal for phosphoHistone H3 was normalized to the signal for GapDH for each well. The POC (percent of completely inhibited control signal) was determined for each well, and the $EC_{50}$ for induction of mitotic arrest was determined from the inflection point of a standard 4-parameter logistical curve fitted to the values obtained. In this assay, compounds of Examples 1-29 exhibited an $EC_{50}$ of less than 50 µM.

Tumor Growth Inhibition

The ability of the compounds of this invention to inhibit tumor growth in vivo may be determined by the following procedure, using the HT-29 human colon tumor cell line obtained from the American Type Culture collection (ATCC). HT-29 tumor cells ($3-5 \times 10^6$, in a volume of 100 µL PBS) are implanted subcutaneously in the flank of female nude mice. Tumors are allowed to grow to 150-250 mm³ in size. The length and width of the tumors are measured with calipers, and tumor volume is calculated using the formula: volume=(length×width²)/2. The mice are then randomized into treatment groups, typically 5 to 8 per group, based on tumor volume. The mice then receive vehicle or compound on days 1, 5, 9 by IP injection. Dose is based on weight, measured the day of dosing. Tumor volume and weight are measured twice a week for the duration of the study. Mice are kept on study until tumors grow to about 1500 mm³ in size, after which the mice are euthanized by $CO_2$ inhalation. Tumor volume data are typically reported as V/V(0), where V=tumor volume on the day or measurement, and V(0)=tumor volume at day 1.

The examples presented below are intended to illustrate particular embodiments of the invention, and are not intended to limit the scope of the specification or the claims in any way.

EXAMPLES

In the examples described below, unless otherwise indicated, all temperatures are set forth in degrees Celsius. Reagents were purchased from commercial suppliers such as Aldrich Chemical Company, Lancaster, TCI or Maybridge, and were used without further purification unless otherwise indicated. Tetrahydrofuran (THF), N,N-dimethylformamide (DMF), dichloromethane (DCM), toluene, dioxane and 1,2-dichloroethane (DCE) were purchased from Aldrich in Sure seal bottles and used as received.

The reactions set forth below were typically carried out under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was carried out on a Biotage system (Manufacturer: Dyax Corporation) having a silica gel column or on a silica SepPak cartridge (Waters).

¹H-NMR spectra were recorded on a Varian instrument operating at 400 MHz. ¹H-NMR spectra were obtained as $CDCl_3$ solutions (reported in ppm), using chloroform as the reference standard (7.25 ppm). Other NMR solvents were used as needed. When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

Example 1

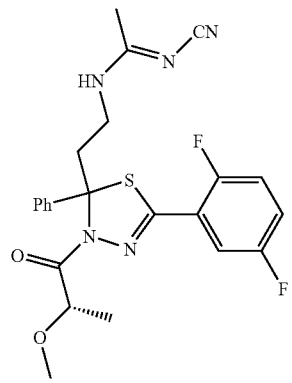

N'-cyano-N-(2-(5-(2,5-difluorophenyl)-3-((S)-2-methoxypropanoyl)-2-phenyl-2,3-dihydro-1,3,4-thiadiazol-2-yl)ethyl)acetamidine Step A: Preparation of tert-butyl 3-oxo-3-phenylpropylcarbamate: To a cooled (−78° C.) solution of 3-(tert-butoxycarbonylamino)propanoic acid (1.0 g, 5.3 mmol) in THF (53 mL) was added phenyllithium (9.9 mL, 16 mmol, 1.6 M solution in cyclohexane/ether). After warming slowly to 0° C. and then stirring for 1 hour, the reaction mixture was quenched with saturated $NH_4Cl$ (10 mL), diluted with water (70 mL) and extracted with ether. The combined organics were washed with brine (80 mL), dried over $Na_2SO_4$, filtered, and concentrated under reduced pressure. The residue was chromatographed (20% ethyl acetate in hexanes) to provide the product (0.69 g, 59%) as yellow oil.

Step B: Preparation of 2,5-difluorobenzothiohydrazide hydrochloride: To a solution of 1,4-difluorobenzene (100 g, 876 mmol) in anhydrous THF (2.0 L) at −78° C. was added a solution of sec-butyllithium (1.4 M in cyclohexane, 626 mL, 876 mmol) dropwise, maintaining the reaction temperature below −60° C. The reaction mixture was allowed to stir at −78° C. for 30 minutes, and carbon disulfide (50.2 mL, 833 mmol) was then added dropwise. The reaction mixture was allowed to warm to room temperature over 30 minutes and then stirred at room temperature for 2 hours. Water (15 mL) was then added dropwise, and the mixture was then concentrated under reduced pressure. The crude brown semi-solid residue obtained was then suspended in water (600 mL) and treated with a solution of 2-chloroacetic acid (99.4 g, 1052 mmol) and sodium bicarbonate (73.6 g, 876 mmol) in water (200 mL). The mixture was stirred at room temperature for 14 hours and then acidified to pH 4 with 50% $H_2SO_4$. The mixture was extracted with $CH_2Cl_2$, and the combined organics were washed with brine, dried over $Na_2SO_4$, filtered and concentrated to afford crude 2-(2,5-difluorophenylcarbonthioylthio)acetic acid (214 g) as red-brown syrup. This material was then suspended in a cooled (0° C.) solution of 0.5 M NaOH (1750 mL, 875 mmol), and hydrazine (54.0 mL, 1722 mmol) was then added dropwise. The reaction mixture was allowed to warm to room temperature and stir for 14 hours. The reaction mixture was then diluted with water and acidified to pH 4-5 using 1 N HCl. The mixture was then extracted with ethyl acetate and the combined organics were washed with brine, dried over Na$_2$SO$_4$, filtered and concentrated to afford crude 2,5-difluorobenzothiohydrazide as a red-brown oil (162.5 g). This oil was suspended in ether (3.5 L) and filtered. The filtered solution was then treated with 2 M HCl in ether while stirring vigorously. The mixture was stirred at room temperature for 15 minutes. The precipitate that formed was isolated by filtration and dried under vacuum to afford 2,5-difluorobenzothiohydrazide hydrochloride (50 g, 26%) as a yellow solid.

Step C: Preparation of tert-butyl 2-(5-(2,5-difluorophenyl)-2-phenyl-2,3-dihydro-1,3,4-thiadiazol-2-yl)ethylcarbamate: To a cooled (0° C.) solution of tert-butyl 3-oxo-3-phenylpropylcarbamate (0.68 g, 2.73 mmol) and 2,5-difluorobenzothiohydrazide hydrochloride (0.613 g, 2.73 mmol) in EtOH (27 mL) was added triethylamine (0.57 mL, 4.09 mmol). After stirring at room temperature for 8 hours, the mixture was heated to 65° C. for 16 hours. The mixture was concentrated under reduced pressure and the residue was dissolved in ethyl acetate (100 mL). The solution was washed with water and brine (40 mL), dried over Na$_2$SO$_4$, filtered and concentrated under reduced pressure. The residue was chromatographed (30% ethyl acetate in hexanes) to provide the crude product as a brown syrup which was used directly in the next step.

Step D: Preparation of (2S)-1-(2-(2-aminoethyl)-5-(2,5-difluorophenyl)-2-phenyl-1,3,4-thiadiazol-3(2H)-yl)-2-methoxypropan-1-one hydrochloride: To a solution of (S)-2-methoxypropanoic acid (0.186 g, 1.79 mmol) and diisopropylethylamine (0.415 mL, 2.38 mmol) in DMF (10 mL) was added PyBOP (0.930 g, 1.79 mmol). After stirring for 5 minutes, a solution of tert-butyl 2-(5-(2,5-difluorophenyl)-2-phenyl-2,3-dihydro-1,3,4-thiadiazol-2-yl)ethylcarbamate (0.500 g, 1.19 mmol) in DMF (2 mL) was added. After stirring at room temperature for 17 hours, the mixture was treated with saturated NaHCO$_3$ and extracted with ethyl acetate. The combined organics were washed with water and brine (50 mL), dried over Na$_2$SO$_4$ and concentrated under reduced pressure. The residue was chromatographed (4:1 to 2:1 hexanes/ethyl acetate) to provide the Boc-protected product (263 mg, 44%) as a mixture of diastereomers. To a cooled (0° C.) solution of this material in dioxide (6 mL) was added HCl (6.0 mL, 30.0 mmol, 5 M solution in dioxane). After stirring at room temperature for 3 hours, the mixture was concentrated under reduced pressure. The residue was triturated with ether, filtered and dried under vacuum to provide the product (263 mg, 94%) as a yellow powder.

Step E: Preparation of ethyl N-cyanoacetimidate: A mixture of cyanamide (1.00 g, 23.8 mmol) and 1,1,1-triethoxyethane (4.34 mL, 23.8 mmol) in acetic anhydride (4.49 mL, 47.6 mmol) was heated to 100° C. in a distillation apparatus. After the volume of distillate diminished, the mixture was heated to 140° C., distilling most of the acetic acid. The residue was distilled under vacuum to afford the product (0.80 g, 30%) as colorless liquid (b.p. 90° C. at 20 mm).

Step F: Preparation of N'-cyano-N-(2-(5-(2,5-difluorophenyl)-3-((S-2-methoxypropanoyl)-2-phenyl-2,3-dihydro-1,3,4-thiadiazol-2-yl)ethyl)acetamidine: To a solution of ethyl N-cyanoacetimidate (0.025 g, 0.22 mmol) and (2S)—(2-(2-aminoethyl)-5-(2,5-difluorophenyl)-2-phenyl-1,3,4-thiadiazol-3(2H)-yl)-2-methoxypropan-1-one hydrochloride (0.018 g, 0.038 mmol) in EtOH (0.3 mL) was added diisopropylethylamine (0.033 mL, 0.19 mmol). After stirring at room temperature for 14 hours, the mixture was diluted with 10% Na$_2$CO$_3$ (30 mL) and extracted with dichloromethane. The combined organics were dried over Na$_2$SO$_4$, filtered and concentrated under reduced pressure. The residue was chromatographed (3% MeOH in dichloromethane) to provide the product as a mixture of diastereomers (13.0 mg, 73% yield). MS ESI (+) m/z 472 (M+1) detected; $^1$H NMR (400 MHz, CDCl$_3$) δ 7.51 (m, 2H), 7.37 (m, 6H), 7.33 (m, 4H), 7.16 (m, 4H), 6.93 (br. t, 1H, J=4.7 Hz), 6.73 (br. t, 1H, J=4.7 Hz), 4.73 (m, 2H), 4.00 (m, 2H), 3.45-3.29 (m, 9H), 3.21 (m, 1H), 2.82 (m, 1H), 2.75 (m, 1H), 2.16 (s, 3H), 2.15 (s, 3H), 1.46 (d, 3H, J=6.3 Hz), 1.43 (d, 3H, J=7.0 Hz).

Example 2

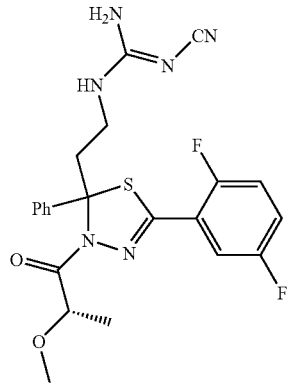

2-Cyano-1-(2-(5-(2,5-difluorophenyl)-3-((S)-2-methoxypropanoyl)-2-phenyl-2,3-dihydro-1,3,4-thiadiazol-2-yl)ethyl)guanidine To a solution of (2S)-1-(2-(2-aminoethyl)-5-(2,5-difluorophenyl)-2-phenyl-1,3,4-thiadiazol-3(2H)-yl)-2-methoxypropan-1-one (23.4 mg, 0.0489 mmol) in isopropanol (1 mL) was added triethylamine (0.027 mL, 0.196 mmol) and diphenyl-N-cyanocarbonimidate (35.0 mg, 0.147 mmol). After stirring at room temperature for 1 hour, ammonia (3 mL, 7M solution in methanol) was added. The reaction vessel was sealed and heated to 60° C. for 2 hours. The mixture was concentrated under reduced pressure, and the residue was chromatographed (3% methanol in dichloromethane) to provide the product as a white solid and as a mixture of diastereomers (20.6 mg, 83% yield). MS APCI (+) m/z 473 (M+1) detected; $^1$H NMR (400 MHz, CD$_3$OD) δ 7.67-7.61 (m, 2H), 7.51-7.44 (m, 4H), 7.42-7.36 (m, 4H), 7.34-7.28 (m, 6H), 4.83-4.77 (m, 2H), 3.73-3.65 (m, 2H), 3.42 (s, 3H), 3.44-3.37 (m, 2H), 3.35-3.29 (m, 2H), 3.28 (s, 3H), 2.84-2.73 (m, 2H), 1.49 (d, 3H, J=7.1 Hz), 1.43 (d, 3H, J=7.1 Hz).

Example 3

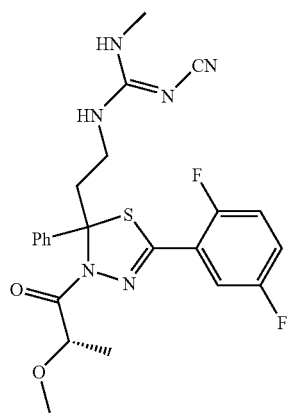

2-Cyano-1-(2-(5-(2,5-difluorophenyl)-3((S)-2-methoxypropanoyl)-2-phenyl-2,3-dihydro-1,3,4-thiadiazol-2-yl)ethyl)-3-methylguanidine Prepared according to the method of Example 2, using methanamine in place of ammonia, to afford the product as a mixture of diastereomers. MS ESI (+) m/z 487 (M+1) detected; $^1$H NMR (400 MHz, CD$_3$OD) δ 7.68-7.62 (m, 2H), 7.52-7.44 (m, 4H), 7.42-7.36 (m, 4H), 7.34-7.27 (m, 6H), 4.83-4.77 (m, 2H), 3.80-3.77 (m, 2H), 3.51-3.44 (m, 2H), 3.43 (s, 3H), 3.40-3.30 (m, 2H), 3.28 (s, 3H), 2.88-2.80 (m, 2H), 2.79 (s, 3M), 2.78 (s, 3H), 1.50 (d, 3H, J=7.1 Hz), 1.44 (d, 3H, J=7.1 Hz).

Example 4

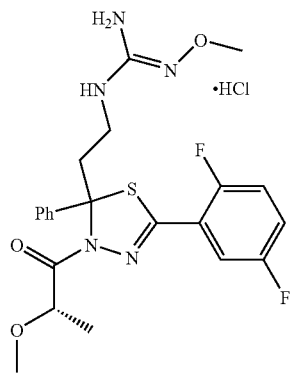

1-(2-(5-(2,5-Difluorophenyl)-3-((S)-2-methoxypropanoyl)-2-phenyl-2,3-dihydro-1,3,4-thiadiazol-2-yl)ethyl)-2-methoxyguanidine hydrochloride Step A: Preparation of (2-(5-(2,5-difluorophenyl)-3-((S)-2-methoxypropanoyl)-2-phenyl-2,3-dihydro-1,3,4-thiadiazol-2-yl)ethyl)cyanamide: To a solution of (2S)-1-(2-(2-aminoethyl)-5-(2,5-difluorophenyl)-2-phenyl-1,3,4-thiadiazol-3(2H)-yl)-2-methoxypropan-1-one (34.5 mg, 0.0721 mmol) and cyanogen bromide (9.9 mg, 0.0938 mmol) in dichloromethane (1 mL) was slowly added triethylamine (25.5 mg, 0.252 mmol). After stirring at room temperature for 1 hour, the mixture was concentrated under reduced pressure to provide the crude product that was used without further purification.

Step B: Preparation of 1-(2-(2-(2,5-difluorophenyl)-3-((S)-2-methoxypropanoyl)-2-phenyl-2,3-dihydro-1,3,4-thiadiazol-2-yl)ethyl)-2-methoxyguanidine hydrochloride: To a solution of crude (2-(5-(2,5-difluorophenyl)-3-((S)-2-methoxypropanoyl)-2-phenyl-2,3-dihydro-1,3,4-thiadiazol-2-yl)ethyl)cyanamide (31 mg, 0.072 mmol) and methoxyamine hydrochloride (151 mg, 1.80 mol) in ethanol (3 mL) was added triethylamine (182 mg, 1.80 mmol). After heating to 70° C. in a sealed vessel for 16 hours, additional methoxyamine hydrochloride (151 mg, 1.80 mol) and triethylamine (182 mg, 1.80 mmol) was added, and the reaction mixture was heated to 70° C. in a sealed vessel for an additional 24 hours. The mixture was cooled to room temperature and diluted with ethyl acetate. The salts were removed by filtration. The filtrate was concentrated under reduced pressure, and the residue was chromatographed (4% methanol in dichloromethane with 0.5% NH$_4$OH), and the isolated material was treated with excess HCl in MeOH then concentrated to afford the product as a mixture of diastereomers (23 mg, 62% yield). MS APCI (+) m/z 478 (M+1) detected; $^1$H NMR (400 MHz, CD$_3$OD) δ 7.69-7.64 (m, 2H), 7.50-7.38 (m, 8H), 7.37-7.29 (m, 6H), 4.83-4.78 (m, 2H), 3.80-3.67 (m, 2H), 3.73 (s, 6H), 3.54-3.45 (m, 2H), 3.45-3.33 (m, 2H), 3.39 (s, 3H), 3.31 (s, 3H), 3.04-2.92 (m, 2H), 1.49 (d, 3H, J=7.1 Hz), 1.45 (d, 3H, J=7.1 Hz).

Example 5

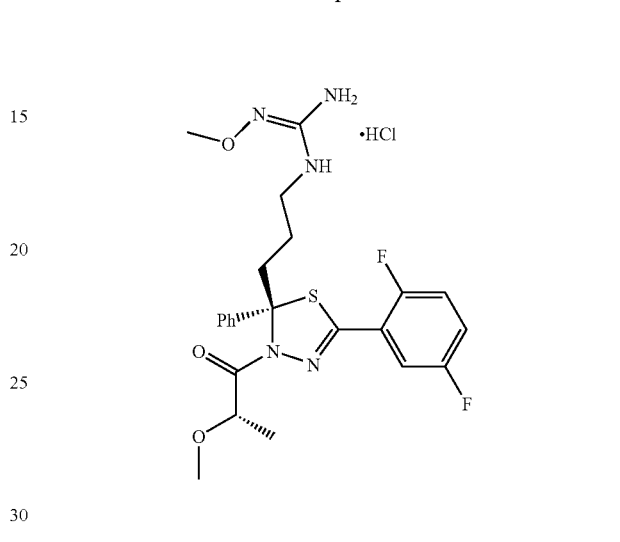

1-(3-((S)-5-(2,5-difluorophenyl)-3-((S)-2-methoxypropanoyl)-2-phenyl-2,3-dihydro-1,3,4-thiadiazol-2-yl)propyl)-2-methoxyguanidine Hydrochloride Step A: Preparation of 4-azido-1-phenylbutan-1-one: To a solution of 4-chloro-1-phenylbutan-1-one (26.4 mL, 164 mmol) in DMSO (200 mL) was added sodium azide (12.8 g, 197 mmol). The solution was warmed to 55° C. and stirred for 16 hours. The cooled mixture was then treated with water and extracted with ether. The combined organics were washed with water and brine, then dried over MgSO$_4$ and concentrated to provide the product as an orange oil (30.7 g, 99%).

Step B: Preparation of 2-(3-azidopropyl)-5-(2,5-difluorophenyl)-2-phenyl-2,3-dihydro-1,3,4-thiadiazole: To a solution of 2,5-difluorobenzothiohydrazide (Example 1, Steps A and B; 1.5 g, 7.97 mmol) in EtOH/dichloromethane (3:1, 16 mL) was added 4-azido-1-phenylbutan-1-one (1.36 g, 7.17 mmol). After stirring at room temperature for 16 hours, acetic acid (2 drops) was added, and the mixture was stirred for another 16 hours. The reaction mixture was then concentrated under reduced pressure and chromatographed (9:1 hexanes/ethyl acetate) to provide the product (1.41 g, 41%) as a bright yellow syrup.

Step C: Preparation of (S)-1-((S)-2-(3-azidopropyl)-5-(2,5-difluorophenyl)-2-phenyl-1,3,4-thiadiazol-3(2H)-yl)-2-(t-butyldiphenylsilyloxy)propan-1-one and (S)-1-((R)-2-(3-azidopropyl)-5-(2,5-difluorophenyl)-2-phenyl-1,3,4-thiadiazol-3(2H)-yl)-2-(t-butyldiphenylsilyloxy)propan-1-one: To a solution of (S)-2-(t-butyldiphenylsilyloxy) propanoic acid (339 mg, 1.09 mmol) in acetonitrile (6 mL) was added HATU (550 mg, 1.45 mmol) followed by DIEA (0.378 mL, 2.17 mmol). After stirring at room temperature for 15 minutes, a solution of 2-(3-azidopropyl)-5-(2,5-difluorophenyl)-2-phenyl-2,3-dihydro-1,3,4-thiadiazole (260 mg, 0.72 mmol) in acetonitrile (4 mL) was added. After stirring at room temperature for 16 hours, the mixture was concentrated under reduced pressure and partitioned between saturated NaHCO₃ (50 mL) and ethyl acetate (50 mL). The aqueous layer was extracted with ethyl acetate, and the combined organic phases were washed with brine (20 mL), dried over Na₂SO₄, filtered, and concentrated under reduced pressure. The brown oil was chromatographed (9:1 hexanes/ethyl acetate) to provide the less polar diastereomer, (S)-1-((S)-2-(3-azidopropyl)-5-(2,5-difluorophenyl)-2-phenyl-1,3,4-thiadiazol-3(2H)-yl)-2-(t-butyldiphenylsilyloxy)propan-1-one (121 mg) and the more polar diastereomer, (S)-1-((R)-2-(3-azidopropyl)-5-(2,5-difluorophenyl)-2-phenyl-1,3,4-thiadiazol-3(2H)-yl)-2-(t-butyldiphenylsilyloxy)propan-1-one (175 mg) as pale yellow oils. Absolute stereochemistry was assigned by examination of a protein inhibitor co-crystal structure of Eg5 and (S)-1-((S)-2-(3-aminopropyl)-5-(2,5-difluorophenyl)-2-phenyl-1,3,4-thiadiazol-3(2H)-yl)-2-methoxypropan-1-one.

Step D: Preparation of (S)-1-((S)-2-(3-azidopropyl)-5-(2,5-difluorophenyl)-2-phenyl-1,3,4-thiadiazol-3(2H)-yl)-2-hydroxypropan-1-one: To a solution of (S)-1-((S)-2-(3-azidopropyl)-5-(2,5-difluorophenyl)-2-phenyl-1,3,4-thiadiazol-3(2H)-yl)-2-(t-butyldiphenylsilyloxy)propan-1-one (121 mg, 0.18 mmol) in THF (5 mL) at 0° C. was added TBAF (0.31 mL, 1M, 0.31 mmol). After stirring at 0° C. for 1 hour and at room temperature for 1 hour, the mixture was treated with saturated NaHCO₃ and extracted with ethyl acetate. The combined organics were washed with brine, dried over Na₂SO₄, filtered, and concentrated. The brown oil was chromatographed (4:1 hexanes/ethyl acetate) to provide the product (4.1 mg, 53%) as a pale yellow oil.

Step E: Preparation of (S)-1-((S)-2-(3-azidopropyl)-5-(2,5-difluorophenyl)-2-phenyl-1,3,4-thiadiazol-3(2H)-yl)-2-methoxypropan-1-one: To a solution of (S)-1-((S)-2-(3-azidopropyl)-5-(2,5-difluorophenyl)-2-phenyl-1,3,4-thiadiazol-3(2H)-yl)-2-hydroxypropan-1-one (41 mg, 0.095 mmol) in DMF (2 mL) at 0° C. was added methyl iodide (50 μL, 0.48 mmol) followed by sodium hydride (10 mg, 60%). After stirring at 0° C. for 30 minutes and room temperature for 3 hours, the mixture was treated with saturated NH₄Cl (20 mL) and extracted with ethyl acetate. The combined organic phases were washed with water and brine, dried over Na₂SO₄, filtered, and concentrated under reduced pressure to provide the product (40 mg, 940%) as a yellow oil.

Step F: Preparation of (S)-1-((S)-2-(3-aminopropyl)-5-(2,5-difluorophenyl)-2-phenyl-1,3,4-thiadiazol-3(2H)-yl)-2-methoxypropan-1-one: To a suspension of (S)-1-((S)-2-(3-azidopropyl)-5-(2,5-difluorophenyl)-2-phenyl-1,3,4-thiadiazol-3(2H)-yl)-2-hydroxypropan-1-one (102 mg, 0.23 mmol) in MeOH (2.2 mL) was added conc. HCl (57 μL, 0.69 mmol) followed by 10% Pd/C (10 mg, wet, Degussa type). After stirring under a H₂ atmosphere for 1 hour, the mixture was filtered and concentrated under reduced pressure. The colorless glass was triturated with diethyl ether and filtered to provide the di-HCl salt product as a white solid (89 mg, 79%). MS ESI (+) m/z 420 (M+1) detected; ¹H NMR (400 MHz, CDCl₃) δ 7.52 (m, 1H), 7.45 (m, 2H), 7.35 (m, 2H), 7.28 (m, 1H), 7.13 (m, 2H), 4.70 (m, 1H), 3.40 (s, 3H), 3.27 (m, 1H), 2.88 (m, 2H), 2.43 (m, 1H), 1.96 (m, 1H), 1.57 (m, 1H), 1.45 (d, 3H, J=7 Hz). Absolute stereochemistry assigned by examination of a protein inhibitor co-crystal structure of Eg5 and (S)-1-((S)-2-(3-aminopropyl)-5-(2,5-difluorophenyl)-2-phenyl-1,3,4-thiadiazol-3(2H)-yl)-2-methoxypropan-1-one.

Step G: Preparation of 1-(3-((S)-5-(2,5-difluorophenyl)-3-((S)-2-methoxypropanoyl)-2-phenyl-2,3-dihydro-1,3,4-thiadiazol-2-yl)propyl)-2-methoxyguanidine hydrochloride: To a solution of (S)-1-((S)-2-(3-aminopropyl)-5-(2,5-difluorophenyl)-2-phenyl-1,3,4-thiadiazol-3(2H)-yl)-2-methoxypropan-1-one (Example 5, Steps A-C, 52.1 mg, 0.106 mmol) and cyanogen bromide (13.4 mg, 0.127 mmol) in dichloromethane (1 mL) was slowly added triethylamine (35.3 mg, 0.349 mmol). After stirring for 20 minutes at room temperature, the mixture was concentrated under reduced pressure and dissolved in ethanol (2 mL). To this solution was added methoxyamine hydrochloride (600 mg, 7.18 mmol) and triethylamine (642 mg, 6.35 mmol). The reaction vessel was sealed and heated to 70° C. for 24 hours. The mixture was concentrated under reduced pressure and dissolved in ethyl acetate. The precipitate was removed by filtration and the filtrate was concentrated under reduced pressure. The residue was chromatographed (3% methanol in dichloromethane with 0.5% NH₄OH), and the isolated material was treated with excess HCl in MeOH then concentrated to afford the product as a white solid (7.3 mg, 13% yield). MS APCI (+) m/z 492 (M+1) detected; ¹H NMR (400 MHz, CD₃OD) δ 7.65-7.60 (m, 1H), 7.47-7.45 (m, 2H), 7.42-7.37 (m, 2H), 7.35-7.29 (m, 3H), 4.79 (q, 1H, J=7.0 Hz), 3.73 (s, 3H), 3.45-3.37 (m, 2H), 3.36 (s, 3H), 3.28-3.19 (m, 1H), 2.60-2.51 (m, 1H), 2.19-2.08 (m, 1H), 1.71-1.60 (m, 1H), 1.43 (d, 3H, J=7.0 Hz).

Example 6

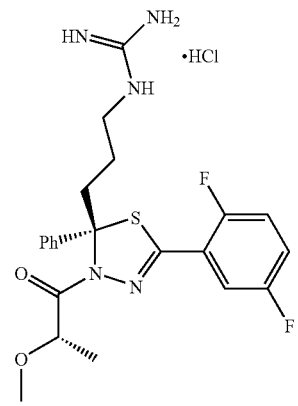

1-(3-((S)-5-(2,5-difluorophenyl)-3-((S)-2-methoxypropanoyl)-2-phenyl-2,3-dihydro-1,3,4-thiadiazol-2-yl)propyl)guanidine Hydrochloride To a solution of (S)-1-((S)-2-(3-aminopropyl)-5-(2,5-difluorophenyl)-2-phenyl-1,3,4-thiadiazol-3(2H)-yl)-2-methoxypropan-1-one (Example 5, Step F; 58 mg, 0.118 mmol) and triethylamine (29.8 mg, 0.294 mmol) in THF was added N,N'-di-Boc-1H-pyrazole-1-carboxamidine (45 mg, 0.145 mmol). After stirring at room temperature for 2 hours, the mixture was concentrated under reduced pressure. The residue was chromatographed (15% ethyl acetate in hexanes) to provide the Boc-protected product (60 mg, 77%) as white foam. To 20 mg of this material was added HCl in dioxane (1 mL of a 4M solution). After stirring at room temperature for 2 days, the mixture was concentrated and triturated with ether to provide the product as a white loam (10 mg, 63% yield). MS ESI (+) m/z 462 (M+1) detected, ¹H NMR (400 MHz, CD₃OD) δ 7.66-7.60, (m, 1H), 7.51-7.44 (m, 2H), 7.43-7.36 (m, 2H), 7.35-7.28 (m, 3H), 4.83-4.76 (m, 1H), 3.40-3.34 (m, 1H), 3.36 (s, 3H), 3.29-3.18 (m, 2H), 2.62-2.52 (m, 1H), 2.17-2.05 (m, 1H), 1.70-1.59 (m, 1H), 1.43 (d, 3H, J=6.0 Hz).

Example 7

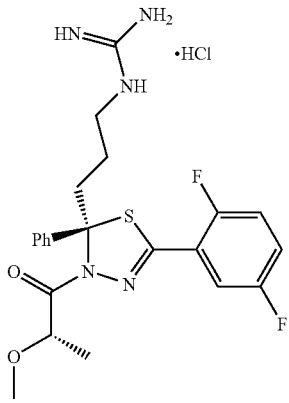

1-(3-((R)-5-(2,5-difluorophenyl)-3-((S)-2-methoxypropanoyl)-2-phenyl-2,3-dihydro-1,3,4-thiadiazol-2-yl)propyl)guanidino Hydrochloride Step A: Preparation of (S)-1-((R)-2-(3-aminopropyl)-5-(2,5-difluorophenyl)-2-phenyl-1,3,4-thiadiazol-3(2H)-yl)-2-methoxypropan-1-one: Prepared as described in Example 5, Steps A-G, using (S)-1-((R)-2-(3-azidopropyl)-5-(2,5-difluorophenyl)-1)-2-phenyl-1,3,4-thiadiazol-3(2H)-yl)-2-(tert-butyldiphenylsilyloxy)propan-1-one from Step C. MS ESI (+) m/z 420 (M+1) detected; $^1$H NMR (400 MHz, CDCl$_3$) δ 7.51 (m, 1H), 7.44 (m, 2H), 7.36 (m, 2H), 7.29 (m, 1H), 7.12 (m, 2H), 4.71 (q, 1H, J=6 Hz), 3.32 (s, 3H), 3.23 (m, 1H), 2.84 (m, 2H), 2.43 (m, 1H), 1.93 (m, 1H), 1.50 (d, 3H, J=6 Hz), 1.44 (m, 2H), 1.34 (m, 1H). Stereochemistry was assigned by inference from (S)-1-((S)-2-(3-aminopropyl)-5-(2,5-difluorophenyl)-2-phenyl-1,3,4-thiadiazol-3(2H)-yl)-2-methoxypropan-1-one.

Step B: Preparation of 1-(3-((R)-5-(2,5-difluorophenyl)-3-((S)-2-methoxypropanoyl)-2-phenyl-2,3-dihydro-1,3,4-thiadiazol-2-yl)propyl)guanidine hydrochloride: Prepared according to the method of Example 6, using (S)-1-((R)-2-(3-aminopropyl)-5-(2,5-difluorophenyl)-2-phenyl-1,3,4-thiadiazol-3(2H)-yl)-2-methoxypropan-1-one (Example 5, Steps A-F) in place of (S)-1-((S)-2-(3-aminopropyl)-5-(2,5-difluorophenyl)-2-phenyl-1,3,4-thiadiazol-3(2H)-yl)-2-methoxypropan-1-one. MS ESI (+) m/z 462 (M+1) detected; $^1$H NMR (400 MHz, CD$_3$OD) δ 7.65-7.60 (m, 1H), 7.53-7.47 (m, 2H), 7.43-7.37 (m, 2H), 7.35-7.27 (m, 3H), 4.85-4.79 (m, 1H), 3.39-3.30 (m, 2H), 3.29 (s, 3H), 3.25-3.18 (m, 1H), 2.63-2.53 (m, 1H), 2.13-2.02 (m, 1H), 1.62-1.51 (m, 1H), 1.46 (d, 3H, J=6.6 Hz).

Example 8

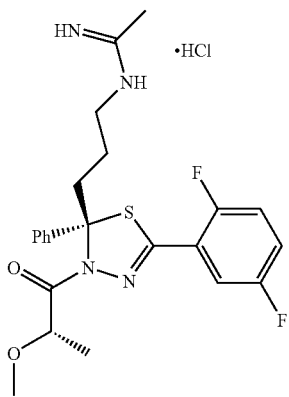

N-(3-((S)-5-(2,5-difluorophenyl)-3-((S)-2-methoxypropanoyl)-2-phenyl-2,3-dihydro-1,3,4-thiadiazol-2-yl)propyl)acetamidine Hydrochloride To a solution of (S)-1-((S)-2-(3-aminopropyl)-5-(2,5-difluorophenyl)-2-phenyl-1,3,4-thiadiazol-3(2H)-yl)-2-methoxypropan-1-one (Example 5, Steps A-F; 57.5 mg, 0.117 mmol) and methyl acetimidate hydrochloride (192 mg, 1.75 mmol) in methanol was added triethylamine (355 mg, 3.51 mmol). After heating at 50° C. for 16 hours, the mixture was concentrated under reduced pressure. The residue was chromatographed (15:85:1 MeOH/dichloromethane/NH$_4$OH), and the isolated material %% as treated with excess HCl in MeOH then concentrated to afford the product. MS ESI (+) m/z 461 (M+1) detected. $^1$H NMR (400 MHz, CD$_3$OD) δ 7.65-7.60 (m, 1H), 7.49-7.45 (m, 2H), 7.42-7.38 (m, 2H), 7.35-7.29 (m, 3H), 4.80 (q, 1H, J=7.1 Hz), 3.50-3.40 (m, 2H), 3.36 (s, 3H), 3.28-3.19 (m, 1H), 2.65-2.57 (m, 1H), 2.22 (s, 3H), 2.21-2.12 (m, 1H), 1.75-1.64 (m, 1H), 1.44 (d, 3H, J=7.1 Hz).

Example 9

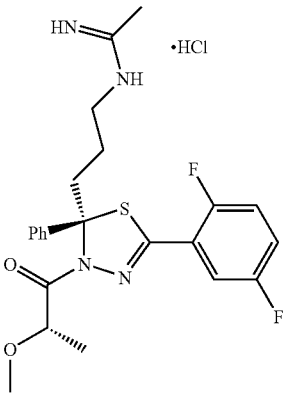

N-3-((R)-5-(2,5-Difluorophenyl)-3-((S)-2-methoxypropanoyl)-2-phenyl-2,3-dihydro-1,3,4-thiadiazol-2-yl)propyl)acetamidine Hydrochloride Prepared according to the method of Example 8, using (S)-1-((R)-2-(3-aminopropyl)-5-(2,5-difluorophenyl)-2-phenyl-1,3,4-thiadiazol-3(2H)-yl)-2-methoxypropan-1-one (Example 7, Step A) in place of (S)-1-((S)-2-(3-aminopropyl)-5-(2,5-difluorophenyl)-2-phenyl-1,3,4-thiadiazol-3(2H)-yl)-2-methoxypropan-1-one. MS ESI (+) m/z 461 (M+1) detected: $^1$H NMR (400 MHz, CD$_3$OD) δ 7.66-7.60 (m, 1H), 7.53-7.48 (m, 2H), 7.44-7.38 (m, 2H), 7.35-7.28 (m, 3H), 4.83 (q, 1H, J=6.9 Hz), 3.51-3.37 (m 2H), 3.29 (s, 3H), 3.26-3.16 (m, 1H), 2.69-2.60 (m, 1H), 2.24 (s, 3H), 2.21-2.09 (m, 1H), 1.68-1.57 (m, 1H), 1.47 (d, 3H, J=6.9 Hz).

Example 10

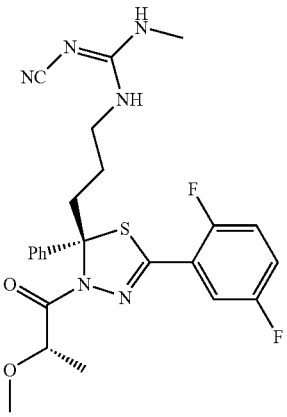

2-Cyano-1-(3-((S)-5-(2,5-difluorophenyl)-3-((S)-2-methoxypropanoyl)-2-phenyl-2,3-dihydro-1,3,4-thiadiazol-2-yl)propyl)-3-methylguanidine Prepared according to the method of Example 2, using methanamine in place of ammonia and (S)-1-((S)-2-(3-aminopropyl)-5-(2,5-difluorophenyl)-2-phenyl-1,3,4-thiadiazol-3(2H)-yl)-2-methoxypropan-1-one (Example 5, Steps A-F) in place of (2S)-1-(2-(2-aminoethyl)-5-(2,5-difluorophenyl)-2-phenyl-1,3,4-thiadiazol-3(2H)-yl)-2-methoxypropan-1-one. MS ESI (+) m/z 501 (M+1) detected; $^1$H NMR (400 MHz, CD$_3$OD) δ 7.64-7.60 (m, 1H), 7.49-7.45 (m, 2H), 7.42-7.36 (m, 2H), 7.34-7.27 (m, 3H), 4.82-4.75 (m, 1H), 3.50-3.38 (m, 1H), 3.37 (s, 3H), 3.27-3.12 (m, 1H), 2.81 (d, 3H, J=24.7 Hz), 2.60-2.42 (m, 1H), 2.20-2.08 (m, 1H), 2.17-2.07 (m, 1H), 1.71-1.59 (m, 1H), 1.43 (d, 3H, J=6.8 Hz).

Example 11

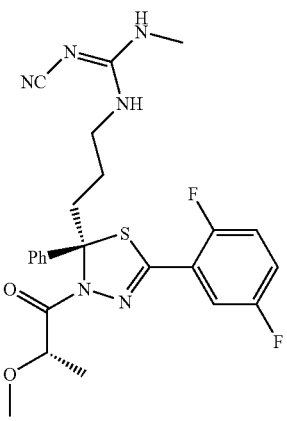

2-Cyano-1-(3-((R)-5-(2,5-difluorophenyl)-3-((S)-2-methoxypropanoyl)-2-phenyl-2,3-dihydro-1,3,4-thiadiazol-2-yl)propyl-3-methylguanidine Prepared according to the method of Example 2, using methanamine in place of ammonia and (S)-1-((R)-2-(3-aminopropyl)-5-(2,5-difluorophenyl)-2-phenyl-1,3,4-thiadiazol-3(2H)-yl)-2-methoxypropan-1-one (Example 7, Step A) in place of (2S)-1-(2-(2-aminoethyl)-5-(2,5-difluorophenyl)-2-phenyl-1,3,4-thiadiazol-3(2H)-yl)-2-methoxypropan-1-one. MS ESI (+) m/z 501 (M+1) detected; $^1$H NMR (400 MHz, CD$_3$OD) δ 7.64-7.59 (m, 1H), 7.52-7.48 (m, 2H), 7.42-7.36 (m, 2H), 7.33-7.27 (m, 3H), 4.80 (q, 1H, J=7.0 Hz), 3.43-3.28 (m, 2H), 3.27 (s, 3H), 3.21-3.12 (m, 1H), 2.78 (s, 3H), 2.55-2.46 (m, 1H), 2.06-1.95 (m, 1H), 1.64-1.53 (m, 1H), 1.46 (d, 3H, J=7.0 Hz).

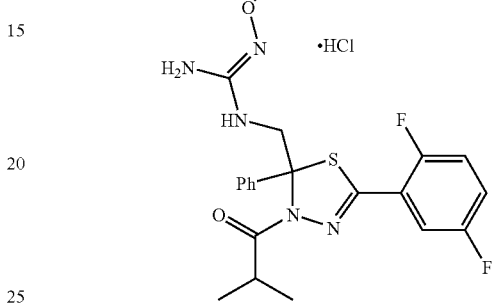

1-((5-(2,5-Difluorophenyl)-3-isobutyryl-2-phenyl-2,3-dihydro-1,3,4-thiadiazol-2-yl)methyl)-2-methoxyguanidine Hydrochloride Step A: Preparation of 1-methoxy-2,3-di-tert-butoxycarbonyl guanidine: To a solution of N,N'-di-Boc-1H-pyrazole-1-carboxamidine (450 mg, 1.45 mmol) and methoxyamine hydrochloride (151 mg, 1.81 mmol) in THF (3 mL) aid methanol (3 mL) was slowly added triethylamine (183 mg, 1.81 mmol). After stirring at room temperature for 64 hours, the reaction mixture was concentrated under reduced pressure and diluted with ethyl acetate. The salts were removed by filtration. The filtrate was concentrated under reduced pressure and triturated with ether to provide the crude product that was used without further purification.

Step B: Preparation of tert-butyl N-(tert-butoxycarbonyl)-N'-methoxycarbamimidoyl(2-oxo-2-phenylethyl)carbamate: To a solution of crude 1-methoxy-2,3-di-tert-butoxycarbonyl guanidine (420 mg, 1.45 mmol) and bromoacetophenone (361 mg, 1.81 mmol) and potassium hydroxide (163 mg, 2.60 mmol) in dichloromethane and water (15 mL, 1:1) was added tetrabutylammonium iodide (54 mg, 0.145 mmol). After stirring at room temperature for 16 hours, the organic layer separated, dried (Na$_2$SO$_4$), and filtered. The filtrate was concentrated under reduced pressure, and the residue was chromatographed (10%-25% ethyl acetate in hexanes) to provide the product in 60% purity, along with 1-dimethoxy-2,3-di-tert-butoxycarbonyl guanidine starting material.

Step C: Preparation of tert-butyl N-(tert-butoxycarbonyl)-N'-methoxycarbamimidoyl((5-(2,5-difluorophenyl)-2-phenyl-2,3-dihydro-1,4-thiadiazol-2-yl)methyl) carbamate: To a solution of tert-butyl N-(tert-butoxycarbonyl)-N'-methoxycarbamimidoyl(2-oxo-2-phenylethyl)carbamate (220 mg, 60% pure, 0.319 mmol) in ethanol (1 mL) was added 2,5-difluorobenzothiohydrazide (40 mg, 0.213 mmol). After stirring at room temperature for 16 hours, the mixture was concentrated under reduced pressure. The residue was chromatographed (3%-5% ethyl acetate in hexanes) and solidified under high vacuum to provide the product (68.5 mg, 56% yield) as a white solid.

Step D: Preparation of 1-((5-(2,5-difluorophenyl)-3-isobutyryl-2-phenyl-2,3-dihydro-1,3,4-thiadiazol-2-yl)methyl)-2-methoxyguanidine hydrochloride: To a solution of tert-butyl N-(tert-butoxycarbonyl)-N'-methoxycarbamimidoyl((5-(2,3-difluorophenyl)-2-phenyl-2,3-dihydro-1,3,4-thiadiazol-2-yl)ethyl)carbamate (25.3 mg, 0.044 mmol) in dichloromethane (1 mL) was added triethylamine (17.7 mg, 0.175 mmol) followed by isobutyryl chloride (14 mg, 0.131 mmol). After stirring at room temperature for 3 hours, the reaction mixture was concentrated under reduced pressure. The residue was chromatographed (10% ethyl acetate in hexanes) to provide the Boc-protected product (23 mg, 81%) as a white foam. To this product was added HCl (1 mL of a 2M solution in dioxane). After stirring at room temperature for 16 hours, the mixture was concentrated under reduced pressure. The residue was triturated with ether to provide the product as a white powder and as a mixture of diastereomers (16.3 mg, 94% yield). MS ESI (+) m/z 448 (M+1) detected; ¹H NMR (400 MHz, CDCl₃) δ 7.56-7.50 (m, 1H), 7.41-7.28 (m, 5H), 7.14-7.05 (m, 2H), 4.52-4.45 (m 1H), 3.65-3.52 (m, 1H), 3.57 (br. s, 3H), 3.48 (q, 1H, J=6.2 Hz), 1.28 (d, 3H, J=6.2 Hz), 1.22 (d, 3H, J=6.2 Hz).

Example 13

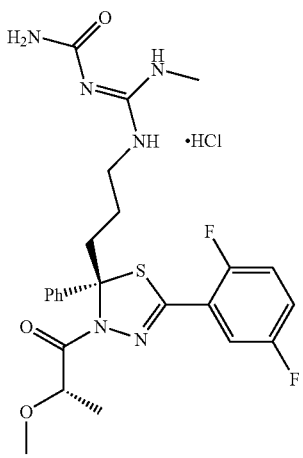

1-((3-((S)-5-(2,5-Difluorophenyl)-3-((S)-2-methoxypropanoyl)-2-phenyl-2,3-dihydro-1,3,4-thiadiazol-2-yl)propylamino)(methylamino)methylene)urea Hydrochloride To a solution of 2-cyano-1-(3-((S)-5-(2,5-difluorophenyl)-3-((S)-2-methoxypropanoyl)-2-phenyl-2,3-dihydro-1,3,4-thiadiazol-2-yl)propyl)-3-methylguanidine (Example 10; 130 mg, 0.26 mmol) in methanol (3 mL) was added HCl (0.65 mL of a 4 M solution in dioxane) and water (0.05 mL, 2.6 mmol). After stirring at room temperature for 16 hours, the mixture was concentrated under reduced pressure. The residue was triturated with ether to provide the product as a pale pink solid (135 mg, 94% yield). MS ESI (+) m/z 541 (M+Na) detected: ¹H NMR (400 MHz, CD₃OD) δ 7.66-7.61 (m, 1H), 7.49-7.46 (m, 2H), 7.42-7.37 (m, 2H), 7.34-7.28 (m, 3H), 4.79 (q, 1H, J=6.4 Hz), 3.53-3.43 (m, 2H), 3.36 (s, 3H), 3.30-3.20 (m, 1H), 2.95 (s, 3H), 2.67-2.55 (m, 1H), 2.23-2.11 (m, 1H), 1.75-1.63 (m, 1H), 1.43 (d, 3H, J=6.4 Hz).

Example 14

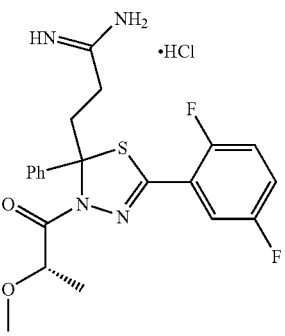

3-(5-(2,5-Difluorophenyl)-3-((S)-2-methoxypropanoyl)-2-phenyl-2,3-dihydro-1,3,4-thiadiazol-2-yl) propanimidamide Hydrochloride Step A: Preparation of 4-oxo-4-phenylbutanenitrile: To a solution of 3-chloro-1-phenylpropan-1-one (5.0 g, 29.7 mmol) in hot ethanol (7 mL) was added potassium acetate (2.91 g, 29.77 mmol). After cooling to room temperature, the precipitated salt was removed via filtration. To the filtrate in a septum-sealed flask under a nitrogen bubbler was slowly added sodium cyanide (2.91 g, 59.3 mmol) as a solution in water (10 mL). After stirring at room temperature for 24 hours, ethanol (30 mL) was added, and the mixture was cooled in an ice bath. The precipitate was filtered and rinsed with ethanol to provide the product (3.42 g, 73%) as fluffy white solid.

Step B: Preparation of 3-(5-(2,5-difluorophenyl)-2-phenyl-2,3-dihydro-1,3,4-thiadiazol-2-yl)propanenitrile: To a solution of 4-oxo-4-phenylbutanenitrile (0.076 g, 0.48 mmol) in ethanol (5 mL) was added 2,5-difluorobenzothiohydrazide (0.09 g, 0.48 mmol). After stirring at 90° C. for 16 hours, the reaction mixture was concentrated under reduced pressure. The residue was dissolved in ethyl acetate and washed with water and brine, dried over Na₂SO₄, filtered and concentrated under reduced pressure. The residue was chromatographed (20% ethyl acetate in hexanes) to provide the product (0.087 g, 55% yield).

Step C: Preparation of 345-(2,5-difluorophenyl)-3-((S)-2-methoxypropanoyl)-2-phenyl-2,3-dihydro-1,3,4-thiadiazol-2-yl)propanenitrile: To a solution of 3-(5-(2,5-difluorophenyl)-2-phenyl-2,3-dihydro-1,3,4-thiadiazol-2-yl) propanenitrile (0.398 g, 1.208 mmol) and (S)-2-methoxypropanoic acid (0.1157 mL, 1.571 mmol) in DMF (40 mL) was added diisopropylethylamine (0.316 mL, 1.81 mmol) and PyBOP (1.26 g, 2.42 mmol). After stirring at room temperature for 28 hours, the mixture was diluted with saturated NaHCO₃ (100 mL) and extracted with ethyl acetate. The combined organics were washed with brine, dried over Na₂SO₄, filtered and concentrated under reduced pressure. The residue was chromatographed (30% ethyl acetate in hexanes) to provide the product (0.431 g, 86% yield) as a brown syrup.

Step D: Preparation of 345-(2,5-difluorophenyl)-3-((S)-2-methoxypropanoyl)-2-phenyl-2,3-dihydro-1,3,4-thiadiazol-2-yl)propanimidamide hydrochloride: To a cooled (0° C.) solution of 3-(5-(2,5-difluorophenyl)-3-((S)-2-methoxypropanoyl)-2-phenyl-2,3-dihydro-1,3,4-thiadiazol-2-yl)propanenitrile (0.053 g, 0.13 mmol) in ethanol (0.5 mL) was added a 9.8 M solution of ethanolic HCl (0.5 mL). After stirring at 0° C. for 10 minutes and then at room temperature for 4 hours, the reaction mixture was concentrated under reduced pressure. To the residue was added $NH_3$ (1.0 mL, 7.0 mmol, 7 M solution in methanol). After stirring at room temperature for 30 minutes, the mixture was concentrated under reduced pressure. The residue was chromatographed (dichloromethane followed by 20% MeOH and 1% aqueous $NH_4OH$ in dichloromethane) to afford the product as a mixture of diastereomers (3.4 mg, 15% yield). MS ESI (+) m/z 433 (M+1) detected; $^1$H NMR (400 MHz, $CDCl_3$) δ 9.0 (br, 4H), 8.7 (br, 4H), 7.51 (m, 2H), 7.38 (m, 8H), 7.32 (m, 2H), 7.14 (m, 4H), 4.73 (m, 2H), 3.57 (m, 2H), 3.42 (s, 3H), 3.35 (s, 3H), 2.75 (m, 4H), 2.33 (m, 1H), 2.23 (m, 1H), 1.52 (d, 3H, J=6.3 Hz), 1.48 (d, 3H, J=7.0 Hz).

Example 15

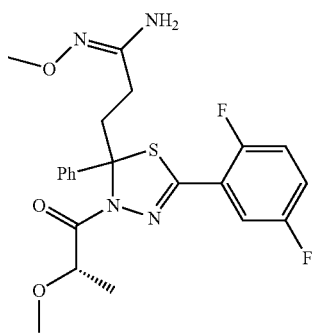

3-(5-(2,5-Difluorophenyl)-3-((S)-2-methoxypropanoyl)-2-phenyl-2,3-dihydro-1,3,4-thiadiazol-2-yl)-N'-methoxypropanimidamide To cooled (0° C.) solution of 3-(5-(2,5-difluorophenyl)-3-((S)-2-methoxypropanoyl)-2-phenyl-2,3-dihydro-1,3,4-thiadiazol-2-yl)propanenitrile (0.052 g, 0.13 mmol, Example 14, Step C) in ethanol (0.5 mL) was added 9.8 M ethanolic HCl (0.5 mL, 4.9 mmol). After stirring at room temperature for 6 hours, the mixture was concentrated under reduced pressure. To the residue was added methoxylamine hydrochloride (0.021 g, 0.21 mmol), absolute ethanol (0.5 mL) and triethylamine (0.087 mL, 0.63 mmol). After stirring at room temperature for 16 hours, the mixture was concentrated under reduced pressure. The residue was diluted with 10% $Na_2CO_3$ (30 mL) and extracted with dichloromethane. The combined organics were dried, filtered and concentrated under reduced pressure. The residue was chromatographed (40% ethyl acetate in hexanes) to afford the product as a mixture of diastereomers (14 mg, 25% yield). MS ESI (+) m/z 463 (M+1) detected; $^1$H NMR (4001 MHz, $CDCl_3$) δ 7.50 (m, 2H), 7.38 (m, 8H), 7.30 (m, 2H), 7.13 (m, 4H), 4.78 (q, 1H, J=6.3 Hz), 4.72 (q, 1H, J=6.3 Hz), 4.64 (br. s, 4H), 3.77 (s, 6H), 3.54 (m, 2H), 3.41 (s, 3H), 3.36 (s, 3H), 2.68 (m, 4H), 2.18 (m, 2H), 1.51 (d, 3H, J=6.3 Hz), 1.49 (d, 3H, J=7.0 Hz).

Example 16

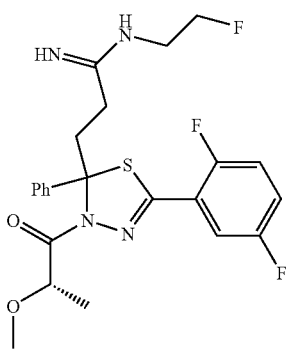

3-(5-(2,5-Difluorophenyl)-3-(S)-2-methoxypropanoyl)-2-phenyl-2,3-dihydro-1,3,4-thiadiazol-2-yl)-N-(2-fluoroethyl)propanimidamide Step A: Preparation of ethyl 3-(5-(2,5-difluorophenyl)-3-((S)-2-methoxypropanoyl)-2-phenyl-2,3-dihydro-1,3,4-thiadiazol-2-yl)propanimidate hydrochloride: To a cooled (0° C.) solution of 3-(5-(2,5-difluorophenyl)-3-((S)-2-methoxypropanoyl)-2-phenyl-2,3-dihydro-1,3,4-thiadiazol-2-yl)propanenitrile (0.041 g, 0.090 mmol, Example 14, Step C) in ethanol (0.5 mL) was added 9.8 M ethanolic HCl (0.5 mL, 4.9 mmol). After stirring at 0° C. for 1 hour and then at ambient temp for 8 hours, the mixture was concentrated under reduced pressure to provide the product.

Step B: Preparation of 345-(2,5-difluorophenyl)-3-((S)-2-methoxypropanoyl)-2-phenyl-2,3-dihydro-1,3,4-thiadiazol-2-yl)-N-(2-fluoroethyl)propanamidine: To a solution of ethyl 3-(5-(2,5-difluorophenyl)-3-((S)-2-methoxypropanoyl)-2-phenyl-2,3-dihydro-1,3,4-thiadiazol-2-yl)propanimidate hydrochloride (0.022 g, 0.0442 mmol) in ethanol (0.5 mL) was added triethylamine (0.120 ml, 0.861 mmol) and 2-fluoroethanamine hydrochloride (0.00440 g, 0.0442 mmol). After stirring at room temperature for 16 hours, the reaction mixture was concentrated, diluted with 10% $Na_2CO_3$ (30 mL) and extracted with dichloromethane. The combined organics were dried over $Na_2SO_4$, filtered and concentrated. The residue was chromatographed (10% methanol, 1% aqueous $NH_4OH$ in dichloromethane) to afford the product as a mixture of diastereomers (0.010 g, 47% yield). MS ESI (+) m/z 479 (M+1) detected; $^1$H NMR (400 MHz, $CDCl_3$) δ 7.50 (m, 2H), 7.38 (m, 8H), 7.31 (m, 2H), 7.14 (m, 4H), 4.79-4.70 (m, 2H), 4.65 (t, 2H, J=4.7 Hz), 4.53 (t, 2H, J=4.7 Hz), 3.58-3.45

(m, 6H), 3.42 (s, 3H), 3.36 (s, 3H), 2.84-2.71 (m, 4H), 2.36-2.18 (m, 2H), 1.52 (d, 3H, J=6.3 Hz), 1.48 (d, 3H, J=7.0 Hz).

Example 17

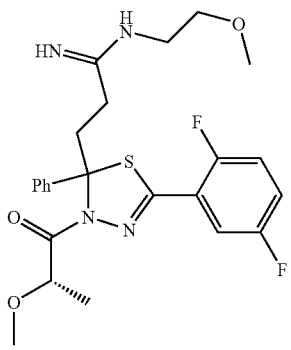

3-(5-(2,5-Difluorophenyl)-3-((S)-2-methoxypropanoyl)-2-phenyl-2,3-dihydro-1,3,4-thiadiazol-2-yl)-N-(2-methoxyethyl)propanimidamide Prepared according to the method of Example 16, using 2-methoxyethanamine in place of 2-fluoroethanamine to afford the product as a mixture of diastereomers. MS ESI (+) m/z 491 (M+1) detected; $^1$H NMR (400 MHz, CDCl$_3$) δ 7.51 (m, 2H), 7.42-7.29 (m, 8H), 7.31 (m, 2H), 7.14 (m, 4H), 4.78-4.69 (m, 2H), 3.58-3.50 (m, 6H), 3.42 (s, 3H), 3.36 (m, 13H), 2.82-2.68 (m, 4H), 2.31-2.13 (m, 2H), 1.52 (d, 3H, J=7.0 Hz), 1.48 (d, 3H, J=7.0 Hz).

Example 18

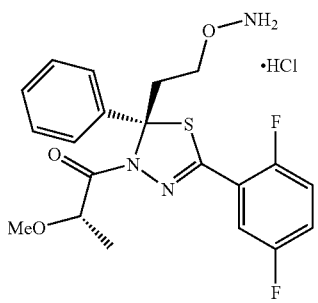

(S)-1-((S)-2-(2-(Aminooxy)ethyl)-5-(2,5-difluorophenyl)-2-phenyl-1,3,4-thiadiazol-3(2H)-yl)-2-methoxypropan-1-one Hydrochloride Step A: Preparation of tert-butyl 3-oxo-3-phenylpropoxycarbamate: To a cooled (0° C.) solution of tert-butyl hydroxycarbamate (1.90 g, 14.2 mmol) in THF (30 mL) was added NaH (0.285 g, 11.9 mmol). After stirring at 0° C. for 5 minutes and at room temperature for 10 minutes, the mixture was added to a solution of 3-chloro-1-phenylpropan-1-one (2.00 g, 11.9 mmol) in THF (10 mL). After stirring at room temperature for 30 minutes, the mixture was filtered, and the filtrate was concentrated under reduced pressure. The residue was chromatographed (20% ethyl acetate in hexanes) to provide the product (2.20 g, 69%) as a white solid.

Step B: Preparation of tert-butyl 2-(5-(2,5-difluorophenyl)-2-phenyl-2,3-dihydro-1,3,4-thiadiazol-2-yl)ethoxycarbamate: A mixture of tert-butyl 3-oxo-3-phenylpropoxycarbamate (1.09 g, 4.10 mmol) and 2,5-difluorobenzothiohydrazide (0.515 g, 2.74 mmol) in ethanol (3 mL) were stirred together at room temperature for 16 hours. The reaction mixture was concentrated under reduced pressure. The residue was chromatographed (20% ethyl acetate in hexanes) to provide the product as a white solid (0.94 g, 79% yield).

Step C: Preparation of (S)-1-((S)-2-(2-(aminooxy)ethyl)-5-(2,5-difluorophenyl)-2-phenyl-1,3,4-thiadiazol-3(2H)-yl)-2-methoxypropan-1-one hydrochloride: To a solution of tert-butyl 2-(5-(2,5-difluorophenyl)-2-phenyl-2,3-dihydro-1,3,4-thiadiazol-2-yl)ethoxycarbamate (0.340, 0.781 mmol) in DMF/dichloromethane (1:1, 2 mL) was added (S)-2-methoxypropanoic acid (0.122, 1.17 mmol), 1-(3-dimethylaminopropyl)-3-ethylcarbodiimide hydrochloride (0.299) g, 1.56 mmol). HOBt (0.211 g, 1.56 mmol), and triethylamine (0.33 mL, 2.34 mmol). After stirring at room temperature for 16 hours, the mixture was partitioned between 1N HCl and ethyl acetate. The organic layer vas washed with water and brine dried over Na$_2$SO$_4$, filtered and concentrated under reduced pressure. The residue was chromatographed (30% ethyl acetate in hexanes) to provide the diastereomerically enriched (9:1 S,S:S,R diastereomer ratio) Boc-protected product (35 mg, 9% yield). To this product was added a solution of HCl in dioxane (4M, 1 mL). After stirring at room temperature for 4 hours, the mixture was concentrated under reduced pressure and triturated with diethyl ether to provide the product as a white solid (0.025 g, 81% yield). MS ESI (+) m/z 444 (M+Na) detected; $^1$H NMR (400 MHz, CD$_3$OD) δ 7.68-7.63 (m, 1H), 7.48-7.46 (m, 2H), 7.44-7.38 (m, 2H), 7.36-7.30 (m, 3H), 4.76 (q, 1H, J=7.2 Hz), 4.54-4.48 (m, 1H), 4.43-4.36 (m, 1H), 3.67-3.59 (m, 1H), 3.33 (s, 3H), 3.05-2.97 (m, 1H), 1.43 (d, 3H, J=7.2 Hz).

Example 19

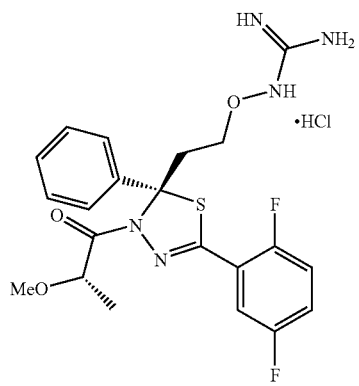

1-(2-((S)-5-(2,5-Difluorophenyl)-3-((S)-2-methoxypropanoyl)-2-phenyl-2,3-dihydro-1,3,4-thiadiazol-2-yl)ethoxy)guanidine Hydrochloride To a solution of (S)-1-((S)-2-(2-(aminooxy)ethyl)-5-(2,5-difluorophenyl)-2-phenyl-1,3,4-thiadiazol-3(2H)-yl)-2-methoxypropan-1-one hydrochloride (Example 18; 11.1 mg, 0.024 mmol) dissolved in THF was added triethylamine (25 μL, 0.18 mmol) and N,N'-di-Boc-1H-pyrazole-1-carboxamidine (0.025 g, 0.081 mmol). After stirring at room temperature for 16 hours, the mixture was concentrated under reduced pressure. The residue was chromatographed (20% ethyl acetate in hexanes) to provide the Boc-protected product (9 mg, 56%). To this material was added a solution of HCl in dioxane (4M, 1 mL). After stirring at room temperature for 16 hours, the mixture was concentrated under reduced pressure and triturated with diethyl ether to provide the product as a white solid (6 mg, 89% yield). MS ESI (+) m/z 464 (M+1) detected. $^1$H NMR (400 MHz, CD$_3$OD) δ 7.67-7.62 (m, 1H), 7.49-7.45 (m, 2H), 7.44-7.38 (m, 2H), 7.36-7.30 (m, 3H), 4.76 (q, 1H, J=7.2 Hz), 4.41-4.34 (m, 1H), 4.23-4.17 (m, 1H), 3.68-3.62 (m, 1H), 3.35 (s, 3H), 3.02-2.94 (m, 1H), 1.43 (d, 3H, J=7.2 Hz).

Example 20

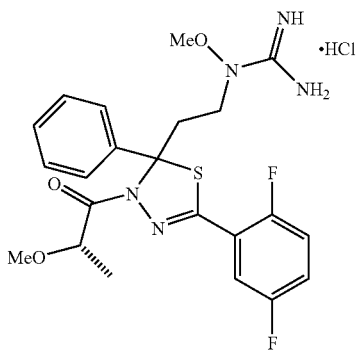

1-(2-(5-(2,5-Difluorophenyl)-3-((S)-2-methoxypropanoyl)-2-phenyl-2,3-dihydro-1,3,4-thiadiazol-2-yl)ethyl)-1-methoxyguanidine Hydrochloride Step A: Preparation of tert-butyl methoxycarbamate: To a solution of Boc-anhydride (12.0 g, 55.0 mmol) in dichloromethane (100 mL) was added a solution of sodium carbonate (17.5 g, in 100 mL water). To his mixture was added dropwise a solution of methoxyamine hydrochloride (13.8 g, 165 mmol) in water (100 mL). After stirring at room temperature for 18 hours, the organic layer was washed with water, dried over Na$_2$SO$_4$, filtered and concentrated under reduced pressure to provide the product (7.94 g, 98% yield) as a clear oil.

Step B: Preparation of tert-butyl methoxy(3-oxo-3-phenylpropyl)carbamate: To a cooled (0° C.) solution of tert-butyl methoxycarbamate (2.35 g, 16.0 mmol) in THF (50 mL) was slowly added NaH (0.640 g, 16.0 mmol). After stirring at 0° C. for 5 minutes and then at room temperature for 30 minutes, the mixture was added dropwise to a solution of 3-chloro-1-phenylpropan-1-one (2.84 g, 16.8 mmol) in THF (25 mL). After stirring at room temperature for 30 minutes, the mixture was filtered and the filtrate was concentrated under reduced pressure. The residue was chromatographed (10% ethyl acetate in hexanes) to provide the product (1.80 g, 40% yield) as a clear oil.

Step C: Preparation of tert-butyl 2-(5-(2,5-difluorophenyl)-2-phenyl-2,3-dihydro-1,3,4-thiadiazol-2-yl)ethyl (methoxy)carbamate: A mixture of 2,5-difluorobenzothiohydrazide (0.500 g 2.66 mmol) and tert-butyl methoxy(3-oxo-3-phenylpropyl)carbamate (1.11 g, 3.99 mmol) was stirred together in ethanol (5 mL) for 30 hours. The reaction mixture was concentrated under reduced pressure, and the residue was chromatographed (20% ethyl acetate in hexanes) to provide die product (0.650 g, 1.45 mmol) that was used in the next step without further purification.

Step D: Preparation of (2S)-1-(5-(2,5-difluorophenyl)-2-(2-(methoxyamino)ethyl)-2-phenyl-1,3,4-thiadiazol-3(2H)-yl)-2-methoxypropan-1-one hydrochloride: To a solution of (S)-2-methoxypropanoic acid (0.226, 2.17 mmol) in DMF (3 mL) was added diisopropylethylamine (0.50 mL, 2.89 mmol) and PyBOP (1.13 g, 2.17 mmol). After stirring at room temperature for 5 minutes, the mixture was added to tert-butyl 2-(5-(2,5-difluorophenyl)-2-phenyl-2,3-dihydro-1,3,4-thiadiazol-2-yl)ethyl(methoxy)carbamate (0.650 g, 1.45 mmol). After stirring at room temperature for 4 hours, die mixture was partitioned between saturated NaHCO$_3$ and ethyl acetate. The organic layer was washed with water and brine, dried over Na$_2$SO$_4$, filtered and concentrated under reduced pressure. The residue was chromatographed (15% ethyl acetate in hexanes) to provide the Boc-protected product (0.490 g, 63% yield) as a white foam. To this material was added HCl in dioxane (4 mL of a 4 M solution). After stirring at room temperature for 2 hours, the mixture was concentrated under reduced pressure and triturated with hexanes to provide the product as a white solid and as a mixture of diastereomers (0.211 g, 92% yield).

Step E: Preparation of 142-(5-(2,5-difluorophenyl)-3-((S)-2-methoxypropanoyl)-2-phenyl-2,3-dihydro-1,3,4-thiadiazol-2-yl)ethyl)-1-methoxyguanidine hydrochloride: To a solution of (2S)-1-(5-(2,5-difluorophenyl)-2-(2-(methoxyamino)ethyl)-2-phenyl-1,3,4-thiadiazol-3(2H)-yl)-2-methoxypropan-1-one hydrochloride (50 mg, 0.11 mmol) in THF (1 mL) was added NEt$_3$ (240 µL, 1.7 mmol) and N,N-di-Boc-1H-pyrazole-1-carboxamidine (260 mg, 0.85 mmol). The reaction mixture was stirred at room temperature for 1 week then concentrated. The residue was suspended in a 25% EtOAc in hexanes solution (5 mL), filtered, mid the filtrate was concentrated. Purification of the residue by flash chromatography (25% EtOAc in hexanes) afforded the di-Boc protected product as a white solid (45 mg, 63% yield). To this material was added a solution of HCl in dioxane (1 mL of a 4M solution), and the mixture was stirred at room temperature for 48 hours. The mixture was then concentrated, and the residue was triturated with Et$_2$O to afford the product as a white solid and as a mixture of diastereomers (30 mg, 88% yield). MS ESI (+) m/z 478 (M+H) detected; $^1$H NMR (400 MHz, CD$_3$OD) δ 7.64-7.69 (m, 2H), 7.50-7.44 (m, 4H), 7.44-7.38 (m, 4H), 7.36-7.29 (m, 6H), 4.86-4.77 (m, 2H), 4.25-4.14 (m, 2H), 3.84-3.75 (m, 1H), 3.77 (s, 3H), 3.76 (s, 3H), 3.74-3.64 (m, 1H), 3.59-3.50 (m 2H), 3.40 (s, 3H), 3.29 (s, 3H), 3.06-2.96 (m, 2H), 1.50 (d, 3H, J=6.5 Hz), 1.43 (d, 3H, J=6.5 Hz).

Example 21

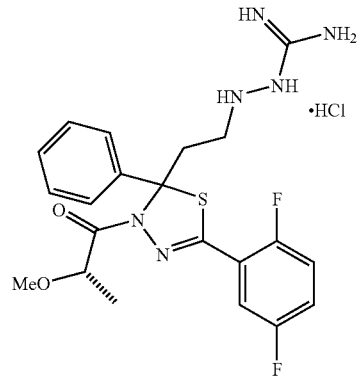

2-(2-(5-(2,5-Difluorophenyl)-3-((S)-2-methoxypropanoyl)-2-phenyl-2,3-dihydro-1,3,4-thiadiazol-2-yl)ethyl)hydrazinecarboximidamide Hydrochloride Step A: Preparation of N,N'-di-Boc-3-hydrazinyl-1-phenylpropan-1-one: To a cooled (0° C.) solution of di-Boc-hydrazine (2.0 g, 8.6 mmol) in THF (30 mL) was slowly added sodium hydride (210 mg, 8.6 mmol). After stirring at 0° C. for 5 minutes and then at room temperature for 30 minutes, the mixture was added to a solution of 3-chloro-1-phenylpropan-1-one (1.50 g, 8.6 mmol) in THF (10 mL). After stirring at room temperature for 30 minutes, water was added, and the mixture was partitioned between brine and ethyl acetate. The organic layer was dried over Na$_2$SO$_4$, filtered and concentrated under reduced pressure. The residue was chromatographed (15% ethyl acetate in hexanes) to provide the crude product.

Step B: Preparation of di-Boc-t-(2-(5-(2,5-difluorophenyl)-2-phenyl-2,3-dihydro-1,3,4-thiadiazol-2-yl)ethyl)hydrazine: A mixture of N,N'-di-Boc-3-hydrazinyl-1-phenyl-propan-1-one (0.868 g, 2.38 mmol) and 2,5-difluorobenzothiohydrazide (0.265 g, 1.41 mmol) in ethanol (3 mL) was stirred at room temperature for 3 days. The reaction mixture was concentrated under reduced pressure, and the residue was chromatographed (35% ethyl acetate in hexanes) to provide the crude product as a yellow foam.

Step C: Preparation of (2S)-1-(5-(2,5-difluorophenyl)-2-(2-hydrazinylethyl)-2-phenyl-1,3,4-thiadiazol-3(2H)-yl)-2-methoxypropan-1-one hydrochloride: To a solution of (S)-2-methoxypropanoic acid (0.146, 1.40 mmol) in DMF (4 mL) was added diisopropylethylamine (0.33 mL, 1.87 mmol) and PyBOP (0.730 g, 1.40 mmol). After stirring at room temperature for 5 minutes, the mixture was added to di-Boc-1-(2-(5-(2,5-difluorophenyl)-2-phenyl-2,3-dihydro-1,3,4-thiadiazol-2-yl)ethyl)hydrazine (0.500 g, 0.934 mmol). After stirring at room temperature for 4 hours, the mixture was partitioned between saturated NaHCO$_3$ and ethyl acetate. The organic layer was washed with water and brine, dried over Na$_2$SO$_4$, filtered and concentrated under reduced pressure. The residue was chromatographed (20% ethyl acetate in hexanes) to provide the Boc-protected product (0.311 g, 54% yield). To this product was added HCl (4 mL of 4N solution in dioxane). After stirring at room temperature for 28 hours, the mixture vas concentrated under reduced pressure and triturated with diethyl ether to provide the product as a yellow powder and as a mixture of diastereomers (0.125 g, 94% yield).

Step D: Preparation of 2-(2-(5-(2,5-difluorophenyl)-3-((S)-2-methoxypropanoyl)-2-phenyl-2,3-dihydro-1,3,4-thiadiazol-2-yl)ethyl)hydrazinecarboximidamide hydrochloride: To a solution of (2S)-1-(5-(2,5-difluorophenyl)-2-(2-hydrazinylethyl)-2-phenyl-1,3,4-thiadiazol-3(2H)-yl)-2-methoxypropan-1-one hydrochloride (40 mg, 0.088 mmol) in THF (1 mL) was added triethylamine (27 μL, 0.19 mmol) and N,N'-di-Boc-1H-pyrazole-1-carboxamidine (30 mg, 0.096 mmol). The reaction mixture was stirred at room temperature for 1 hour then concentrated. The residue was purified by flash chromatography (20% EtOAc in hexanes) to afford the di-Boc protected product as a white solid (30 mg, 52% yield). A solution of HCl in dioxane (4 mL of a 4M solution) was added to this material, and the reaction mixture was stirred at room temperature for 16 hours then concentrated. The residue was purified by flash chromatography (10-20% MeOH in CH$_2$Cl$_2$ with 1% NH$_4$OH), and the isolated material vas treated with excess HCl in MeOH then concentrated to afford the product as a mixture of diastereomers (6.0 mg, 27% yield). MS ESI (+) m/z 463 (M+1) detected; $^1$H NMR (400 MHz, CD$_3$OD) δ 7.66-7.61 (m, 2H), 7.51-7.44 (m, 4H), 7.43-7.37 (m, 4H), 7.36-7.29 (m, 6H), 4.86-4.77 (m, 2H), 3.66-3.47 (m, 4H), 3.37 (s, 3H), 3.28 (s, 3H), 2.96-2.70 (m, 4H), 1.46 (d, 3H, J=6.8 Hz), 1.42 (d, 3H, J=6.8 Hz).

Example 22

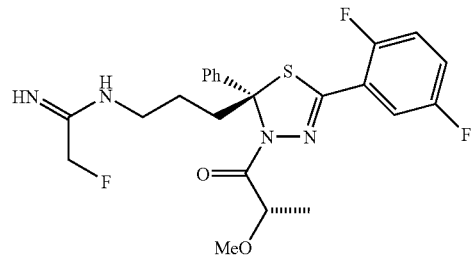

N-(3-((S)-5-(2,5-Difluorophenyl)-3-((R)-2-methoxypropanoyl)-2-phenyl-2,3-dihydro-1,3,4-thiadiazol-2-yl)propyl)-2-fluoroacetimidamide To a solution of (S)-1-((S)-2-(3-aminopropyl)-5-(2,5-difluorophenyl)-2-phenyl-1,3,4-thiadiazol-3(2H)-yl)-2-methoxypropan-1-one (Example 5, Steps A-F; 24.3 mg 0.049 mmol) and ethylfluoroacetimide hydrochloride (69.9 mg, 0.493 mmol, *J. Med. Chem.* 1990, 33(11), 3060-3067) in ethanol (0.5 mL) was added triethylamine (0.138 mL, 0.987 mmol). After stirring at room temperature for 23 hours, the reaction mixture was concentrated, diluted with 10% Na$_2$CO$_3$ (30 mL) and extracted with dichloromethane. The combined organics were dried over Na$_2$SO$_4$, filtered, and concentrated under reduced pressure. The residue was chromatographed (5% methanol, 0.7% aqueous NH$_4$OH in dichloromethane) to afford the product as a yellow film (9.8 mg, 42% yield). MS ESI (+) m/z 479 (M+1) detected; $^1$H NMR (400 MHz, CDCl$_3$) δ 7.51 (m, 1H), 7.41 (m, 2H), 7.36 (m, 2H), 7.29 (m, 1H), 7.13 (m 2H), 4.96 (br s, 1H), 4.84 (br s, 1H), 4.69 (m, 1H), 3.39 (s, 3H), 3.32 (m, 3H), 2.49 (m, 1H), 2.17 (m, 1H), 1.70 (m, 1H), 1.47 (d, 3H, J=7.0 Hz).

Example 23

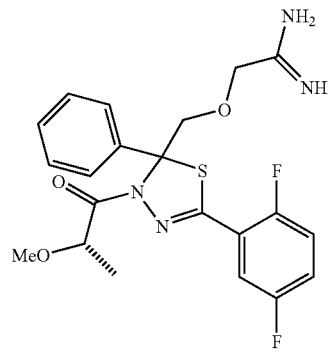

2-((5-(2,5-Difluorophenyl)-3-((S)-2-methoxypropanoyl)-2-phenyl-2,3-dihydro-1,3,4-thiadiazol-2-yl)methoxy)acetimidamide Step A: Preparation of 2-(2-oxo-2-phenylethoxy)acetic acid: To 1,4-dioxane-2,6-dione (1.0 g, 8.6 mmol) (Aldrich, 90%) in 17 mL benzene was added aluminum(III) chloride (3.4 g, 26 mmol). The reaction mixture was heated at 60° C. for 2 hours and then at reflux for 1 hour. The reaction mixture was poured onto 20 g of ice in 20 mL of concentrated HCl. This mixture vas stirred for 1 hour and then extracted with EtOAc. The combined organics were washed with brine, dried (MgSO$_4$), filtered, and concentrated. Purification of the residue by silica gel chromatography (10% EtOAc in hexanes to 2% HOAc in EtOAc) provided 0.95 g of a brown syrup that contained the desired product as the primary component. This mixture was used in the subsequent step without further purification.

Step B: Preparation of 2-(2-oxo-2-phenylethoxy)acetamide: To the mixture from step A (0.95 g) in 5 mL DCM at 0° C. was added DMF (0.0129 ml, 0.166 mmol) and then a solution of oxalyl chloride (0.640 ml, 7.34 mmol) in 5 mL of dichloromethane. The ice bath was removed, and the reaction mixture was stirred at room temperature for 2.5 hours. The reaction mixture was then concentrated to afford 1.11 g of crude acid chloride as a dark red syrup. This residue was dissolved in THF (20 mL) and cooled to −78° C. Ammonia gas was bubbled through the reaction solution for 5 minutes. The cold bath was removed, and the reaction mixture was stirred at ambient temperature for 2 hours. The reaction mixture was then concentrated, diluted with 10% Na$_2$CO$_3$ and extracted with EtOAc. The combined organics were dried (Na$_2$SO$_4$), filtered and concentrated. Purification of the crude product by silica gel chromatography (10% MeOH, 0.7% aq NH$_4$OH in dichloromethane,) provided 0.281 g of an orange-brown solid that consisted of two compounds with the primary component being the desired product. This mixture was used in the subsequent step without further purification Step C: Preparation of 2-(2-oxo-2-phenylethoxy)acetonitrile: To the mixture from step B (0.100 g) in pyridine (0.60 ml) at 0° C. was added TFAA (0.1097 ml, 0.7764 mmol). The reaction mixture was stirred for 3 hours and then concentrated. The residue was diluted with 1M KHSO$_4$ (30 mL) and extracted with EtOAc. The combined organics were washed with brine, dried (Na$_2$SO$_4$) filtered and concentrated. Purification of the residue by silica gel chromatography (10% EtOAc in hexanes) afforded 69.5 mg of a light red-tinted oil that contained the desired product as the primary component. This mixture was used in the subsequent stop without further purification.

Step D: Preparation of 2-((5-(2,5-difluorophenyl)-2-phenyl-2,3-dihydro-1,3,4-thiadiazol-2-yl)methoxy)acetonitrile: To 2,5-difluorobenzothiohydrazide hydrochloride (0.0885 g, 0.394 mmol) and the crude mixture from Step C (0.069 g) was added potassium acetate (0.0387 g, 0.394 mmol) in EtOH (0.7 mL). The reaction mixture was stirred at room temperature for 16 hours. The reaction mixture was diluted with dichloromethane (3 mL) and filtered. The filtrate was concentrated, and the crude material was purified by column chromatography (10% EtOAc in hexanes) to afford 97 mg of a colorless oil that contained the desired product as the primal component. This mixture was used in the subsequent step without further purification.

Step E: Preparation of 2-((5-(2,5-difluorophenyl)-3-((S)-2-methoxypropanoyl)-2-phenyl-2,3-dihydro-1,3,4-thiadiazol-2-yl)methoxy)acetonitrile: To a solution of HATU (0.0776 g, 0.2041 mmol) in 0.5 mL of DMF was added (S)-2-methoxy propanoic acid (0.0150 ml, 0.2041 mmol) and DIEA (0.0711 ml, 0.4083 mmol). This mixture was stirred at room temperature for 10 minutes and the crude mixture from Step D (0.047 g) was then added followed by 0.2 mL of DMF. The reaction mixture was stirred at room temperature for 40 hours. The reaction mixture was as diluted with saturated NaHCO$_3$ and extracted with EtOAc. The combined organics were washed with brine, dried (Na$_2$SO$_4$), filtered and concentrated. Purification of the residue by silica gel chromatography (20% EtOAc in hexanes) provided 3.5 mg of a cloudy film that contained the desired product as the primary component. This mixture was used in the subsequent step without further purification.

Step F: Preparation of 2-((5-(2,5-difluorophenyl)-3-((S)-2-methoxypropanoyl)-2-phenyl-2,3-dihydro-1,3,4-thiadiazol-2-yl)methoxy)acetimidamide: To a solution of the mixture from Step E (0.0035 g) in 0.5 mL of EtOH at 0° C. was added 9.8 M ethanolic HCl (0.50 ml, 4.9 mmol). The reaction mixture was stirred at 0° C. for 90 minutes and then at room temperature for 1 hour. The reaction mixture was concentrated to afford 4.2 mg of the crude ethyl imidate. To this residue was added 7 M ammonia in methanol (1 mL). The reaction mixture was stirred at room temperature for 3 hours and then concentrated. The residue was purified by silica gel chromatography (CH$_2$Cl$_2$-10% MeOH in CH$_2$Cl$_2$-10% MeOH, 2% concentrated aq NH$_4$OH in CH$_2$Cl$_2$) to afford 1.3 mg of 2-((5-(2,5-difluorophenyl)-3-((S)-2-methoxypropanoyl)-2-phenyl-2,3-dihydro-1,3,4-thiadiazol-2-yl)methoxy)acetamidine as a mixture of diastereomers. MS ESI (+) m/z 449 (M+1) detected; $^1$H NMR (400 MHz, 20:1 CDCl$_3$:CD$_3$OD) δ 7.52 (m, 2H), 7.41-7.30 (m, 10H), 7.18-7.11 (m, 4H), 4.93 (m, 2H), 4.77-4.70 (m, 2H), 4.66-4.52 (m, 4H), 4.38 (m, 2H), 3.40 (s, 3H), 3.36 (s, 3H), 1.47-1.44 (m, 6H).

Example 24

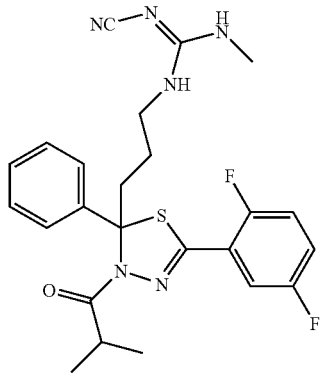

(Z)-2-Cyano-1-(3-(5-(2,5-difluorophenyl)-3-isobutyryl-2-phenyl-2,3-dihydro-1,3,4-thiadiazol-2-yl)propyl)-3-methylguanidine Step A: Preparation of 1-(2-(3-azidopropyl)-5-(2,5-difluorophenyl)-2-phenyl-1,3,4-thiadiazol-3(2H)-yl)-2-methylpropan-1-one: 2-(3-azidopropyl)-5-(2,5-difluorophenyl)-2-phenyl-2,3-dihydro-1,3,4-thiadiazole (100 mg, 0.278 mmol, Example 5, Step B) was weighed into a flask and dissolved in 5.0 mL of CH$_2$Cl$_2$. Triethylamine (0.058 ml, 0.417 mmol) was then added, followed by isobutyl chloride (35.5766 mg, 0.333893 mmol). The reaction was then allowed to slowly warm to ambient temperature overnight. The reaction was then concentrated in vacuo, then loaded direct to biotage (less pink precipitate), then purified by flash column chromatography (10% ethyl acetate/Hexanes), yielding the desired product 1-(2-(3-azidopropyl)-5-(2,5-difluorophenyl)-2-phenyl-1,3,4-thiadiazol-3(2H)-yl)-2-methylpropan-1-one (94 mg, 78%).

Step B: Preparation of 1-(2-(3-(amino)propyl)-5-(2,5-difluorophenyl)-2-phenyl-1,3,4-thiadiazol-3(2H)-yl)-2-methylpropan-1-one: 1-(2-(3-azidopropyl)-5-(2,5-difluorophenyl)-2-phenyl-1,3,4-thiadiazol-3(2H)-yl)-2-methylpropan-1-one (94 mg, 0.21 mmol) was weighed into a 25 mL 1 neck round bottom, and dissolved in 7 mL of MeOH—HCl (0.547 ml, 1.094 mmol) and Pd/C (23 mg, 0.021 mmol) were then added. The reaction was stirred at ambient temperature and under an atmosphere of $H_2$ for 45 minutes. The reaction was then concentrated affording the desired product (92.7 mg, 96%).

Step C: Preparation of (Z-2-cyano-1-(3-(5-(2,5-difluorophenyl)-3-isobutyryl-2-phenyl-2,3-dihydro-1,3,4-thiadiazol-2-yl)propyl)-3-methylguanidine: 1-(2-(3-aminopropyl)-5-(2,5-difluorophenyl)-2-phenyl-1,3,4-thiadiazol-3(2H)-yl)-2-methylpropan-1-one (66 mg, 0.163 mmol) was weighed into a 23 mL 1 neck round bottom flask, then dissolved in 2.0 mL IPA. Triethylamine (0.057 ml, 0.41 mmol) was then added followed by) diphenyl cyanocarbonimidate (78 mg, 0.327 mmol). The reaction was stirred at 23° C. for 1.5 hours. The reaction was then transferred to a pressure tube (20 mL), followed by addition of 3 mL of methyl amine (2.4 ml, 4.9 mmol) in MeOH. The reaction was then placed in a 60° C. bath for 12 hours. The reaction was then removed and concentrated, and purified by flash column chromatography (3-7% MeOH/DCM) to provide the desired product (41 mg, 52%) as a tan film. MS ESI (+) m/z 485 (M+E) detected; $^1H$ NMR (400 MHz, MeOH) δ 7.61 (m, 1H), 7.45 (d, J=7.8 Hz, 2H), 7.38 (m, 2H), 7.28 (m, 3H), 3.57 (m, 1H), 3.35 (m, 2H), 3.13 (m, 1H), 2.77 (s, 3H), 2.45 (m, 1H), 2.08 (m, 1H), 1.61 (m, 1H), 1.19 (d, 3H, J=6.2 Hz), 1.16 (d, 3H, J=7.2 Hz).

Example 25

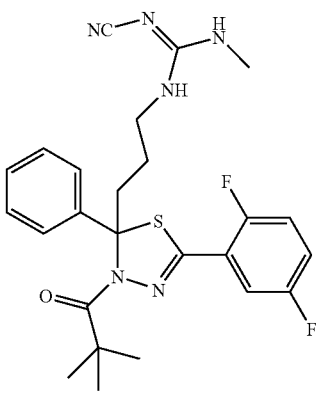

(Z)-2-Cyano-1-(3-(5-(2,5-difluorophenyl)-2-phenyl-3-pivaloyl-2,3-dihydro-1,3,4-thiadiazol-2-yl)propyl)-3-methylguanidine Step A: Preparation of 1-(2-(3-azidopropyl)-5-(2,5-difluorophenyl)-2-phenyl-1,3,4-thiadiazol-3(2H)-yl)-2,2-dimethylpropan-1-one: 2-(3-azidopropyl)-5-(2,5-difluorophenyl)-2-phenyl-2,3-dihydro-1,3,4-thiadiazole (100 mg, 0.278 mmol, Example 5, Step B) was weighed into a flask and dissolved in 5.0 mL of $CH_2Cl_2$. Triethylamine (0.0581 ml, 0.417 mmol) was then added, followed by pivaloyl chloride (40.2 mg, 0.333 mmol). The reaction was then allowed to slowly warm to ambient temperature over 12 hours. The reaction was concentrated and purified by flash column chromatography (10% ethyl acetate/Hexanes) affording the desired product (100 mg, 81%).

Step B: Preparation of 1-(2-(3-aminopropyl)-5-(2,5-difluorophenyl)-2-phenyl-1,3,4-thiadiazol-3(2H)-yl)-2,2-dimethylpropan-1-one hydrochloride: 1-(2-(3-azidopropyl)-5-(2,5-difluorophenyl)-2-phenyl-1,3,4-thiadiazol-3(2H)-yl)-2,2-dimethylpropan-1-one (100 mg, 0.2255 mmol) was weighed into a flask and dissolved in 7 mL of MeOH.HCl (0.563 ml, 1.12 mmol) and Pd/C (23 mg 0.22 mmol) were then added. The reaction was stirred at ambient temperature under an atmosphere or $H_2$ for 45 minutes. The reaction was then concentrated affording the desired product (97.4 mg, 95%).

Step C: Preparation of (Z)-2-cyano-1-(3-(5-(2,5-difluorophenyl)-2-phenyl-3-pivaloyl-2,3-dihydro-1,3,4-thiadiazol-2-yl)propyl)-3-methylguanidine: 1-(2-(3-aminopropyl)-5-(2,5-difluorophenyl)-2-phenyl-1,3,4-thiadiazol-3(2H)-yl)-2,2-dimethylpropan-1-one (66 mg, 0.158 mmol) was weighed into a flask, then dissolved in 2.0 mL IPA. Triethylamine (0.055 ml, 0.38 mmol) was then added followed by diphenyl cyanocarbonimidate (75 mg, 0.316 mmol). The reaction was then stirred at room temperature for 1.5 hours. The reaction was then transferred to a scaled tube, followed by addition of 3 mL of methyl amine (2.4 ml, 4.9 mmol) in MeOH. The reaction was then placed in a 60° C. bath for 12 hours. The reaction vas then removed and concentrated, and the residue was purified by flash column chromatography (3-7% MeOH/$CH_2Cl_2$) to provide the desired product (32 mg, 41%) as a light orange foam film. MS ESI (+) m/z 499 (M+E) detected; $^1H$ NMR (400 MHz, MeOH) δ 7.48 (m, 1H), 7.44 (d, J=8.0 Hz, 2H), 7.38 (m, 2H), 7.28 (m, 3H), 3.45 (m, 1H), 3.39 (m, 1H), 3.27 (m, 1H), 2.78 (s, 3H), 2.45 (m, 1H), 1.99 (m, 1H), 1.59 (m, 1H), 1.39 (s, 9H).

Example 26

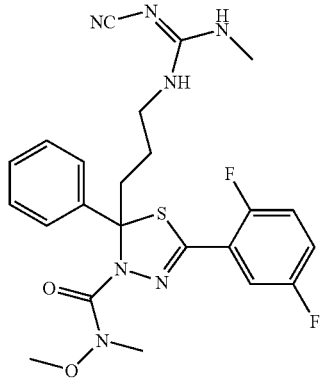

(Z)-2-(3-(2-Cyano-3-methylguanidino)propyl)-5-(2,5-difluorophenyl)-N-methoxy-N-methyl-2-phenyl-1,3,4-thiadiazole-3(2H)-carboxamide Step A: Preparation of (Z)-2-(3-(2-cyano-3-methylguanidino)propyl)-5-(2,5-difluorophenyl)-N-methoxy-N-methyl-2-phenyl-1,3,4-thiadiazole-3(2H)-carboxamide: 2-(3-aminopropyl)-5-(2,5-difluorophenyl)-N-methoxy-N-methyl-2-phenyl-1,3,4-thiadiazole-3(2H)-carboxamide (61 mg, 0.145 mmol, prepared as described in WO 2006/044825 Example 121) was weighed into a flask, then dissolved in 2.0 mL IPA.

Triethylamine (0.051 ml, 0.362 mmol) was then added, followed by diphenyl cyanocarbonimidate (69 mg, 0.290 mmol). The reaction was stirred at 23° C. for 1.5 hours, then transferred to a pressure tube, followed by addition of 3 mL of methyl amine (2.4 ml, 4.9 mmol) in MeOH. The reaction was then placed in a 60° C. bath for 12 hours and then concentrated. The residue was purified by flash column chromatography (3-7% MeOH/DCM) affording the desired product (27 mg, 37%) as an orange foam film. MS ESI (+) m/z 502 (M+E) detected; $^1$H NMR (400 MHz, CDCl$_3$) δ 7.52 (m, 1H), 7.46 (d, J=8.0H7-2H), 7.37 (m, 2H), 7.30 (m, 1H), 7.10 (m, 2H), 5.70 (m, 1h), 3.79 (s, 3H), 3.40 (m, 3H), 3.16 (m, 1H), 3.14 (s, 3H), 2.85 (s, 3H), 2.45 (m, 1H), 2.10 (m, 1H).

Example 27

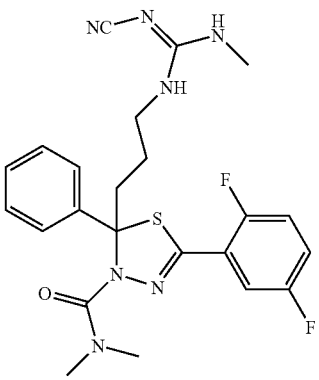

(Z)-2-(3-(2-Cyano-3-methylguanidino)propyl)-5-(2,5-difluorophenyl)-N,N-dimethyl-2-phenyl-1,3,4-thiadiazole-3(2H)-carboxamide Prepared according to the method of Example 26, using 2-(3-aminopropyl)-5-(2,5-difluorophenyl)-N,N-dimethyl-2-phenyl-1,3,4-thiadiazole-3(2H)carboxamide (prepared as described in WO 2006-044825 Example 30) in place of 2-(3-aminopropyl)-5-(2,5-difluorophenyl)-N-methoxy-N-methyl-2-phenyl-1,3,4-thiadiazole-3(2H)-carboxamide to afford the product as a mixture of enantiomers. MS ESI (+) m/z 486 (M+E) detected; $^1$H NMR (400 MHz, CDCl$_3$) δ 7.50 (m, 2H), 7.46 (m, 1H), 7.38 (m, 2H), 7.29 (m, 1H), 7.10 (m, 2H), 5.55 (m, 1H), 3.37 (m, 1H), 3.28 (m, 1H), 3.18 (m, 1H), 3.05 (s, 6H), 2.81 (d, J=5.3H7, 3H), 2.41 (m, 1H), 2.08 (m, 1H), 1.67 (m, 1H).

Example 28

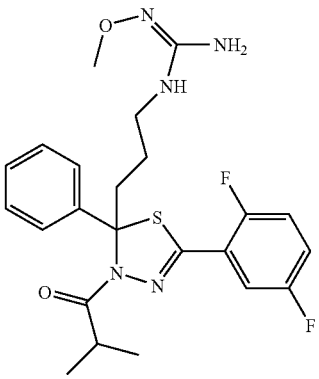

(Z)-1-(3-(5-(2,5-Difluorophenyl)-3-isobutyryl-2-phenyl-2,3-dihydro-1,3,4-thiadiazol-2-yl)propyl)-2-methoxyguanidine Step A: Preparation of (3-(5-(2,5-difluorophenyl)-3-isobutyryl-2-phenyl-2,3-dihydro-1,3,4-thiadiazol-2-yl)propyl)cyanamide: 1-(2-(3-aminopropyl)-5-(2,5-difluorophenyl)-2-phenyl-1,3,4-thiadiazol-3(2H)-yl)-2-methylpropan-1-one (33 mg, 0.0817867 mmol) was weighed into a 10 ml flask and dissolved in 1.0 mL of CH$_2$Cl$_2$, followed by addition of cyanogen bromide (11.2618 mg, 0.106323 mmol) and dropwise addition of triethylamine (0.0398980 mL, 0.286253 mmol). The reaction was then stirred at ambient temperature for 1 hour. The reaction was then concentrated in vacuo and the resulting tan foam was used in the next step without purification.

Step B: Preparation of (Z)-1-(3-(5-(2,5-difluorophenyl)-3-isobutyryl-2-phenyl-2,3-dihydro-1,3,4-thiadiazol-2-yl)propyl)-2-methoxyguanidine: Crude (3-(5-(2,5-difluorophenyl)-3-isobutyryl-2-phenyl-2,3-dihydro-1,3,4-thiadiazol-2-yl)propyl)cyanamide (35 mg, 0.08168 mmol) was transferred to a sealed tube in 3 mL of EtOH. Methoxyamine hydrochloride (170.5 mg, 2.042 mmol) and triethylamine (0.2846 ml, 2.042 mmol) were then added and the reaction heated to 70° C. for 18 hours. An additional 50 eq. of methoxyamine hydrochloride was added along with 50 equivalents of TEA. The reaction was then heated for 24 hours. The reaction was concentrated in vacuo, and the salts washed with ethyl acetate. The filtrate was then concentrated in vacuo, and the residue was purified by flash column chromatography (5-10% MeOH/CH$_2$Cl$_2$), to afford the desired product (14.2 mg, 36% yield) as a clear oil. MS ESI (+) m/z 476 (M+E) detected; $^1$H NMR (400 MHz, CDCl$_3$) δ 7.52 (m, 1H), 7.38 (m, 4H), 7.13 (ms 3H), 3.73 (s, 3H), 3.54 (m, 1H), 3.38 (m, 4H), 2.50 (m, 1H), 2.13 (m, 1H), 1.64 (m, 1H), 1.19 (d, J=7.2 Hz, 6H).

Example 29

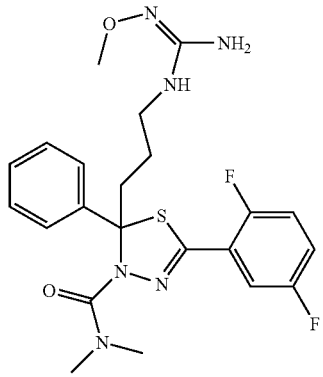

Synthesis of: (Z)-5-(2,5-difluorophenyl)-2-(3-(2-methoxyguanidino)propyl)-N,N-dimethyl-2-phenyl-1,3,4-thiadiazole-3(2H)-carboxamide Prepared according to the method of Example 28, using N,N-dimethyl—in place of isopropyl—substituted 1,3,4-thiadiazole-3(2H)-carboxamide to afford the product as a mixture of enantiomers. MS ESI (+) m/z 477 (M+E) detected; $^1$H NMR (400 MHz, CDCl$_3$) δ 7.52 (d, J=8.1 Hz, 2H), 7.44

(m, 1H), 7.36 (m, 2H), 7.22 (m, 1H), 7.09 (m, 2H), 4.49 (m, 1H), 3.67 (s, 3H), 3.21 (m, 2H), 3.16 (m, 1H), 3.04 (s, 6H), 2.42 (m, 1H), 2.03 (m, 1H), 1.68 (m, 1H).

The following compounds can be prepared by using, the procedures described above, utilizing the appropriately substituted reagents.

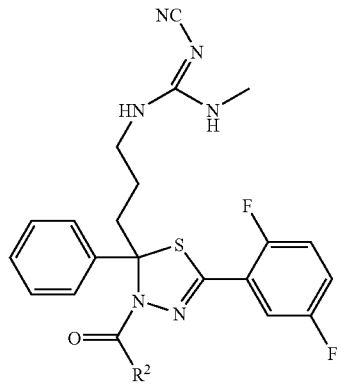

| R² | Name |
|---|---|
| 3-pyridyl | 2-cyano-1-(3-(5-(2,5-difluorophenyl)-3-nicotinoyl-2-phenyl-2,3-dihydro-1,3,4-thiadiazol-2-yl)propyl)-3-methylguanidine |
| 2-pyridyl | 2-cyano-1-(3-(5-(2,5-difluorophenyl)-2-phenyl-3-picolinoyl-2,3-dihydro-1,3,4-thiadiazol-2-yl)propyl)-3-methylguanidine |
| 3-methylfuran-2-yl | 2-cyano-1-(3-(5-(2,5-difluorophenyl)-3-(3-methylfuran-2-carbonyl)-2-phenyl-2,3-dihydro-1,3,4-thiadiazol-2-yl)propyl)-3-methylguanidine |
| 2-methylthiazol-5-yl | 2-cyano-1-(3-(5-(2,5-difluorophenyl)-3-(2-methylthiazole-5-carbonyl)-2-phenyl-2,3-dihydro-1,3,4-thiadiazol-2-yl)propyl)-3-methylguanidine |
| 5-methylthiophen-2-yl | 2-cyano-1-(3-(5-(2-5-difluorophenyl)-3-(5-methylthiophene-2-carbonyl)-2-phenyl-2,3-dihydro-1,3,4-thiadiazol-2-yl)propyl)-3-methylguanidine |
| 3-aminophenyl | 1-(3-(3-(3-aminobenzoyl)-5-(2,5-difluorophenyl)-2-phenyl-2,3-dihydro-1,3,4-thiadiazol-2-yl)propyl)-2-cyano-3-methylguanidine |
| ethyl | 2-cyano-1-(3-(5-(2,5-difluorophenyl)-2-phenyl-3-propionyl-2,3-dihydro-1,3,4-thiadiazol-2-yl)propyl)-3-methylguanidine |

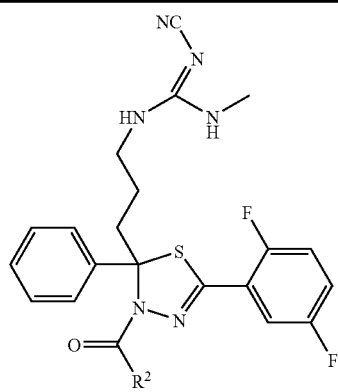

| R² | Name |
|---|---|
| 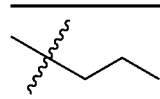 | 1-(3-(3-butyryl-5-(2,5-difluorophenyl)-2-phenyl-2,3-dihydro-1,3,4-thiadiazol-2-yl)propyl)-2-cyano-3-methylguanidine |
| 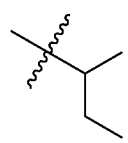 | 2-cyano-1-(3-(5-(2,5-difluorophenyl)-3-(2-methylbutanoyl)-2-phenyl-2,3-dihydro-1,3,4-thiadiazol-2-yl)propyl)-3-methylguanidine |
| 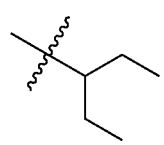 | 2-cyano-1-(3-(5-(2,5-difluorophenyl)-3-(2-ethylbutanoyl)-2-phenyl-2,3-dihydro-1,3,4-thiadiazol-2-yl)propyl)-3-methylguanidine |
|  | 2-cyano-1-(3-(3-(cyclobutanecarbonyl)-5-(2,5-difluorophenyl)-2-phenyl-2,3-dihydro-1,3,4-thiadiazol-2-yl)propyl)-3-methylguanidine |
| 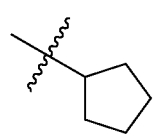 | 2-cyano-1-(3-(3-(cyclopentanecarbonyl)-5-(2,5-difluorophenyl)-2-phenyl-2,3-dihydro-1,3,4-thiadiazol-2-yl)propyl)-3-methylguanidine |
| 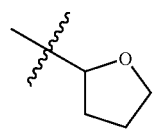 | 2-cyano-1-(3-(5-(2,5-difluorophenyl)-2-phenyl-3-(tetrahydrofuran-2-carbonyl)-2,3-dihydro-1,3,4-thiadiazol-2-yl)propyl)-3-methylguanidine |
| 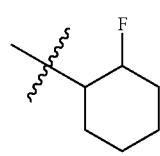 | 2-cyano-1-(3-(5-(2,5-difluorophenyl)-3-(2-fluorocyclohexanecarbonyl)-2-phenyl-2,3-dihydro-1,3,4-thiadiazol-2-yl)propyl)-3-methylguanidine |
| 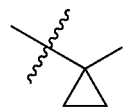 | 2-cyano-1-(3-(5-(2,5-difluorophenyl)-3-(1-methylcyclopropanecarbonyl)-2-phenyl-2,3-dihydro-1,3,4-thiadiazol-2-yl)propyl)-3-methylguanidine |
| 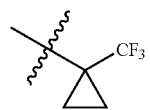 | 2-cyano-1-(3-(5-(2,5-difluorophenyl)-2-phenyl-3-(1-(trifluoromethyl)cyclopropanecarbonyl)-2,3-dihydro-1,3,4-thiadiazol-2-yl)propyl)-3-methylguanidine |

-continued

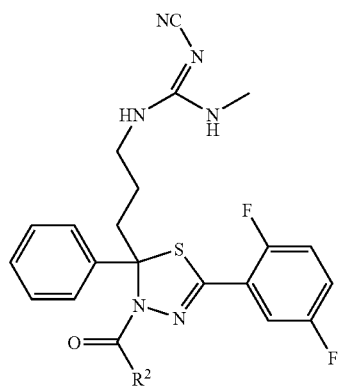

| R² | Name |
|---|---|
| ⌇⌇⌇—CH(OH)CH₃ (R) | 2-cyano-1-(3-(5-(2,5-difluorophenyl)-3-((R)-2-hydroxypropanoyl)-2-phenyl-2,3-dihydro-1,3,4-thiadiazol-2-yl)propyl)-3-methylguanidine |
| ⌇⌇⌇—CH(OH)CH₃ (S) | 2-cyano-1-(3-(5-(2,5-difluorophenyl)-3-((S)-2-hydroxypropanoyl)-2-phenyl-2,3-dihydro-1,3,4-thiadiazol-2-yl)propyl)-3-methylguanidine |
| ⌇⌇⌇—CH(OH)CH₂CH₃ (R) | 2-cyano-1-(3-(5-(2,5-difluorophenyl)-3-((R)-2-hydroxybutanoyl)-2-phenyl-2,3-dihydro-1,3,4-thiadiazol-2-yl)propyl)-3-methylguanidine |
| ⌇⌇⌇—CH(OH)CH₂CH₃ (S) | 2-cyano-1-(3-(5-(2,5-difluorophenyl)-3-((S)-2-hydroxybutanoyl)-2-phenyl-2,3-dihydro-1,3,4-thiadiazol-2-yl)propyl)-3-methylguanidine |
| ⌇⌇⌇—CH(OH)CH(CH₃)₂ (S) | 2-cyano-1-(3-(5-(2,5-difluorophenyl)-3-((S)-2-hydroxy-3-methylbutanoyl)-2-phenyl-2,3-dihydro-1,3,4-thiadiazol-2-yl)propyl)-3-methylguanidine |
| ⌇⌇⌇—CH(OH)C(CH₃)₃ (S) | 2-cyano-1-(3-(5-(2,5-difluorophenyl)-3-((S)-2-hydroxy-3,3-dimethylbutanoyl)-2-phenyl-2,3-dihydro-1,3,4-thiadiazol-2-yl)propyl)-3-methylguanidine |
| ⌇⌇⌇—CH(OH)-cyclopropyl (S) | 2-cyano-1-(3-(3-((S)-2-cyclopropyl-2-hydroxyacetyl)-5-(2,5-difluorophenyl)-2-phenyl-2,3-dihydro-1,3,4-thiadiazol-2-yl)propyl)-3-methylguanidine |
| ⌇⌇⌇—CH(NH₂)-cyclopropyl (S) | 1-(3-(3-((S)-2-amino-2-cyclopropylacetyl)-5-(2,5-difluorophenyl)-2-phenyl-2,3-dihydro-1,3,4-thiadiazol-2-yl)propyl)-2-cyano-3-methylguanidine |

-continued

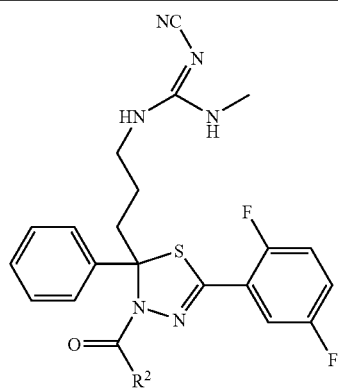

| R² | Name |
|---|---|
| 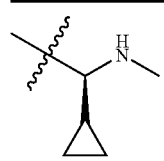 | 2-cyano-1-(3-(3-((S)-2-cyclopropyl-2-(methylamino)acetyl)-5-(2,5-difluorophenyl)-2-phenyl-2,3-dihydro-1,3,4-thiadiazol-2-yl)propyl)-3-methylguanidine |
| 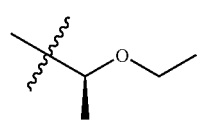 | 2-cyano-1-(3-(5-(2,5-difluorophenyl)-3-((S)-2-ethoxypropanoyl)-2-phenyl-2,3-dihydro-1,3,4-thiadiazol-2-yl)propyl)-3-methylguanidine |
| 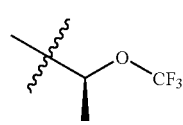 | 2-cyano-1-(3-(5-(2,5-difluorophenyl)-2-phenyl-3-((S)-2-(trifluoromethoxy)propanoyl)-2,3-dihydro-1,3,4-thiadiazol-2-yl)propyl)-3-methylguanidine |
| 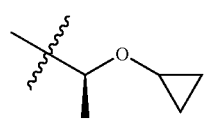 | 2-cyano-1-(3-(3-((S)-2-cyclopropoxypropanoyl)-5-(2,5-difluorophenyl)-2-phenyl-2,3-dihydro-1,3,4-thiadiazol-2-yl)propyl)-3-methylguanidine |
| 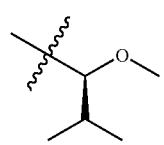 | 2-cyano-1-(3-(5-(2,5-difluorophenyl)-3-((S)-2-methoxy-3-methylbutanoyl)-2-phenyl-2,3-dihydro-1,3,4-thiadiazol-2-yl)propyl)-3-methylguanidine |
| 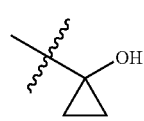 | 2-cyano-1-(3-(5-(2,5-difluorophenyl)-3-(1-hydroxycyclopropanecarbonyl)-2-phenyl-2,3-dihydro-1,3,4-thiadiazol-2-yl)propyl)-3-methylguanidine |
| 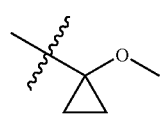 | 2-cyano-1-(3-(5-(2,5-difluorophenyl)-3-(1-methoxycyclopropanecarbonyl)-2-phenyl-2,3-dihydro-1,3,4-thiadiazol-2-yl)propyl)-3-methylguanidine |
| 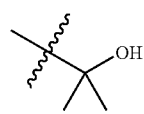 | 2-cyano-1-(3-(5-(2,5-difluorophenyl)-3-(2-hydroxy-2-methylpropanoyl)-2-phenyl-2,3-dihydro-1,3,4-thiadiazol-2-yl)propyl)-3-methylguanidine |
| 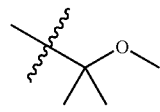 | 2-cyano-1-(3-(5-(2,5-difluorophenyl)-3-(2-methoxy-2-methylpropanoyl)-2-phenyl-2,3-dihydro-1,3,4-thiadiazol-2-yl)propyl)-3-methylguanidine |

-continued

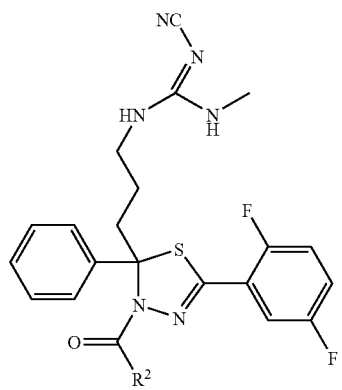

| R² | Name |
|---|---|
| (methoxymethyl group structure) | 2-cyano-1-(3-(5-(2,5-difluorophenyl)-3-((S)-2-methoxypropanoyl)-2-phenyl-2,3-dihydro-1,3,4-thiadiazol-2-yl)propyl)-3-methylguanidine |
| (methoxyethyl group structure) | 2-cyano-1-(3-(5-(2,5-difluorophenyl)-3-((R)-2-methoxybutanoyl)-2-phenyl-2,3-dihydro-1,3,4-thiadiazol-2-yl)propyl)-3-methylguanidine |
| (methoxy-t-butyl group structure) | 2-cyano-1-(3-(5-(2,5-difluorophenyl)-3-((S)-2-methoxy-3,3-dimethylbutanoyl)-2-phenyl-2,3-dihydro-1,3,4-thiadiazol-2-yl)propyl)-3-methylguanidine |
| (isobutoxy group structure) | 2-cyano-1-(3-(5-(2,5-difluorophenyl)-3-((S)-2-isobutoxy-3-methylbutanoyl)-2-phenyl-2,3-dihydro-1,3,4-thiadiazol-2-yl)propyl)-3-methylguanidine |
| (isopropoxy group structure) | 2-cyano-1-(3-(5-(2,5-difluorophenyl)-3-((S)-2-isopropoxy-3-methylbutanoyl)-2-phenyl-2,3-dihydro-1,3,4-thiadiazol-2-yl)propyl)-3-methylguanidine |
| (tert-butoxy group structure) | 1-(3-(3-((S)-2-tert-butoxypropanoyl)-5-(2,5-difluorophenyl)-2-phenyl-2,3-dihydro-1,3,4-thiadiazol-2-yl)propyl)-2-cyano-3-methylguanidine |
| (methoxymethoxy ethyl group structure) | 2-cyano-1-(3-(5-(2,5-difluorophenyl)-3-((S)-2-(methoxymethoxy)propanoyl)-2-phenyl-2,3-dihydro-1,3,4-thiadiazol-2-yl)propyl)-3-methylguanidine |
| (phenoxy group structure) | 2-cyano-1-(3-(5-(2,5-difluorophenyl)-3-((S)-2-phenoxypropanoyl)-2-phenyl-2,3-dihydro-1,3,4-thiadiazol-2-yl)propyl)-3-methylguanidine |

-continued

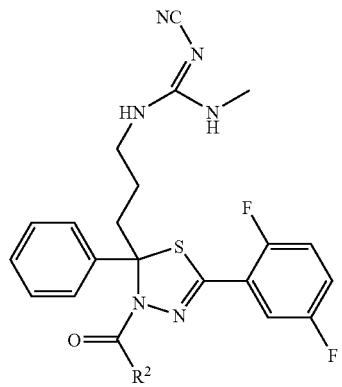

| R² | Name |
|---|---|
| 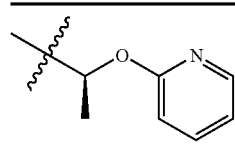 | 2-cyano-1-(3-(5-(2,5-difluorophenyl)-2-phenyl-3-((S)-2-(pyridin-2-yloxy)propanoyl)-2,3-dihydro-1,3,4-thiadiazol-2-yl)propyl)-3-methylguanidine |
| 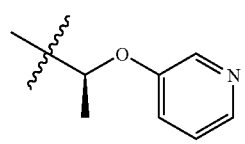 | 2-cyano-1-(3-(5-(2,5-difluorophenyl)-2-phenyl-3-((S)-2-(pyridin-3-yloxy)propanoyl)-2,3-dihydro-1,3,4-thiadiazol-2-yl)propyl)-3-methylguanidine |
| 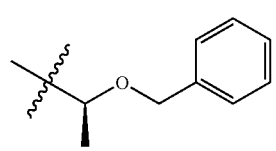 | 1-(3-(3-((S)-2-(benzyloxy)propanoyl)-5-(2,5-difluorophenyl)-2-phenyl-2,3-dihydro-1,34-thiadiazol-2-yl)propyl)-2-cyano-3-methylguanidine |
| 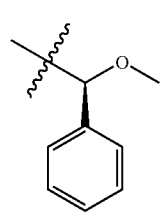 | 2-cyano-1-(3-(5-(2,5-difluorophenyl)-3-((S)-2-methoxy-2-phenylacetyl)-2-phenyl-2,3-dihydro-1,3,4-thiadiazol-2-yl)propyl)-3-methylguanidine |
| 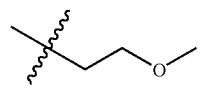 | 2-cyano-1-(3-(5-(2,5-difluorophenyl)-3-(3-methoxypropanoyl)-2-phenyl-2,3-dihydro-1,3,4-thiadiazol-2-yl)propyl)-3-methylguanidine |
| 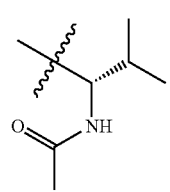 | N-((2S)-1-(2-(3-(2-cyano-3-methylguanidine)propyl)-5-(2,5-difluorophenyl)-2-phenyl-1,3,4-thiadiazol-3(2H)-yl)-3-methyl-1-oxobutan-2-yl)acetamide |
| 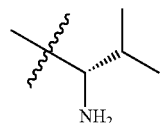 | 1-(3-(3-((S)-2-amino-3-methylbutanoyl)-5-(2,5-difluorophenyl)-2-phenyl-2,3-dihydro-1,3,4-thiadiazol-2-yl)propyl)-2-cyano-3-methylguanidine |
| 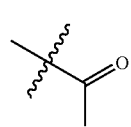 | 2-cyano-1-(3-(5-(2,5-difluorophenyl)-3-(2-oxopropanoyl)-2-phenyl-2,3-dihydro-1,3,4-thiadiazol-2-yl)propyl)-3-methylguanidine |

-continued

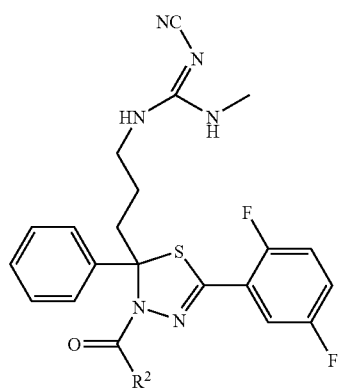

| R² | Name |
|---|---|
| 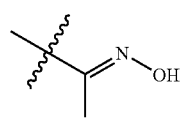 | 2-cyano-1-(3-(5-(2,5-difluorophenyl)-3-(2-(hydroxyimino)propanoyl)-2-phenyl-2,3-dihydro-1,3,4-thiadiazol-2-yl)propyl)-3-methylguanidine |
| 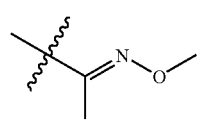 | 2-cyano-1-(3-(5-(2,5-difluorophenyl)-3-(2-(methoxyimino)propanoyl)-2-phenyl-2,3-dihydro-1,3,4-thiadiazol-2-yl)propyl)-3-methylguanidine |
| 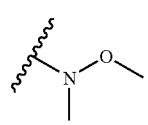 | 2-(3-(2-cyano-3-methylguanidino)propyl)-5-(2,5-difluorophenyl)-N-methoxy-N-methyl-2-phenyl-1,3,4-thiadiazole-3(2H)-carboxamide |
| 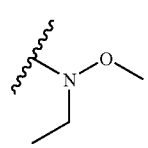 | 2-(3-(2-cyano-3-methylguanidino)propyl)-5-(2,5-difluorophenyl)-N-methoxy-N-ethyl-2-phenyl-1,3,4-thiadiazole-3(2H)-carboxamide |
| 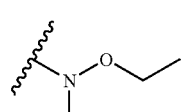 | 2-(3-(2-cyano-3-methylguanidino)propyl)-5-(2,5-difluorophenyl)-N-ethoxy-N-methyl-2-phenyl-1,3,4-thiadiazole-3(2H)-carboxamide |
| 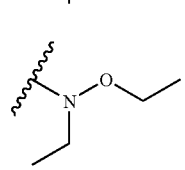 | 2-(3-(2-cyano-3-methylguanidino)propyl)-5-(2,5-difluorophenyl)-N-ethoxy-N-ethyl-2-phenyl-1,3,4-thiadiazole-3(2H)-carboxamide |
| 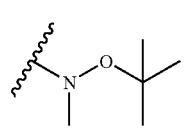 | 2-(3-(2-cyano-3-methylguanidino)propyl)-5-(2,5-difluorophenyl)-N-tertbutoxy-N-methyl-2-phenyl-1,3,4-thiadiazole-3(2H)-carboxamide |
| 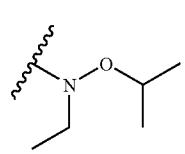 | 2-(3-(2-cyano-3-methylguanidino)propyl)-5-(2,5-difluorophenyl)-N-isopropoxy-N-ethyl-2-phenyl-1,3,4-thiadiazole-3(2H)-carboxamide |

-continued

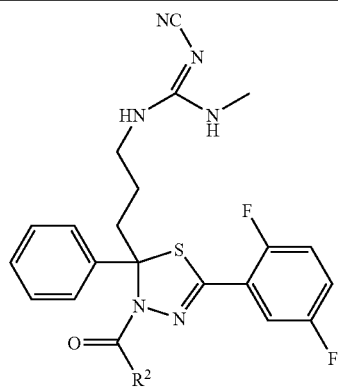

| R² | Name |
|---|---|
| 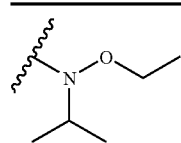 | 2-(3-(2-cyano-3-methylguanidino)propyl)-5-(2,5-difluorophenyl)-N-ethoxy-N-isopropyl-2-phenyl-1,3,4-thiadiazole-3(2H)-carboxamide |
| 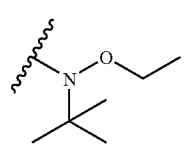 | 2-(3-(2-cyano-3-methylguanidino)propyl)-5-(2,5-difluorophenyl)-N-ethoxy-N-tertbutyl-2-phenyl-1,3,4-thiadiazole-3(2H)-carboxamide |
| 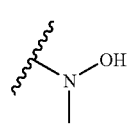 | 2-(3-(2-cyano-3-methylguanidino)propyl)-5-(2,5-difluorophenyl)-N-hydroxy-N-methyl-2-phenyl-1,3,4-thiadiazole-3(2H)-carboxamide |
| 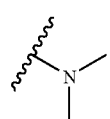 | 2-(3-(2-cyano-3-methylguanidino)propyl)-5-(2,5-difluorophenyl)-N,N-dimethyl-2-phenyl-1,3,4-thiadiazole-3(2H)-carboxamide |
| 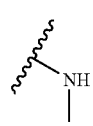 | 2-(3-(2-cyano-3-methylguanidino)propyl)-5-(2,5-difluorophenyl)-N-methyl-2-phenyl-1,3,4-thiadiazole-3(2H)-carboxamide |
| 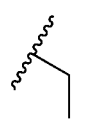 | (Z)-2-cyano-1-(3-(5-(2,5-difluorophenyl)-2-phenyl-3-propionyl-2,3-dihydro-1,3,4-thiadiazol-2-yl)propyl)-3-methylguanidine |
| 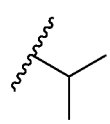 | (Z)-2-cyano-1-(3-(5-(2,5-difluorophenyl)-3-isobutyryl-2-phenyl-2,3-dihydro-1,3,4-thiadiazol-2-yl)propyl)-3-methylguanidine |
| 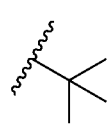 | (Z)-2-cyano-1-(3-(5-(2,5-difluorophenyl)-2-phenyl-3-pivaloyl-2,3-dihydro-1,3,4-thiadiazol-2-yl)propyl)-3-methylguanidine |
| 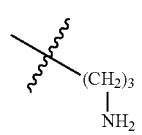 | (Z)-1-(3-(3-(4-aminobutanoyl)-5-(2,5-difluorophenyl)-2-phenyl-2,3-dihydro-1,3,4-thiadiazol-2-yl)propyl)-2-cyano-3-methylguanidine |

-continued

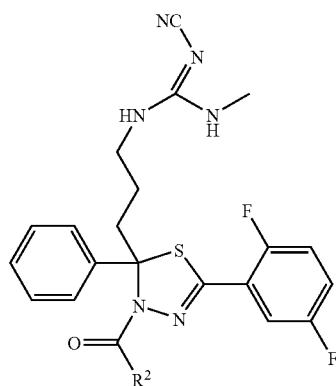

| R² | Name |
|---|---|
| 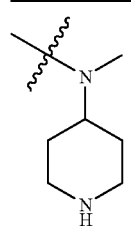 | (Z)-2-(3-(2-cyano-3-methylguanidino)propyl)-5-(2,5-difluorophenyl)-N-methyl-2-phenyl-N-(piperidin-4-yl)-1,3,4-thiadiazole-3(2H)-carboxamide |
| 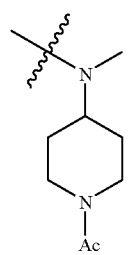 | (Z)-N-(1-acetylpiperidin-4-yl)-2-(3-(2-cyano-3-methylguanidino)propyl)-5-(2,5-difluorophenyl)-N-methyl-2-phenyl-1,3,4-thiadiazole-3(2H)-carboxamide |
| 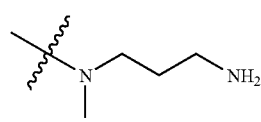 | (Z)-N-(3-aminopropyl)-2-(3-(2-cyano-3-methylguanidino)propyl)-5-(2,5-difluorophenyl)-N-methyl-2-phenyl-1,3,4-thiadiazole-3(2H)-carboxamide |
| 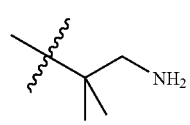 | (Z)-1-(3-(3-(3-amino-2,2-dimethylpropanoyl)-5-(2,5-difluorophenyl)-2-phenyl-2,3-dihydro-1,3,4-thiadiazol-2-yl)propyl)-2-cyano-3-methylguanidine |
| 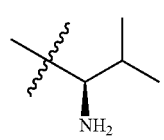 | (Z)-1-(3-(3-((R)-2-amino-3-methylbutanoyl)-5-(2,5-difluorophenyl)-2-phenyl-2,3-dihydro-1,3,4-thiadiazol-2-yl)propyl)-2-cyano-3-methylguanidine |
| 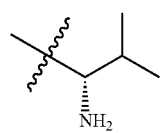 | (Z)-1-(3-(3-((S)-2-amino-3-methylbutanoyl)-5-(2,5-difluorophenyl)-2-phenyl-2,3-dihydro-1,3,4-thiadiazol-2-yl)propyl)-2-cyano-3-methylguanidine |
| 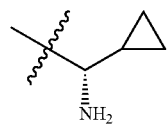 | (Z)-1-(3-(3-((S)-2-amino-2-cyclopropylacetyl)-5-(2,5-difluorophenyl)-2-phenyl-2,3-dihydro-1,3,4-thiadiazol-2-yl)propyl)-2-cyano-3-methylguanidine |

-continued

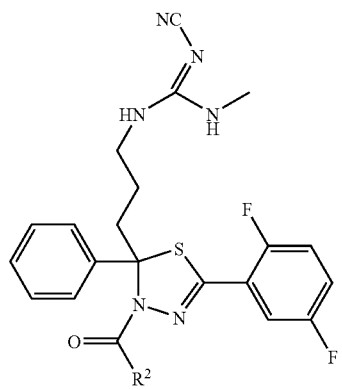

| R² | Name |
|---|---|
| 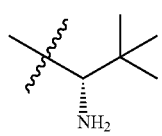 | (Z)-1-(3-(3-((S)-2-amino-3,3-dimethylbutanoyl)-5-(2,5-difluorophenyl)-2-phenyl-2,3-dihydro-1,3,4-thiadiazol-2-yl)propyl)-2-cyano-3-methylguanidine |
| 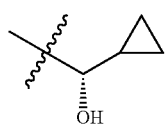 | (Z)-2-cyano-1-(3-(3-((S)-2-cyclopropyl-2-hydroxyacetyl)-5-(2,5-difluorophenyl)-2-phenyl-2,3-dihydro-1,3,4-thiadiazol-2-yl)propyl)-3-methylguanidine |
| 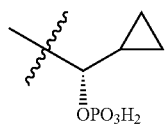 | (1S)-2-(2-(3-((Z)-2-cyano-3-methylguanidino)propyl)-5-(2,5-difluorophenyl)-2-phenyl-1,3,4-thiadiazol-3(2H)-yl)-1-cyclopropyl-2-oxoethyl dihydrogen phosphate |
| 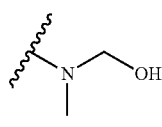 | (Z)-2-(3-(2-cyano-3-methylguanidino)propyl)-5-(2,5-difluorophenyl)-N-(hydroxymethyl)-N-methyl-2-phenyl-1,3,4-thiadiazole-3(2H)-carboxamide |
| 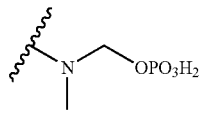 | (Z)-(2-(3-(2-cyano-3-methylguanidino)propyl)-5-(2,5-difluorophenyl)-N-methyl-2-phenyl-2,3-dihydro-1,3,4-thiadiazole-3-carboxamido)methyl dihydrogen phosphate |
| 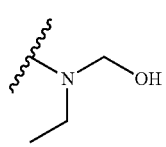 | (Z)-2-(3-(2-cyano-3-methylguanidino)propyl)-5-(2,5-difluorophenyl)-N-ethyl-N-(hydroxymethyl)-2-phenyl-1,3,4-thiadiazole-3(2H)-carboxamide |
| 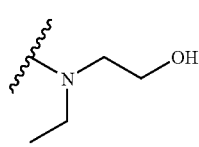 | (Z)-2-(3-(2-cyano-3-methylguanidino)propyl)-5-(2,5-difluorophenyl)-N-ethyl-N-(2-hydroxyethyl)-2-phenyl-1,3,4-thiadiazole-3(2H)-carboxamide |
| 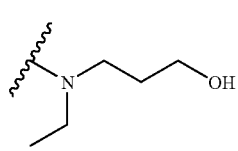 | (Z)-2-(3-(2-cyano-3-methylguanidino)propyl)-5-(2,5-difluorophenyl)-N-ethyl-N-(3-hydroxypropyl)-2-phenyl-1,3,4-thiadiazole-3(2H)-carboxamide |

-continued

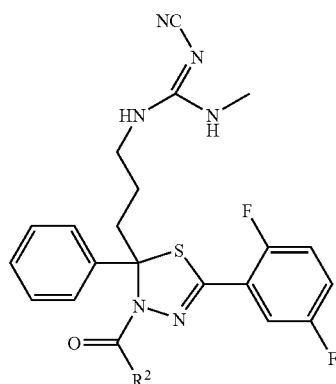

| R² | Name |
|---|---|
| ~N(Et)(CH₂)₄OH | (Z)-2-(3-(2-cyano-3-methylguanidino)propyl)-5-(2,5-difluorophenyl)-N-ethyl-N-(4-thydroxybutyl)-2-phenyl-1,3,4-thiadiazole-3(2H)-carboxamide |
| ~N(Et)(CH₂)₂NH₂ | (Z)-N-(2-aminoethyl)-2-(3-(2-cyano-3-methylguanidino)propyl)-5-(2,5-difluorophenyl)-N-ethyl-2-phenyl-1,3,4-thiadiazole-3(2H)-carboxamide |
| ~N(Et)(CH₂)₃NH₂ | (Z)-N-(3-aminopropyl)-2-(3-(2-cyano-3-methylguanidino)propyl)-5-(2,5-difluorophenyl)-N-ethyl-2-phenyl-1,3,4-thiadiazole-3(2H)-carboxamide |
| ~N(Et)(CH₂)₄NH₂ | (Z)-N-(4-aminobutyl)-2-(3-(2-cyano-3-methylguanidino)propyl)-5-(2,5-difluorophenyl)-N-ethyl-2-phenyl-1,3,4-thiadiazole-3(2H)-carboxamide |
| azetidinyl | (Z)-1-(3-(3-(azetidine-1-carbonyl)-5-(2,5-difluorophenyl)-2-phenyl-2,3-dihydro-1,3,4-thiadiazol-2-yl)propyl)-2-cyano-3-methylguanidine |
| pyrrolidinyl | (Z)-2-cyano-1-(3-(5-(2,5-difluorophenyl)-2-phenyl-3-(pyrrolidine-1-carbonyl)-2,3-dihydro-1,3,4-thiadiazole-2-yl)propyl)-3-methylguanidine |
| piperidinyl | (Z)-2-cyano-1-(3-(5-(2,5-difluorophenyl)-2-phenyl-3-(piperidine-1-carbonyl)-2,3-dihydro-1,3,4-thiadiazol-2-yl)propyl)-3-methylguanidine |
| morpholinyl | (Z)-2-cyano-1-(3-(5-(2,5-difluorophenyl)-3-(morpholine-4-carbonyl)-2-phenyl-2,3-dihydro-1,3,4-thiadiazol-2-yl)propyl)-3-methylguanidine |

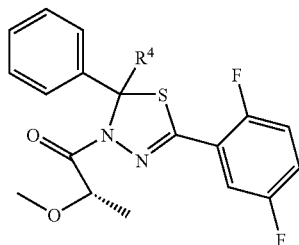

| R⁴ | Name |
|---|---|
| *-CH₂CH₂-NH-C(=NH)-CH₃ | N-(2-(5-(2,5-difluorophenyl)-3-((S)-2-methoxypropanoyl)-2-phenyl-2,3-dihydro-1,3,4-thiadiazol-2-yl)ethyl)acetimidamide |
| *-CH₂CH₂CH₂-NH-C(=NH)-CH₃ | N-(3-(5-(2,5-difluorophenyl)-3-((S)-2-methoxypropanoyl)-2-phenyl-2,3-dihydro-1,3,4-thiadiazol-2-yl)propyl)acetimidamide |
| *-CH₂-NH-C(=NH)-CH₃ | N-((5-(2,5-difluorophenyl)-3-((S)-2-methoxypropanoyl)-2-phenyl-2,3-dihydro-1,3,4-thiadiazol-2-yl)methyl)acetimidamide |
| *-CH₂CH₂CH₂-NH-C(=N-OMe)-CH₃ | N-(3-(5-(2,5-difluorophenyl)-3-((S)-2-methoxypropanoyl)-2-phenyl-2,3-dihydro-1,3,4-thiadiazol-2-yl)propyl)-N'-methoxyacetimidamide |
| *-CH₂CH₂CH₂-NH-C(=N-CN)-CH₃ | N'-cyano-N-(3-(5-(2,5-difluorophenyl)-3-((S)-2-methoxypropanoyl)-2-phenyl-2,3-dihydro-1,3,4-thiadiazol-2-yl)propyl)acetimidamide |
| *-CH₂CH₂CH₂-NH-C(=NH)-CH₂F | N-(3-(5-(2,5-difluorophenyl)-3-((S)-2-methoxypropanoyl)-2-phenyl-2,3-dihydro-1,3,4-thiadiazol-2-yl)propyl)-2-fluoroacetimidamide |
| *-CH₂CH₂CH₂-NH-C(NH₂)=CH-NO₂ | (2S)-1-(2-(3-((E)-1-amino-2-nitrovinylamino)propyl)-5-(2,5-difluorophenyl)-2-phenyl-1,3,4-thiadiazol-3(2H)-yl)-2-methoxypropan-1-one |
| *-CH₂CH₂CH₂-NH-C(=N-CN)-NH₂ | 2-cyano-1-(3-(5-(2,5-difluorophenyl)-3-((S)-2-methoxypropanoyl)-2-phenyl-2,3-dihydro-1,3,4-thiadiazol-2-yl)propyl)guanidine |
| *-CH₂CH₂-NH-C(=N-CN)-NH₂ | 2-cyano-1-(2-(5-(2,5-difluorophenyl)-3-((S)-2-methoxypropanoyl)-2-phenyl-2,3-dihydro-1,3,4-thiadiazol-2-yl)ethyl)guanidine |

-continued

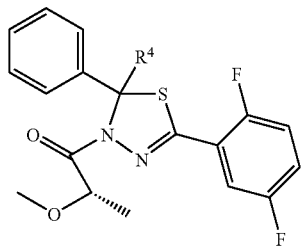

| R⁴ | Name |
|---|---|
| (guanidine with CN) | 2-cyano-1-((5-(2,5-difluorophenyl)-3-((S)-2-methoxypropanoyl)-2-phenyl-2,3-dihydro-1,3,4-thiadiazol-2-yl)methyl)guanidine |
| (guanidine propyl with CONH₂) | 1-(amino(3-(5-(2,5-difluorophenyl)-3-((S)-2-methoxypropanoyl)-2-phenyl-2,3-dihydro-1,3,4-thiadiazol-2-yl)propylamino)methylene)urea |
| (guanidine ethyl with H₂NOC) | 1-(amino(2-(5-(2,5-difluorophenyl)-3-((S)-2-methoxypropanoyl)-2-phenyl-2,3-dihydro-1,3,4-thiadiazol-2-yl)ethylamino)methylene)urea |
| (guanidine methyl with CONH₂) | 1-(amino((5-(2,5-difluorophenyl)-3-((S)-2-methoxypropanoyl)-2-phenyl-2,3-dihydro-1,3,4-thiadiazol-2-yl)methylamino)methylene)urea |
| (guanidine propyl with acetyl) | N-(amino(3-(5-(2,5-difluorophenyl)-3-((S)-2-methoxypropanoyl)-2-phenyl-2,3-dihydro-1,3,4-thiadiazol-2-yl)propylamino)methylene)acetamide |
| (guanidine propyl with NC and acetamide) | N-(cyanamido(3-(5-(2,5-difluorophenyl)-3-((S)-2-methoxypropanoyl)-2-phenyl-2,3-dihydro-1,3,4-thiadiazol-2-yl)propylamino)methylene)acetamide |
| (guanidine propyl with diacetyl) | N,N'-((3-(5-(2,5-difluorophenyl)-3-((S)-2-methoxypropanoyl)-2-phenyl-2,3-dihydro-1,3,4-thiadiazol-2-yl)propylamino)methylene)diacetamide |
| (guanidine propyl with OMe) | 1-(3-(5-(2,5-difluorophenyl)-3-((S)-2-methoxypropanoyl)-2-phenyl-2,3-dihydro-1,3,4-thiadiazol-2-yl)propyl)-2-methoxyguanidine |

-continued

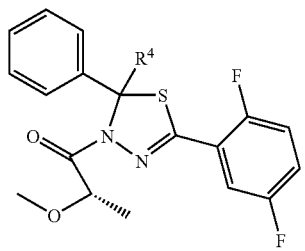

| R⁴ | Name |
|---|---|
| (guanidine with NHMe) | 1-(3-(5-(2,5-difluorophenyl)-3-((S)-2-methoxypropanoyl)-2-phenyl-2,3-dihydro-1,3,4-thiadiazol-2-yl)propyl)-3-methylguanidine |
| (N-methoxy guanidine) | 1-(3-(5-(2,5-difluorophenyl)-3-((S)-2-methoxypropanoyl)-2-phenyl-2,3-dihydro-1,3,4-thiadiazol-2-yl)propyl)-1-methoxyguanidine |
| (1,1-dimethylguanidine) | 3-(3-(5-(2,5-difluorophenyl)-3-((S)-2-methoxypropanoyl)-2-phenyl-2,3-dihydro-1,3,4-thiadiazol-2-yl)propyl)-1,1-dimethylguanidine |
| (2,3-dimethylguanidine) | 1-(3-(5-(2,5-difluorophenyl)-3-((S)-2-methoxypropanoyl)-2-phenyl-2,3-dihydro-1,3,4-thiadiazol-2-yl)propyl)-2,3-dimethylguanidine |
| (iminotetrahydropyrimidinyl) | (2S)-1-(5-(2,5-difluorophenyl)-2-(3-(2-iminotetrahydropyrimidin-1(2H)-yl)propyl)-2-phenyl-1,3,4-thiadiazol-3(2H)-yl)-2-methoxypropan-1-one |
| (tetrahydropyrimidin-2-ylamino) | (2S)-1-(5-(2,5-difluorophenyl)-2-phenyl-2-(3-(1,4,5,6-tetrahydropyrimidin-2-ylamino)propyl)-1,3,4-thiadiazol-3(2H)-yl)-2-methoxypropan-1-one |
| (pyrrolidine carboximidamide) | N-(3-(5-(2,5-difluorophenyl)-3-((S)-2-methoxypropanoyl)-2-phenyl-2,3-dihydro-1,3,4-thiadiazol-2-yl)propyl)pyrrolidine-1-carboximidamide |
| (butanimidamide) | 4-(5-(2,5-difluorophenyl)-3-((S)-2-methoxypropanoyl)-2-phenyl-2,3-dihydro-1,3,4-thiadiazol-2-yl)butanimidamide |
| (pentanimidamide) | 5-(5-(2,5-difluorophenyl)-3-((S)-2-methoxypropanoyl)-2-phenyl-2,3-dihydro-1,3,4-thiadiazol-2-yl)pentanimidamide |

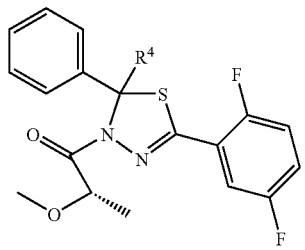

| R⁴ | Name |
|---|---|
| | 3-(5-(2,5-difluorophenyl)-3-((S)-2-methoxypropanoyl)-2-phenyl-2,3-dihydro-1,3,4-thiadiazol-2-yl)propanimidamide |
| | 4-(5-(2,5-difluorophenyl)-3-((S)-2-methoxypropanoyl)-2-phenyl-2,3-dihydro-1,3,4-thiadiazol-2-yl)-N'-methoxybutanimidamide |
| | N'-cyano-4-(5-(2,5-difluorophenyl)-3-((S)-2-methoxypropanoyl)-2-phenyl-2,3-dihydro-1,3,4-thiadiazol-2-yl)butanimidamide |
| | 4-(5-(2,5-difluorophenyl)-3-((S)-2-methoxypropanoyl)-2-phenyl-2,3-dihydro-1,3,4-thiadiazol-2-yl)-2,2-difluorobutanimidamide |
| | 2-((5-(2,5-difluorophenyl)-3-((S)-2-methoxypropanoyl)-2-phenyl-2,3-dihydro-1,3,4-thiadiazol-2-yl)methoxy)acetimidamide |
| | 4-(5-(2,5-difluorophenyl)-3-((S)-2-methoxypropanoyl)-2-phenyl-2,3-dihydro-1,3,4-thiadiazol-2-yl)-N-methylbutanimidamide |
| | 1-(2-(5-(2,5-difluorophenyl)-3-((S)-2-methoxypropanoyl)-2-phenyl-2,3-dihydro-1,3,4-thiadiazol-2-yl)ethoxy)guanidine |
| | 1-(2-(5-(2,5-difluorophenyl)-3-((S)-2-methoxypropanoyl)-2-phenyl-2,3-dihydro-1,3,4-thiadiazol-2-yl)ethoxy)-3-methylguanidine |
| | N-(N-(2-(5-(2,5-difluorophenyl)-3-((S)-2-methoxypropanoyl)-2-phenyl-2,3-dihydro-1,3,4-thiadiazol-2-yl)ethoxy)carbamimidoyl)acetamide |

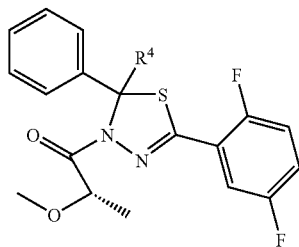

| R⁴ | Name |
|---|---|
| ~~~O~NH, HN=\<N (tetrahydropyrimidine) | (2S)-1-(5-(2,5-difluorophenyl)-2-phenyl-2-(2-(1,4,5,6-tetrahydropyrimidin-2-ylaminooxy)ethyl)-1,3,4-thiadiazol-3-(2H)-yl)-2-methoxypropan-1-one |
| ~~~O~NH, C(CH₃)=NH | N-(2-(5-(2,5-difluorophenyl)-3-((S)-2-methoxypropanoyl)-2-phenyl-2,3-dihydro-1,3,4-thiadiazol-2-yl)ethoxy)acetimidamide |
| ~~~O~NH, C(CH₃)=N-CH₃ | (E)-N-(2-(5-(2,5-difluorophenyl)-3-((S)-2-methoxypropanoyl)-2-phenyl-2,3-dihydro-1,3,4-thiadiazol-2-yl)ethoxy)-N'-methylacetimidamide |
| ~~~O~NH, C(CH₃)=N-C(=O)CH₃ | N-(1-(2-(5-(2,5-difluorophenyl)-3-((S)-2-methoxypropanoyl)-2-phenyl-2,3-dihydro-1,3,4-thiadiazol-2-yl)ethoxyamino)ethylidene)acetamide |
| ~~~O~N=C(CH₃)₂ | (2S)-1-(5-(2,5-difluorophenyl)-2-phenyl-2-(2-(propan-2-ylideneaminooxy)ethyl)-1,3,4-thiadiazol-3(2H)-yl)-2-methoxypropan-1-one |
| ~~~O~N=cyclohexyl | (2S)-1-(2-(2-(cyclohexylideneaminooxy)ethyl)-5-(2,5-difluorophenyl)-2-phenyl-1,3,4-thiadiazol-3(2H)-yl)-2-methoxypropan-1-one |
| ~~~O~N=CH-Ph | (E)-benzaldehyde O-2-(5-(2,5-difluorophenyl)-3-((S)-2-methoxypropanoyl)-2-phenyl-2,3-dihydro-1,3,4-thiadiazol-2-yl)ethyl oxime |
| ~~~NH-NH-C(CH₃)=NH | N'-(2-(5-(2,5-difluorophenyl)-3-((S)-2-methoxypropanoyl)-2-phenyl-2,3-dihydro-1,3,4-thiadiazol-2-yl)ethyl)acetimidohydrazide |

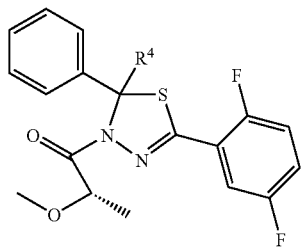

| R⁴ | Name |
|---|---|
| (hydrazinyl-C(=NMe)CH₃ group) | N'-(2-(5-(2,5-difluorophenyl)-3-((S)-2-methoxypropanoyl)-2-phenyl-2,3-dihydro-1,3,4-thiadiazol-2-yl)ethyl)-N'-methylacetimidohydrazide |
| (hydrazinyl-C(=N-C(=O)CH₃)CH₃ group) | N-(1-(2-(2-(5-(2,5-difluorophenyl)-3-((S)-2-methoxypropanoyl)-2-phenyl-2,3-dihydro-1,3,4-thiadiazol-2-yl)ethyl)hydrazinyl)ethylidene)acetamide |
| (N-methylhydrazinyl acetimidoyl group) | N'-(2-(5-(2,5-difluorophenyl)-3-((S)-2-methoxypropanoyl)-2-phenyl-2,3-dihydro-1,3,4-thiadiazol-2-yl)ethyl)-N'-methylacetimidohydrazide |
| (hydrazinyl guanidine group) | 2-(2-(5-(2,5-difluorophenyl)-3-((S)-2-methoxypropanoyl)-2-phenyl-2,3-dihydro-1,3,4-thiadiazol-2-yl)ethyl)hydrazinecarboximidamide |
| (hydrazinyl N-methylguanidine group) | 2-(2-(5-(2,5-difluorophenyl)-3-((S)-2-methoxypropanoyl)-2-phenyl-2,3-dihydro-1,3,4-thiadiazol-2-yl)ethyl)-N-methylhydrazinecarboximidamide |
| (acetylated hydrazinyl guanidine group) | N-((2-(2-(5-(2,5-difluorophenyl)-3-((S)-2-methoxypropanoyl)-2-phenyl-2,3-dihydro-1,3,4-thiadiazol-2-yl)ethyl)hydrazinyl)(imino)methyl)acetamide |
| (hydrazinyl tetrahydropyrimidinyl group) | (2S)-1-(5-(2,5-difluorophenyl)-2-phenyl-2-(2-(2-(1,4,5,6-tetrahydropyrimidin-2-yl)hydrazinyl)ethyl)-1,3,4-thiadiazol-3(2H)-yl)-2-methoxypropan-1-one |

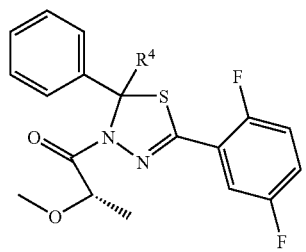

| R⁴ | Name |
|---|---|
| 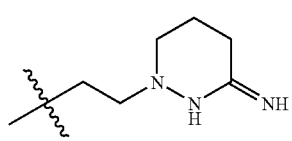 | (2S)-1-(5-(2,5-difluorophenyl)-2-(2-(3-iminopiperazin-1-yl)ethyl)-2-phenyl-1,3,4-thiadiazol-3(2H)-yl)-2-methoxypropan-1-one |

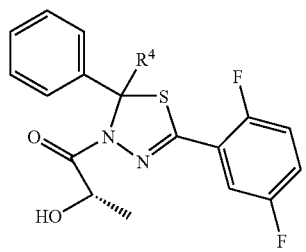

| R⁴ | Name |
|---|---|
| 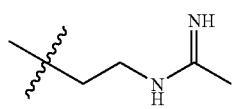 | N-(2-(5-(2,5-difluorophenyl)-3-((S)-2-hydroxypropanoyl)-2-phenyl-2,3-dihydro-1,3,4-thiadiazol-2-yl)ethyl)acetimidamide |
| 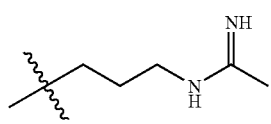 | N-(3-(5-(2,5-difluorophenyl)-3-((S)-2-hydroxypropanoyl)-2-phenyl-2,3-dihydro-1,3,4-thiadiazol-2-yl)propyl)acetimidamide |
| 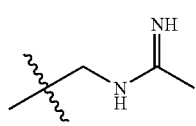 | N-((5-(2,5-difluorophenyl)-3-((S)-2-hydroxypropanoyl)-2-phenyl-2,3-dihydro-1,3,4-thiadiazol-2-yl)methyl)acetimidamide |
| 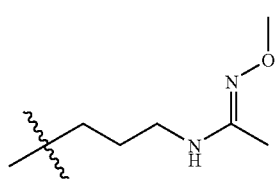 | N-(3-(5-(2,5-difluorophenyl)-3-((S)-2-hydroxypropanoyl)-2-phenyl-2,3-dihydro-1,3,4-thiadiazol-2-yl)propyl)-N'-methoxyacetimidamide |
| 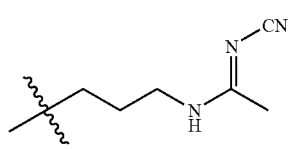 | N'-cyano-N-(3-(5-(2,5-difluorophenyl)-3-((S)-2-hydroxypropanoyl)-2-phenyl-2,3-dihydro-1,3,4-thiadiazol-2-yl)propyl)acetimidamide |

-continued

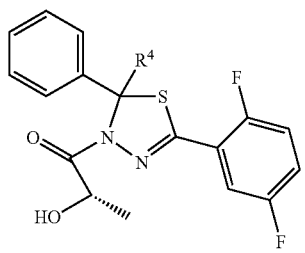

| R⁴ | Name |
|---|---|
| (CH₂)₃NH-C(=NH)-CH₂F | N-(3-(5-(2,5-difluorophenyl)-3-((S)-2-hydroxypropanoyl)-2-phenyl-2,3-dihydro-1,3,4-thiadiazol-2-yl)propyl)-2-fluoroacetimidamide |
| (CH₂)₃NH-C(NH₂)=CH-NO₂ | (2S)-1-(2-(3-((E)-1-amino-2-nitrovinylamino)propyl)-5-(2,5-difluorophenyl)-2-phenyl-1,3,4-thiadiazol-3(2H)-yl)-2-hydroxypropan-1-one |
| (CH₂)₃NH-C(NH₂)=N-CN | 2-cyano-1-(3-(5-(2,5-difluorophenyl)-3-((S)-2-hydroxypropanoyl)-2-phenyl-2,3-dihydro-1,3,4-thiadiazol-2-yl)propyl)guanidine |
| (CH₂)₂NH-C(NH₂)=N-CN | 2-cyano-1-(2-(5-(2,5-difluorophenyl)-3-((S)-2-hydroxypropanoyl)-2-phenyl-2,3-dihydro-1,3,4-thiadiazol-2-yl)ethyl)guanidine |
| CH₂NH-C(NH₂)=N-CN | 2-cyano-1-((5-(2,5-difluorophenyl)-3-((S)-2-hydroxypropanoyl)-2-phenyl-2,3-dihydro-1,3,4-thiadiazol-2-yl)methyl)guanidine |
| (CH₂)₃NH-C(NH₂)=N-C(=O)NH₂ | 1-(amino(3-(5-(2,5-difluorophenyl)-3-((S)-2-hydroxypropanoyl)-2-phenyl-2,3-dihydro-1,3,4-thiadiazol-2-yl)propylamino)methylene)urea |
| (CH₂)₂NH-C(NH₂)=N-CONH₂ | 1-(amino(2-(5-(2,5-difluorophenyl)-3-((S)-2-hydroxypropanoyl)-2-phenyl-2,3-dihydro-1,3,4-thiadiazol-2-yl)ethylamino)methylene)urea |
| CH₂NH-C(NH₂)=N-CONH₂ | 1-(amino((5-(2,5-difluorophenyl)-3-((S)-2-hydroxypropanoyl)-2-phenyl-2,3-dihydro-1,3,4-thiadiazol-2-yl)methylamino)methylene)urea |

-continued

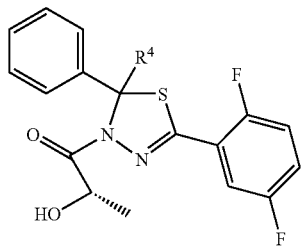

| R⁴ | Name |
|---|---|
| 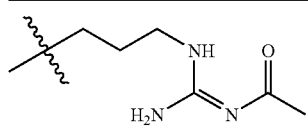 | N-(amino(3-(5-(2,5-difluorophenyl)-3-((S)-2-hydroxypropanoyl)-2-phenyl-2,3-dihydro-1,3,4-thiadiazol-2-yl)propylamino)methylene)acetamide |
| 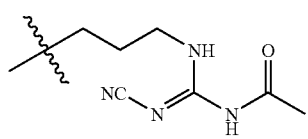 | N-(cyanamido(3-(5-(2,5-difluorophenyl)-3-((S)-2-hydroxypropanoyl)-2-phenyl-2,3-dihydro-1,3,4-thiadiazol-2-yl)propylamino)methylene)acetamide |
| 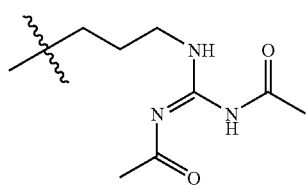 | N,N'-((3-(5-(2,5-difluorophenyl)-3-((S)-2-hydroxypropanoyl)-2-phenyl-2,3-dihydro-1,3,4-thiadiazol-2-yl)propylamino)methylene)diacetamide |
| 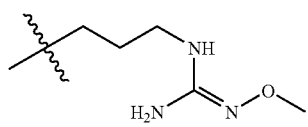 | 1-(3-(5-(2,5-difluorophenyl)-3-((S)-2-hydroxypropanoyl)-2-phenyl-2,3-dihydro-1,3,4-thiadiazol-2-yl)propyl)-2-methoxyguanidine |
| 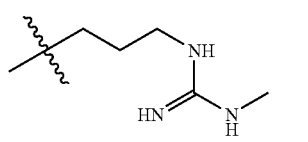 | 1-(3-(5-(2,5-difluorophenyl)-3-((S)-2-hydroxypropanoyl)-2-phenyl-2,3-dihydro-1,3,4-thiadiazol-2-yl)propyl)-3-methylguanidine |
| 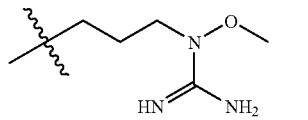 | 1-(3-(5-(2,5-difluorophenyl)-3-((S)-2-hydroxypropanoyl)-2-phenyl-2,3-dihydro-1,3,4-thiadiazol-2-yl)propyl)-1-methoxyguanidine |
| 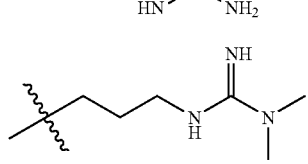 | 3-(3-(5-(2,5-difluorophenyl)-3-((S)-2-hydroxypropanoyl)-2-phenyl-2,3-dihydro-1,3,4-thiadiazol-2-yl)propyl)-1,1-dimethylguanidine |
| 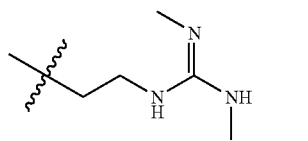 | 1-(3-(5-(2,5-difluorophenyl)-3-((S)-2-hydroxypropanoyl)-2-phenyl-2,3-dihydro-1,3,4-thiadiazol-2-yl)propyl)-2,3-dimethylguanidine |
| 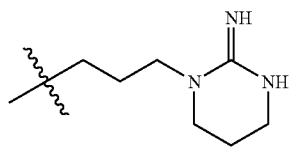 | (2S)-1-(5-(2,5-difluorophenyl)-2-(3-(2-iminotetrahydropyrimidin-1(2H)-yl)propyl)-2-phenyl-1,3,4-thiadiazol-3(2H)-yl)-2-hydroxypropan-1-one |

-continued

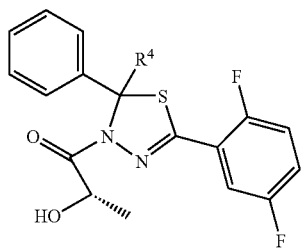

| R⁴ | Name |
|---|---|
| (tetrahydropyrimidin-2-ylamino structure) | (2S)-1-(5-(2,5-difluorophenyl)-2-phenyl-2-(3-(1,4,5,6-tetrahydropyrimidin-2-ylamino)propyl)-1,3,4-thiadiazol-3(2H)-yl)-2-hydroxypropan-1-one |
| (pyrrolidine carboximidamide structure) | N-(3-(5-(2,5-difluorophenyl)-3-((S)-2-hydroxypropanoyl)-2-phenyl-2,3-dihydro-1,3,4-thiadiazol-2-yl)propyl)pyrrolidine-1-carboximidamide |
| (butanimidamide structure) | 4-(5-(2,5-difluorophenyl)-3-((S)-2-hydroxypropanoyl)-2-phenyl-2,3-dihydro-1,3,4-thiadiazol-2-yl)butanimidamide |
| (pentanimidamide structure) | 5-(5-(2,5-difluorophenyl)-3-((S)-2-hydroxypropanoyl)-2-phenyl-2,3-dihydro-1,3,4-thiadiazol-2-yl)pentanimidamide |
| (propanimidamide structure) | 3-(5-(2,5-difluorophenyl)-3-((S)-2-hydroxypropanoyl)-2-phenyl-2,3-dihydro-1,3,4-thiadiazol-2-yl)propanimidamide |
| (N'-methoxybutanimidamide structure) | 4-(5-(2,5-difluorophenyl)-3-((S)-2-hydroxypropanoyl)-2-phenyl-2,3-dihydro-1,3,4-thiadiazol-2-yl)-N'-methoxybutanimidamide |
| (N'-cyano butanimidamide structure) | N'-cyano-4-(5-(2,5-difluorophenyl)-3-((S)-2-hydroxypropanoyl)-2-phenyl-2,3-dihydro-1,3,4-thiadiazol-2-yl)butanimidamide |
| (2,2-difluorobutanimidamide structure) | 4-(5-(2,5-difluorophenyl)-3-((S)-2-hydroxypropanoyl)-2-phenyl-2,3-dihydro-1,3,4-thiadiazol-2-yl)-2,2-difluorobutanimidamide |
| (methoxy acetimidamide structure) | 2-((5-(2,5-difluorophenyl)-3-((S)-2-hydroxypropanoyl)-2-phenyl-2,3-dihydro-1,3,4-thiadiazol-2-yl)methoxy)acetimidamide |
| (N-methylbutanimidamide structure) | 4-(5-(2,5-difluorophenyl)-3-((S)-2-hydroxypropanoyl)-2-phenyl-2,3-dihydro-1,3,4-thiadiazol-2-yl)-N-methylbutanimidamide |

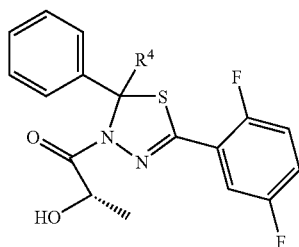

| R⁴ | Name |
|---|---|
| 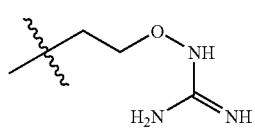 | 1-(2-(5-(2,5-difluorophenyl)-3-((S)-2-hydroxypropanoyl)-2-phenyl-2,3-dihydro-1,3,4-thiadiazol-2-yl)ethoxy)guanidine |
| 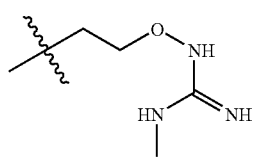 | 1-(2-(5-(2,5-difluorophenyl)-3-((S)-2-hydroxypropanoyl)-2-phenyl-2,3-dihydro-1,3,4-thiadiazol-2-yl)ethoxy)-3-methylguanidine |
| 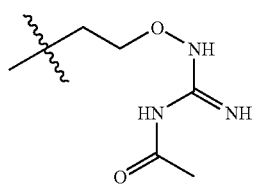 | N-(N-(2-(5-(2,5-difluorophenyl)-3-((S)-2-hydroxypropanoyl)-2-phenyl-2,3-dihydro-1,3,4-thiadiazol-2-yl)ethoxy)carbamimidoyl)acetamide |
| 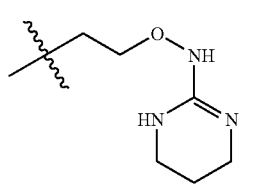 | (2S)-1-(5-(2,5-difluorophenyl)-2-phenyl-2-(2-(1,4,5,6-tetrahydropyrimidin-2-ylaminooxy)ethyl)-1,3,4-thiadiazol-3-(2H)-yl)-2-hydroxypropan-1-one |
| 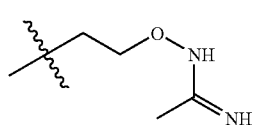 | N-(2-(5-(2,5-difluorophenyl)-3-((S)-2-hydroxypropanoyl)-2-phenyl-2,3-dihydro-1,3,4-thiadiazol-2-yl)ethoxy)acetimidamide |
| 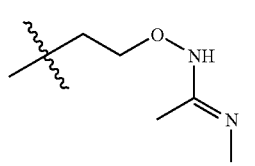 | (E)-N-(2-(5-(2,5-difluorophenyl)-3-((S)-2-hydroxypropanoyl)-2-phenyl-2,3-dihydro-1,3,4-thiadiazol-2-yl)ethoxy)-N'-methylacetimidamide |
| 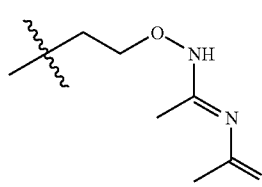 | N-(1-(2-(5-(2,5-difluorophenyl)-3-((S)-2-hydroxypropanoyl)-2-phenyl-2,3-dihydro-1,3,4-thiadiazol-2-yl)ethoxyamino)ethylidene)acetamide |
| 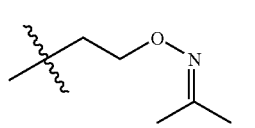 | (2S)-1-(5-(2,5-difluorophenyl)-2-phenyl-2-(2-(propan-2-ylideneaminooxy)ethyl)-1,3,4-thiadiazol-3(2H)-yl)-2-hydroxypropan-1-one |

-continued

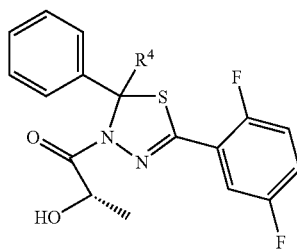

| R⁴ | Name |
|---|---|
| 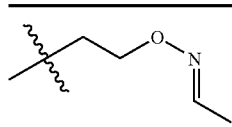 | (E)-acetaldehyde O-2-(5-(2,5-difluorophenyl)-3-((S)-2-hydroxypropanoyl)-2-phenyl-2,3-dihydro-1,3,4-thiadiazol-2-yl)ethyl oxime |
| 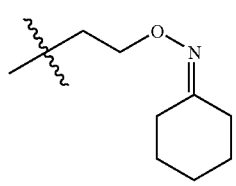 | (2S)-1-(2-(2-(cyclohexylideneaminooxy)ethyl)-5-(2,5-difluorophenyl)-2-phenyl-1,3,4-thiadiazol-3(2H)-yl)-2-hydroxypropan-1-one |
| 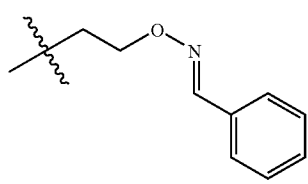 | (E)-benzaldehyde O-2-(5-(2,5-difluorophenyl)-3-((S)-2-hydroxypropanoyl)-2-phenyl-2,3-dihydro-1,3,4-thiadiazol-2-yl)ethyl oxime |
| 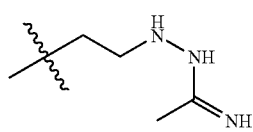 | N'-(2-(5-(2,5-difluorophenyl)-3-((S)-2-hydroxypropanoyl)-2-phenyl-2,3-dihydro-1,3,4-thiadiazol-2-yl)ethyl)acetimidohydrazide |
| 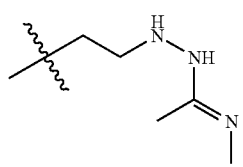 | N'-(2-(5-(2,5-difluorophenyl)-3-((S)-2-hydroxypropanoyl)-2-phenyl-2,3-dihydro-1,3,4-thiadiazol-2-yl)ethyl)-N'-methylacetimidohydrazide |
| 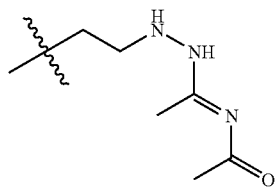 | N-(1-(2-(2-(5-(2,5-difluorophenyl)-3-((S)-2-hydroxypropanoyl)-2-phenyl-2,3-dihydro-1,3,4-thiadiazol-2-yl)ethyl)hydrazinyl)ethylidene)acetamide |
| 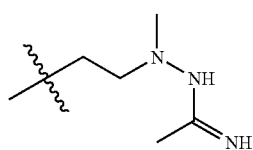 | N'-(2-(5-(2,5-difluorophenyl)-3-((S)-2-hydroxypropanoyl)-2-phenyl-2,3-dihydro-1,3,4-thiadiazol-2-yl)ethyl)-N'-methylacetimidohydrazide |
| 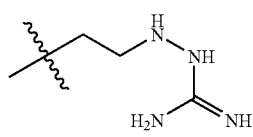 | 2-(2-(5-(2,5-difluorophenyl)-3-((S)-2-hydroxypropanoyl)-2-phenyl-2,3-dihydro-1,3,4-thiadiazol-2-yl)ethyl)hydrazinecarboximidamide |

-continued

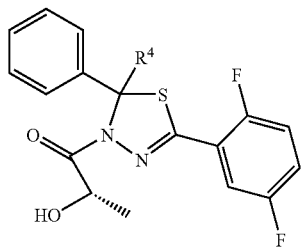

| R⁴ | Name |
|---|---|
| | 2-(2-(5-(2,5-difluorophenyl)-3-((S)-2-hydroxypropanoyl)-2-phenyl-2,3-dihydro-1,3,4-thiadiazol-2-yl)ethyl)-N-methylhydrazinecarboximidamide |
| | N-((2-(2-(5-(2,5-difluorophenyl)-3-((S)-2-hydroxypropanoyl)-2-phenyl-2,3-dihydro-1,3,4-thiadiazol-2-yl)ethyl)hydrazinyl)(imino)methyl)acetamide |
| | (2S)-1-(5-(2,5-difluorophenyl)-2-phenyl-2-(2-(2-(1,4,5,6-tetrahydropyrimidin-2-yl)hydrazinyl)ethyl)-1,3,4-thiadiazol-3(2H)-yl)-2-hydroxypropan-1-one |
| | (2S)-1-(5-(2,5-difluorophenyl)-2-(2-(3-iminopiperazin-1-yl)ethyl)-2-phenyl-1,3,4-thiadiazol-3(2H)-yl)-2-hydroxypropan-1-one |

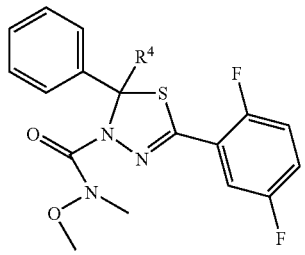

| R⁴ | Name |
|---|---|
| | 2-(2-acetimidamidoethyl)-5-(2,5-difluorophenyl)-N-methoxy-N-methyl-2-phenyl-1,3,4-thiadiazole-3(2H)-carboxamide |
| | 2-(3-acetimidamidopropyl)-5-(2,5-difluorophenyl)-N-methoxy-N-methyl-2-phenyl-1,3,4-thiadiazole-3(2H)-carboxamide |

-continued

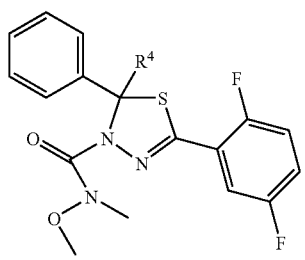

| R⁴ | Name |
|---|---|
| 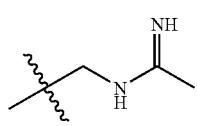 | 2-(acetimidamidomethyl)-5-(2,5-difluorophenyl)-N-methoxy-N-methyl-2-phenyl-1,3,4-thiadiazole-3(2H)-carboxamide |
| 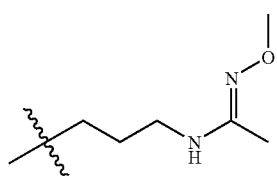 | 5-(2,5-difluorophenyl)-N-methoxy-2-(3-(N'-methoxyacetimidamido)propyl)-N-methyl-2-phenyl-1,3,4-thiadiazole-3(2H)-carboxamide |
| 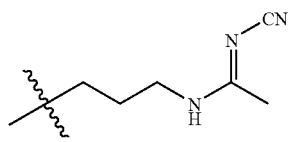 | 2-(3-(N'-cyanoacetimidamido)propyl)-5-(2,5-difluorophenyl)-N-methoxy-N-methyl-2-phenyl-1,3,4-thiadiazole-3(2H)-carboxamide |
| 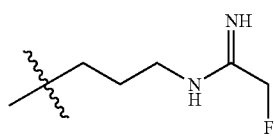 | 5-(2,5-difluorophenyl)-2-(3-(2-fluoroacetimidamido)propyl)-N-methoxy-N-methyl-2-phenyl-1,3,4-thiadiazole-3(2H)-carboxamide |
| 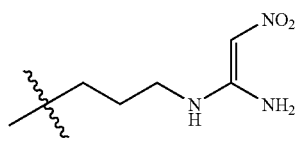 | (E)-2-(3-(1-amino-2-nitrovinylamino)propyl)-5-(2,5-difluorophenyl)-N-methoxy-N-methyl-2-phenyl-1,3,4-thiadiazole-3(2H)-carboxamide |
| 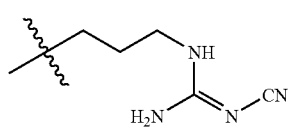 | 2-(3-(2-cyanoguanidino)propyl)-5-(2,5-difluorophenyl)-N-methoxy-N-methyl-2-phenyl-1,3,4-thiadiazole-3(2H)-carboxamide |
| 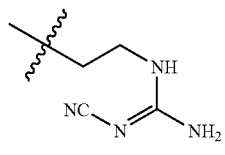 | 2-(2-(2-cyanoguanidino)ethyl)-5-(2,5-difluorophenyl)-N-methoxy-N-methyl-2-phenyl-1,3,4-thiadiazole-3(2H)-carboxamide |
| 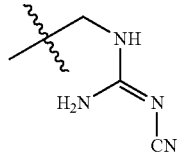 | 2-((2-cyanoguanidino)methyl)-5-(2,5-difluorophenyl)-N-methoxy-N-methyl-2-phenyl-1,3,4-thiadiazole-3(2H)-carboxamide |

-continued

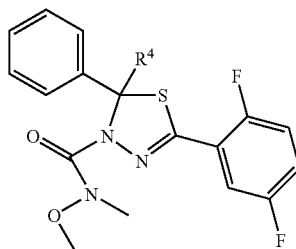

| R⁴ | Name |
|---|---|
| 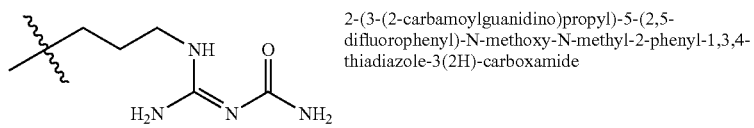 | 2-(3-(2-carbamoylguanidino)propyl)-5-(2,5-difluorophenyl)-N-methoxy-N-methyl-2-phenyl-1,3,4-thiadiazole-3(2H)-carboxamide |
| 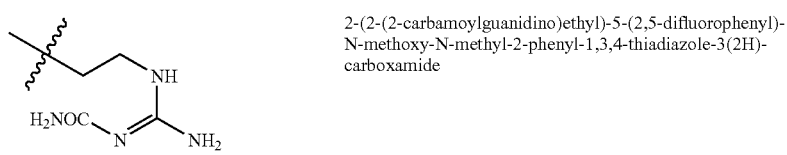 | 2-(2-(2-carbamoylguanidino)ethyl)-5-(2,5-difluorophenyl)-N-methoxy-N-methyl-2-phenyl-1,3,4-thiadiazole-3(2H)-carboxamide |
| 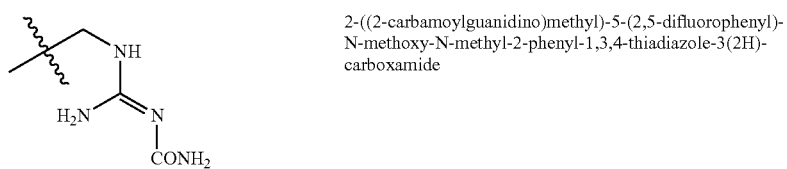 | 2-((2-carbamoylguanidino)methyl)-5-(2,5-difluorophenyl)-N-methoxy-N-methyl-2-phenyl-1,3,4-thiadiazole-3(2H)-carboxamide |
| 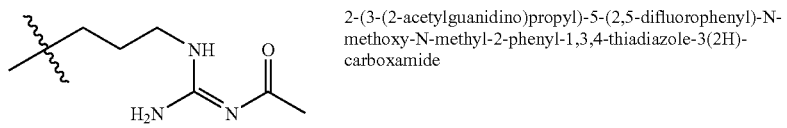 | 2-(3-(2-acetylguanidino)propyl)-5-(2,5-difluorophenyl)-N-methoxy-N-methyl-2-phenyl-1,3,4-thiadiazole-3(2H)-carboxamide |
| 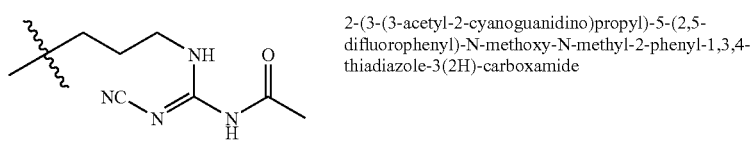 | 2-(3-(3-acetyl-2-cyanoguanidino)propyl)-5-(2,5-difluorophenyl)-N-methoxy-N-methyl-2-phenyl-1,3,4-thiadiazole-3(2H)-carboxamide |
| 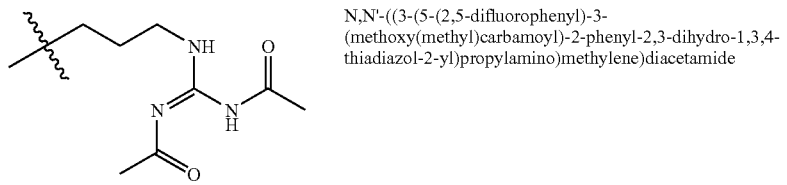 | N,N'-((3-(5-(2,5-difluorophenyl)-3-(methoxy(methyl)carbamoyl)-2-phenyl-2,3-dihydro-1,3,4-thiadiazol-2-yl)propylamino)methylene)diacetamide |
| 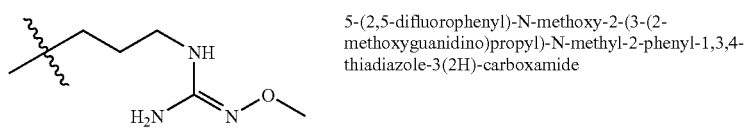 | 5-(2,5-difluorophenyl)-N-methoxy-2-(3-(2-methoxyguanidino)propyl)-N-methyl-2-phenyl-1,3,4-thiadiazole-3(2H)-carboxamide |
| 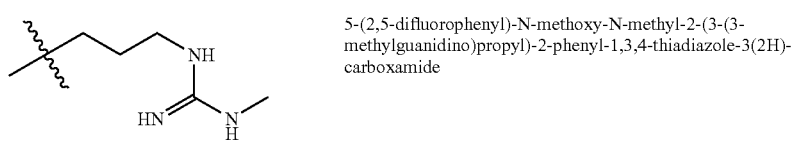 | 5-(2,5-difluorophenyl)-N-methoxy-N-methyl-2-(3-(3-methylguanidino)propyl)-2-phenyl-1,3,4-thiadiazole-3(2H)-carboxamide |

-continued

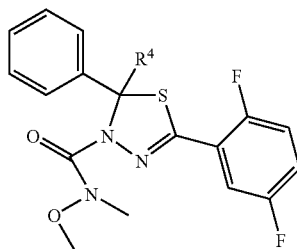

| R⁴ | Name |
|---|---|
| (butyl-N(OMe)-C(=NH)NH₂) | 5-(2,5-difluorophenyl)-N-methoxy-2-(3-(1-methoxyguanidino)propyl)-N-methyl-2-phenyl-1,3,4-thiadiazole-3(2H)-carboxamide |
| (propyl-NH-C(=NH)-N(Me)₂) | 5-(2,5-difluorophenyl)-2-(3-(3,3-dimethylguanidino)propyl)-N-methyl-N-methyl-2-phenyl-1,3,4-thiadiazole-3(2H)-carboxamide |
| (propyl-NH-C(=NMe)-NHMe) | 5-(2,5-difluorophenyl)-2-(3-(2,3-dimethylguanidino)propyl)-N-methyl-N-methyl-2-phenyl-1,3,4-thiadiazole-3(2H)-carboxamide |
| (propyl-tetrahydropyrimidin-2-imine) | 5-(2,5-difluorophenyl)-2-(3-(2-iminotetrahydropyrimidin-1(2H)-yl)propyl)-N-methoxy-N-methyl-2-phenyl-1,3,4-thiadiazole-3(2H)-carboxamide |
| (propyl-NH-tetrahydropyrimidin-2-yl) | 5-(2,5-difluorophenyl)-N-methoxy-N-methyl-2-phenyl-2-(3-(1,4,5,6-tetrahydropyrimidin-2-ylamino)propyl)-1,3,4-thiadiazole-3(2H)-carboxamide |
| (propyl-NH-C(=NH)-pyrrolidine) | 5-(2,5-difluorophenyl)-N-methoxy-N-methyl-2-phenyl-2-(3-(pyrrolidine-1-carboximidamido)propyl)-1,3,4-thiadiazole-3(2H)-carboxamide |
| (butyl-C(=NH)NH₂) | 2-(4-amino-4-iminobutyl)-5-(2,5-difluorophenyl)-N-methoxy-N-methyl-2-phenyl-1,3,4-thiadiazole-3(2H)-carboxamide |
| (pentyl-C(=NH)NH₂) | 2-(5-amino-5-iminopentyl)-5-(2,5-difluorophenyl)-N-methoxy-N-methyl-2-phenyl-1,3,4-thiadiazole-3(2H)-carboxamide |
| (propyl-C(=NH)NH₂) | 2-(3-amino-3-iminopropyl)-5-(2,5-difluorophenyl)-N-methoxy-N-methyl-2-phenyl-1,3,4-thiadiazole-3(2H)-carboxamide |

-continued

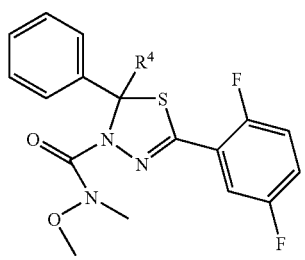

| R⁴ | Name |
|---|---|
| 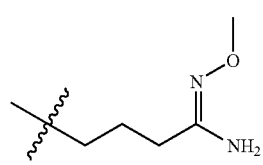 | 2-(4-amino-4-(methoxyimino)butyl)-5-(2,5-difluorophenyl)-N-methoxy-N-methyl-2-phenyl-1,3,4-thiadiazole-3(2H)-carboxamide |
| 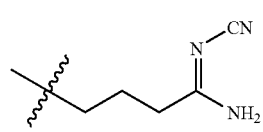 | 2-(4-amino-4-(cyanoimino)butyl)-5-(2,5-difluorophenyl)-N-methoxy-N-methyl-2-phenyl-1,3,4-thiadiazole-3(2H)-carboxamide |
| 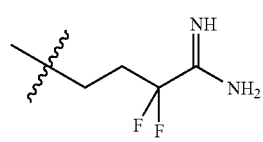 | 2-(4-amino-3,3-difluoro-4-iminobutyl)-5-(2,5-difluorophenyl)-N-methoxy-N-methyl-2-phenyl-1,3,4-thiadiazole-3(2H)-carboxamide |
| 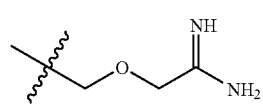 | 2-((2-amino-2-iminoethoxy)methyl)-5-(2,5-difluorophenyl)-N-methoxy-N-methyl-2-phenyl-1,3,4-thiadiazole-3(2H)-carboxamide |
| 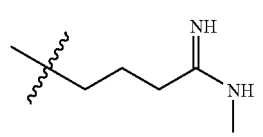 | 5-(2,5-difluorophenyl)-2-(4-imino-4-(methylamino)butyl)-N-methoxy-N-methyl-2-phenyl-1,3,4-thiadiazole-3(2H)-carboxamide |
| 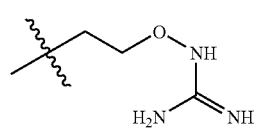 | 5-(2,5-difluorophenyl)-2-(2-(guanidinooxy)ethyl)-N-methoxy-N-methyl-2-phenyl-1,3,4-thiadiazole-3(2H)-carboxamide |
| 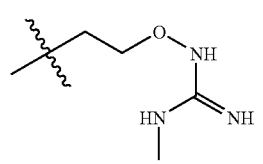 | 5-(2,5-difluorophenyl)-N-methoxy-N-methyl-2-(2-(3-methylguanidinooxy)ethyl)-2-phenyl-1,3,4-thiadiazole-3(2H)-carboxamide |
| 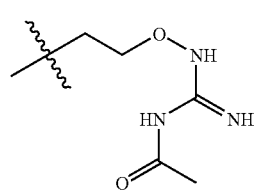 | 2-(2-(3-acetylguanidinooxy)ethyl)-5-(2,5-difluorophenyl)-N-methoxy-N-methyl-2-phenyl-1,3,4-thiadiazole-3(2H)-carboxamide |

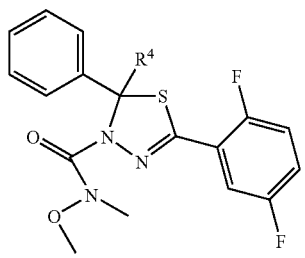

| R⁴ | Name |
|---|---|
| 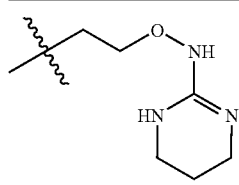 | 5-(2,5-difluorophenyl)-N-methoxy-N-methyl-2-phenyl-2-(2-(1,4,5,6-tetrahydropyrimidin-2-ylaminooxy)ethyl)-1,3,4-thiadiazole-3(2H)-carboxamide |
| 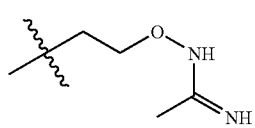 | 2-(2-(acetimidamidooxy)ethyl)-5-(2,5-difluorophenyl)-N-methoxy-N-methyl-2-phenyl-1,3,4-thiadiazole-3(2H)-carboxamide |
| 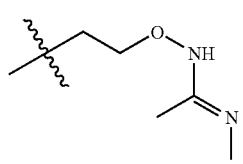 | 5-(2,5-difluorophenyl)-N-methoxy-N-methyl-2-(2-(N'-methylacetimidamidooxy)ethyl)-2-phenyl-1,3,4-thiadiazole-3(2H)-carboxamide |
| 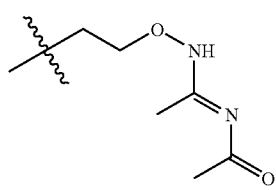 | 2-(2-(N'-acetylacetimidamidooxy)ethyl)-5-(2,5-difluorophenyl)-N-methoxy-N-methyl-2-phenyl-1,3,4-thiadiazole-3(2H)-carboxamide |
| 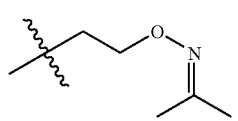 | 5-(2,5-difluorophenyl)-N-methoxy-N-methyl-2-phenyl-2-(2-(propan-2-ylideneaminooxy)ethyl)-1,3,4-thiadiazole-3(2H)-carboxamide |
| 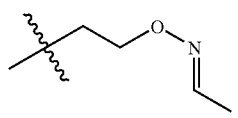 | (E)-5-(2,5-difluorophenyl)-2-(2-ethylideneaminooxy)ethyl)-N-methoxy-N-methyl-2-phenyl-1,3,4-thiadiazole-3(2H)-carboxamide |
| 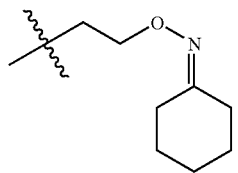 | 2-(2-(cyclohexylideneaminooxy)ethyl)-5-(2,5-difluorophenyl)-N-methoxy-N-methyl-2-phenyl-1,3,4-thiadiazole-3(2H)-carboxamide |
| 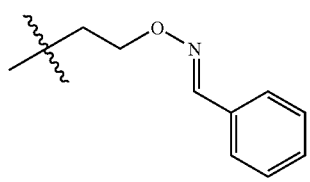 | (E)-2-(2-(benzylideneaminooxy)ethyl)-5-(2,5-difluorophenyl)-N-methoxy-N-methyl-2-phenyl-1,3,4-thiadiazole-3(2H)-carboxamide |

-continued

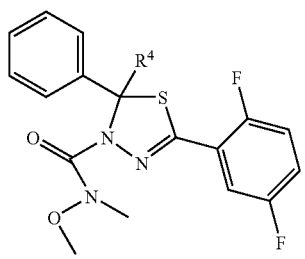

| R⁴ | Name |
|---|---|
| 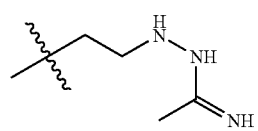 | 5-(2,5-difluorophenyl)-2-(2-(2-(1-iminoethyl)hydrazinyl)ethyl)-N-methoxy-N-methyl-2-phenyl-1,3,4-thiadiazole-3(2H)-carboxamide |
| 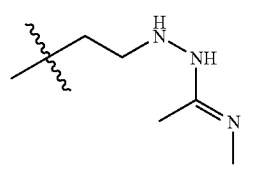 | 5-(2,5-difluorophenyl)-N-methoxy-N-methyl-2-(2-(2-(1-(methylimino)ethyl)hydrazinyl)ethyl)-2-phenyl-1,3,4-thiadiazole-3(2H)-carboxamide |
| 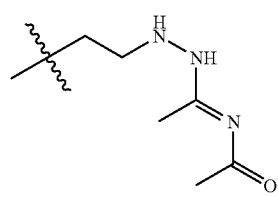 | 2-(2-(2-(1-(acetylimino)ethyl)hydrazinyl)ethyl)-5-(2,5-difluorophenyl)-N-methoxy-N-methyl-2-phenyl-1,3,4-thiadiazole-3(2H)-carboxamide |
| 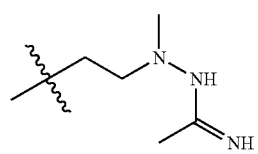 | 5-(2,5-difluorophenyl)-2-(2-(2-(1-iminoethyl)-1-methylhydrazinyl)ethyl)-N-methoxy-N-methyl-2-phenyl-1,3,4-thiadiazole-3(2H)-carboxamide |
| 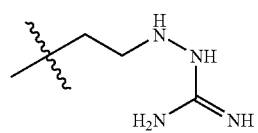 | 2-(2-(2-carbamimidoylhydrazinyl)ethyl)-5-(2,5-difluorophenyl)-N-methoxy-N-methyl-2-phenyl-1,3,4-thiadiazole-3(2H)-carboxamide |
| 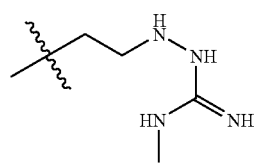 | 5-(2,5-difluorophenyl)-N-methoxy-N-methyl-2-(2-(2-(N-methylcarbamimidoyl)hydrazinyl)ethyl)-2-phenyl-1,3,4-thiadiazole-3(2H)-carboxamide |
| 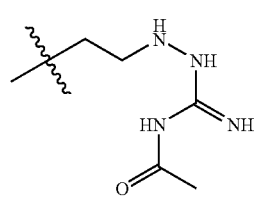 | 2-(2-(2-(N-acetylcarbamimidoyl)hydrazinyl)ethyl)-5-(2,5-difluorophenyl)-N-methoxy-N-methyl-2-phenyl-1,3,4-thiadiazole-3(2H)-carboxamide |

-continued

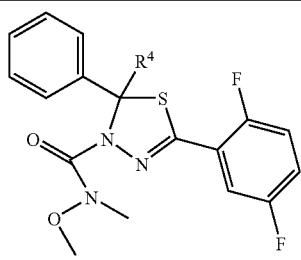

| R⁴ | Name |
|---|---|
| 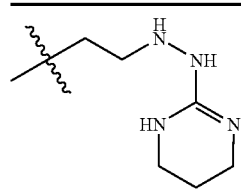 | 5-(2,5-difluorophenyl)-N-methoxy-N-methyl-2-phenyl-2-(2-(2-(1,4,5,6-tetrahydropyrimidin-2-yl)hydrazinyl)ethyl)-1,3,4-thiadiazole-3(2H)-carboxamide |
| 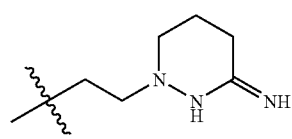 | 5-(2,5-difluorophenyl)-2-(2-(3-iminopiperazin-1-yl)ethyl)-N-methoxy-N-methyl-2-phenyl-1,3,4-thiadiazole-3(2H)-carboxamide |

Example 30

The following illustrate representative pharmaceutical dosage forms, containing a compound of Formula I ('Compound X'), for therapeutic or prophylactic use in humans.

| (i) Tablet 1 | mg/tablet |
|---|---|
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0 N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |
| 01 N Sodium hydroxide solution (pH adjustment to 7.0-7.5) | q.s. |
| Water for injection | q.s. ad 1 mL |

| (vi) Aerosol | mg/can |
|---|---|
| Compound X = | 20.0 |
| Oleic acid | 10.0 |
| Trichloromonofluoromethane | 5,000.0 |

-continued

| (vi) Aerosol | mg/can |
|---|---|
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The foregoing description is considered as illustrative only of the principles of the invention. Further, since numerous modifications and changes will be readily apparent to those skilled in the art, it is not desired to limit the invention to the exact construction and process shown as described above. Accordingly, all suitable modifications and equivalents may be considered to full within the scope of the invention as defined by the claims that follow.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

What is claimed is:
1. A compound of Formula I:

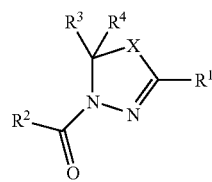

I or a salt thereof, wherein:
X is O or S;
$R^1$ and $R^3$ are each independently aryl or heteroaryl, wherein said aryl and heteroaryl are each optionally substituted with one or more groups independently selected from halo, cyano, nitro, fluoromethyl, difluoromethyl, trifluoromethyl, difluoromethoxy, trifluoromethoxy, azido, —$OR^a$, —$NR^aR^b$, —C(=O)$R^a$, —C(=O)$OR^a$, —$NR^aC$(=O)$OR^d$, —C(=O)$NR^aR^b$, ($C_1$-$C_{10}$)alkyl, ($C3$-$C_{10}$)cycloalkyl, ($C_2$-$C_{10}$)alkenyl, and ($C_2$-$C_{10}$)alkynyl;
$R^2$ is ($C_1$-$C_{10}$)alkyl, ($C_2$-$C_{10}$)alkenyl, ($C_2$-$C_{10}$)alkynyl, ($C_3$-$C_{10}$)cycloalkyl, $NR^jR^k$, aryl, heterocycle, or heteroaryl, wherein each ($C_1$-$C_{10}$)alkyl, ($C_2$-$C_{10}$)alkenyl, ($C_2$-$C_{10}$)alkynyl, ($C_3$-$C_{10}$)cycloalkyl, C(=$NR^h$)$R^i$, aryl, and heteroaryl of $R^2$ is optionally substituted with one or more $R^o$;
$R^4$ is Z—$NR^g$—C(=$NR^h$)$R^i$, Z—$NR^g$—C(=$NR^h$)$NR^jR^k$, Z—C(=$NR^h$)$NR^jR^k$, Z—O—$NR^gC$(=$NR^h$)$NR^jR^k$, Z—O—$NR^g$—C(=$NR^h$)$R^i$, Z—$NR^m$—$NR^n$—C(=$NR^h$)$R^i$, Z—O—$NR^jR^k$, Z—O—Z—C(=$NR^h$)$NR^jR^k$, Z—O—N=C($R^r$)$_2$, Z—$NR^g$—C(=$CHR^q$)$NR^jR^k$, or Z—$NR^m$—$NR^n$—C(=$NR^h$)$NR^jR^k$, provided that when $R^4$ is Z—O—$NR^gC$(=$NR^h$)$NR^jR^k$, Z—O—$NR^g$—C(=$NR^h$)$R^i$, or Z—O—$NR^jR^k$, then $R^j$ and $R^g$ are not $OR^p$;
Z is ($C_1$-$C_{10}$)alkylene, ($C_2$-$C_{10}$)alkenylene, or ($C_2$-$C_{10}$) alkynylene, each optionally substituted with one or more halo;
$R^a$, $R^b$, and $R^c$ are each independently selected from H, ($C_1$-$C_{10}$)alkyl, ($C_2$-$C_{10}$)alkenyl, ($C_2$-$C_{10}$)alkynyl, ($C_3$-$C_{10}$)cycloalkyl, aryl, heteroaryl, heterocycle and aryl($C_1$-$C_3$)alkyl, wherein each $R^a$ and $R^b$ is optionally substituted with one or more groups independently selected from oxo (with the proviso that it is not on an aromatic ring), halo, cyano, nitro, —$OR^e$, —$NR^eR^f$, difluoromethyl, trifluoromethyl, difluoromethoxy, trifluoromethoxy, azido, ($C_1$-$C_{10}$)alkyl, and ($C_3$-$C_{10}$)cycloalkyl; or any $NR^aR^b$ taken together form a heterocycle, wherein said heterocycle is optionally substituted with one or more groups independently selected from oxo (with the proviso that it is not on an aromatic ring), halo, cyano, nitro, $OR^e$, —$NR^eR^f$, difluoromethyl, trifluoromethyl, difluoromethoxy, trifluoromethoxy, azido, ($C_1$-$C_{10}$)alkyl, and ($C_3$-$C_{10}$)cycloalkyl; or any $NR^bR^c$ taken together form a heterocyclic ring, wherein said heterocycle ring is optionally substituted with one or more oxo (with the proviso that it is not on an aromatic ring), halo, cyano, nitro, $OR^e$, —$NR^eR^f$, difluoromethyl, trifluoromethyl, difluoromethoxy, trifluoromethoxy, azido, ($C_1$-$C_{10}$)alkyl, and ($C_3$-$C_{10}$)cycloalkyl; or $R^a$ and $R^d$ together with the atoms to which they are attached form a heterocycle; or $R^a$ and $R^g$ together with the atoms to which they are attached form a heterocycle;
$R^d$ is ($C_1$-$C_{10}$)alkyl, ($C_2$-$C_{10}$)alkenyl, ($C_3$-$C_{10}$)cycloalkyl, aryl, heteroaryl, heterocycle or aryl($C_1$-$C_3$)alkyl, wherein each $R^d$ is optionally substituted with one or more groups independently selected from oxo (with the proviso that it is not on an aromatic ring), halo, cyano, nitro, $OR^e$, —$NR^eR^f$, difluoromethyl, trifluoromethyl, difluoromethoxy, trifluoromethoxy, azido, ($C_1$-$C_{10}$) alkyl, and ($C_3$-$C_{10}$)cycloalkyl; or $R^a$ and $R^d$ together with the atoms to which they are attached form a heterocycle;
$R^e$ and $R^f$ are independently selected from H, ($C_1$-$C_{10}$) alkyl, ($C_2$-$C_{10}$)alkenyl, ($C_2$-$C_{10}$)alkynyl, and ($C_3$-$C_{10}$) cycloalkyl; or $NR^eR^f$ taken together form a heterocycle;
$R^g$, $R^m$ and $R^n$ are independently H, $OR^p$, or ($C_1$-$C_{10}$)alkyl; or $R^i$ and $R^m$ together with the atoms to which they are attached form a heterocycle; or $R^g$ and $R^j$ together with the atoms to which they are attached form a heterocycle; or $R^a$ and $R^g$ together with the atoms to which they are attached form a heterocycle; or $R^i$ and $R^n$ together with the atoms to which they are attached form a heterocycle; or $R^m$ and $R^n$ together with the atoms to which they are attached form a heterocycle; or $R^j$ and $R^m$ together with the atoms to which they are attached form a heterocycle; or $R^j$ and $R^n$ together with the atoms to which they are attached form a heterocycle;
$R^h$ is H, —$OR^p$, cyano, —C(=O)N($R^p$)$_2$, —C(=O)$R^p$, or alkyl optionally substituted with one or more groups independently selected from halo, cyano, —$OR^p$, —N($R^p$)$_2$, and aryl; or $R^h$ and $R^j$ together with the atoms to which they are attached form a heterocycle; or $R^h$ and $R^i$ together with the atoms to which they are attached form a heterocycle;
$R^i$ is H or ($C_1$-$C_{10}$)alkyl optionally substituted with one or more groups independently selected from halo, nitro, cyano, —$OR^p$, —N($R^p$)$_2$, and aryl; or $R^i$ and $R^m$ together with the atoms to which they are attached form a heterocycle; or $R^h$ and $R^i$ together with the atoms to which they are attached form a heterocycle; or $R^i$ and $R^n$ together with the atoms to which they are attached form a heterocycle;
$R^j$ and $R^k$ are independently H, —$OR^p$, C(=O)$R^p$, heterocycle, aryl, heteroaryl, ($C_3$-$C_6$)cycloalkyl or ($C_1$-$C_{10}$)

alkyl optionally substituted with one or more groups independently selected from halo, cyano, —OR$^p$, —N(R$^p$)$_2$, and aryl; or —NR$^j$R$^k$ together form a heterocycle; or R$^g$ and R$^j$ together with the atoms to which they are attached form a heterocycle; or R$^h$ and R$^j$ together with the atoms to which they are attached form a heterocycle; or R$^j$ and R$^k$ together with the atoms to which they are attached form a heterocycle; or R$^j$ and R$^m$ together with the atoms to which they are attached form a heterocycle; or R$^j$ and R$^n$ together with the atoms to which they are attached form a heterocycle;

each R$^o$ is independently oxo (provided it is not on a nitrogen, oxygen or an unsaturated carbon), halo, cyano, nitro, azido, —NR$^a$R$^b$, —C(=O)R$^a$, —C(O)OR$^a$, —OC(=O)R$^a$, —NR$^a$C(=O)OR$^d$, —C(=O)NR$^a$R$^b$, —NR$^a$C(=O)NR$^b$(OR$^c$), —NR$^a$C(=O)NR$^b$R$^c$, —NR$^a$C(NCN)NR$^b$R$^c$, —OR$^a$, (C$_1$-C$_{10}$)alkyl, (C$_3$-C$_{10}$)cycloalkyl, (C$_2$-C$_{10}$)alkenyl, (C$_2$-C$_{10}$)alkynyl, aryl, heteroaryl, aryl(C$_1$-C$_3$)alkyl, heteroaryl(C$_1$-C$_3$)alkyl, heterocycle, heterocycle(C$_1$-C$_3$)alkyl, or —OP(=O)(OR$^a$)$_2$, wherein said (C$_1$-C$_{10}$)alkyl, (C$_3$-C$_{10}$)cycloalkyl, (C$_2$-C$_{10}$)alkenyl, (C$_2$-C$_{10}$)alkynyl, aryl, heteroaryl, aryl(C$_1$-C$_3$)alkyl, heteroaryl(C$_1$-C$_3$)alkyl, heterocycle and heterocycle(C$_1$-C$_3$)alkyl are optionally substituted with one or more groups independently selected from oxo (with the proviso that it is not on an aromatic ring), halo, cyano, nitro, hydroxy, —OR$^a$, NR$^a$R$^b$, difluoromethyl, trifluoromethyl, difluoromethoxy, trifluoromethoxy, azido, —C(=O)R$^a$, —C(=O)OR$^a$, —OC(=O)R$^a$, —NR$^a$C(=O)OR$^b$, —C(=O)NR$^a$R$^b$, —NR$^a$C(=O)NR$^b$R$^c$, and —NR$^a$C(NCN)NR$^b$R$^c$;

each R$^p$ is independently H, (C$_1$-C$_{10}$)alkyl, —P(=O)(OH)$_2$, acetyl, 2-aminopropanoyl, aminoacetyl, or methoxycarbonyl;

each R$^q$ is independently (C$_1$-C$_{10}$)alkyl, (C$_2$-C$_{10}$)alkenyl, (C$_2$-C$_{10}$)alkynyl, (C$_3$-C$_{10}$)cycloalkyl, halo, cyano, nitro, —NR$^a$R$^b$, —C(=O)R$^p$, or OR$^p$; and each R$^r$ is independently (C$_1$-C$_{10}$)alkyl, (C$_2$-C$_{10}$)alkenyl, (C$_2$-C$_{10}$)alkynyl, (C$_3$-C$_{10}$)cycloalkyl, aryl, or aryl(C$_1$-C$_3$)alkyl; or —C(R$^r$)$_2$ together form a (C$_3$-C$_{10}$)cycloalkyl;

wherein each heterocycle is independently a 3 to 8 membered saturated or partially unsaturated monocyclic ring comprising one to four heteroatoms selected from N(R$^x$), O, S, S(O) or S(O)$_2$, or an ortho-fused bicyclic ring of eight to twelve ring atoms derived therefrom, wherein each R$^x$ is independently absent or is H, O, (C$_1$-C$_4$)alkyl, —C(=O)(C$_1$-C$_4$)alkyl, phenyl or benzyl;

each heteroaryl is independently a 5 to 6 membered monocyclic aromatic ring containing one to four heteroatoms each selected from O, S, S(O) or S(O)$_2$, and N(R$^x$) provided the ring does not contain two adjacent O or S atoms, or an ortho-fused bicyclic heterocycle of eight to ten ring atoms derived therefrom; wherein each R$^x$ is independently absent or is H, O, (C$_1$-C$_4$)alkyl, —C(=O)(C$_1$-C$_4$)alkyl, phenyl or benzyl; and each aryl is independently a phenyl ring or an ortho-fused bicyclic carbocycle having nine to ten ring atoms wherein at least one ring is aromatic.

2. The compound of claim 1, having Formula II:

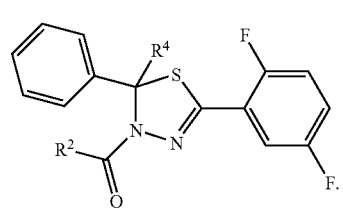

II

3. The compound of claim 1, wherein X is S.

4. The compound of claim 3, wherein R$^1$ is aryl that is optionally substituted with one or more groups independently selected from halo, cyano, difluoromethyl, trifluoromethyl, difluoromethoxy, trifluoromethoxy, —OR$^a$, —NR$^a$R$^b$, —C(=O)R$^a$, —(=O)OR$^a$, —NR$^a$C(=O)OR$^d$, —C(=O)NR$^a$R$^b$, (C$_1$-C$_{10}$)alkyl, (C3-C$_{10}$)cycloalkyl, (C$_2$-C$_{10}$)alkenyl, and (C$_2$-C$_{10}$)alkynyl.

5. The compound of claim 3, wherein R$^1$ is phenyl that is optionally substituted with one or more groups independently selected from halo, cyano, difluoromethyl, trifluoromethyl, difluoromethoxy, trifluoromethoxy, —OR$^a$, —NR$^a$R$^b$, —C(=O)R$^a$, —C(=O)OR$^a$, —NR$^a$C(=O)OR$^d$, —C(=O)NR$^a$R$^b$, (C$_1$-C$_{10}$)alkyl, (C$_3$-C$_{10}$)cycloalkyl, (C$_2$-C$_{10}$)alkenyl, and (C$_2$-C$_{10}$)alkynyl.

6. The compound of claim 3 wherein R$^1$ is phenyl that is optionally substituted with one or more groups independently selected from halo, cyano, difluoromethyl, trifluoromethyl, difluoromethoxy, trifluoromethoxy, —OR$^a$, —NR$^a$R$^b$, —C(=O)OR$^a$, and (C$_1$-C$_{10}$)alkyl.

7. The compound of claim 3, wherein R$^1$ is phenyl that is optionally substituted with one or more halo.

8. The compound of claim 3, wherein R$^1$ is 2,5-difluorophenyl.

9. The compound of claim 3, wherein R$^3$ is phenyl that is optionally substituted with one or more groups independently selected from halo, cyano, nitro, difluoromethyl, trifluoromethyl, difluoromethoxy, trifluoromethoxy, azido, —OR$^a$, —NR$^a$R$^b$, —C(=O)R$^a$, —C(=O)OR$^a$, —NR$^a$C(=O)OR$^d$, —C(=O)NR$^a$R$^b$, (C$_1$-C$_{10}$)alkyl, (C3-C$_{10}$)cycloalkyl, (C$_2$-C$_{10}$)alkenyl, and (C$_2$-C$_{10}$)alkynyl.

10. The compound of claim 3, wherein R$^3$ is phenyl.

11. The compound of claim 3, wherein R$^2$ is (C$_1$-C$_{10}$)alkyl, optionally substituted with one or more R$^o$.

12. The compound of claim 11, wherein each R$^o$ is independently oxo, —NR$^a$R$^b$, —OR$^a$, (C$_3$-C$_{10}$)cycloalkyl, aryl, or —OP(=O)(OR$^a$)$_2$.

13. The compound of claim 3, wherein R$^2$ is 1-methoxyethyl, 1-hydroxyethyl, isopropyl, tert-butyl, ethyl, propyl, 1-methylpropyl, 1-ethylpropyl, 1-hydroxypropyl, 1-hydroxy-2-methylpropyl, 1-hydroxy-2,2-dimethylpropyl, α-hydroxycyclopropylmethyl, α-aminocyclopropylmethyl, α-(N-methylamino)cyclopropylmethyl, 1-ethoxyethyl, 1-trifluoromethoxyethyl, 1-(cyclopropyloxy)ethyl, 1-methoxy-2-methylpropyl, 1-hydroxy-1-methylethyl, 1-methoxy-1-methylethyl, 1-methoxypropyl, 1-methoxy-2,2-dimethylpropyl, 1-(2-methylpropoxy)ethyl, 1-(isopropoxy)ethyl, 1-(tert-butoxy)ethyl, 1-(2-methoxyethoxy)ethyl, 1-(phenoxy)ethyl, 1-(2-pyridyloxy)ethyl, 1-(3-pyridyloxy)ethyl, 1-(benzyloxy)ethyl, α-methoxybenzyl, 2-methoxyethyl, 1-(N-acetylamino)-2-methylpropyl, 1-amino-2-methylpropyl, acetyl, 3-aminopropyl, 2-amino-1,1-dimethylethyl, 1-amino-2-methylpropyl, 1-amino-2,2-dimethylpropyl, 1-methoxycyclopropylmethyl, 1-methoxyethyl, or

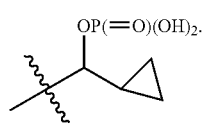

14. The compound of claim 3, wherein R² is NR$^j$R$^k$.

15. The compound of claim 14, wherein R² is N-methoxy-N-methylamino, N-methoxy-N-ethylamino, N-ethoxy-N-methylamino, N-ethoxy-N-ethylamino, N-t-butoxy-N-methylamino, N-isopropoxy-N-ethylamino, N-ethoxy-N-isopropylamino, N-ethoxy-N-t-butylamino N,N-dimethylamino, N-hydroxy-N-methylamino, methylamino, N-(4-piperidyl)-N-methylamino, N-(1-acetylpiperid-4-yl)-N-methylamino, N-(3-aminopropyl)-N-methylamino, N-hydroxymethyl-N-methylamino, N-phosphorylmethyl-N-methylamino, N-hydroxymethyl-N-ethylamino, N-(2-hydroxyethyl)-N-ethylamino, N-(3-hydroxypropyl)-N-ethylamino, N-(4-hydroxybutyl)-N-ethylamino, N-(2-aminoethyl)-N-ethylamino, N-(3-aminopropyl)-N-ethylamino, N-(4-aminobutyl)-N-ethylamino, 1-azetidinyl, 1-pyrrolidinyl, 1-piperidino, or 4-morpholino.

16. The compound of claim 3, wherein R² is (C₃-C₁₀) cycloalkyl, optionally substituted with one or more R°.

17. The compound of claim 16, wherein R² is cyclobutyl, cyclopentyl, 1-methylcyclopropyl, 1-trifluoromethylcyclopropyl, 1-hydroxycyclopropyl, 1-methoxycyclopropyl or 2-fluorocyclohexyl.

18. The compound of claim 3, wherein R² is heterocycle, aryl, or heteroaryl, wherein each R² is optionally substituted with one or more R°.

19. The compound of claim 18, wherein R² is 3-pyridyl, 2-pyridyl, 3-methyl-2-furyl, 2-methyl-5-thiazolyl, 3-aminophenyl, 5-methyl-2-thienyl, or tetrahydrofuranyl.

20. The compound of claim 3, wherein R² is 1-methoxyethyl, 1-hydroxyethyl, or N-methoxy-N-methylamino.

21. The compound of claim 3, wherein —C(=O)R² is (S)-2-methoxypropanoyl or (S)-2-hydroxypropanoyl.

22. The compound of claim 3, wherein R⁴ is Z—NR$^g$—C(=NR$^h$)R$^i$, Z—NR$^g$C(=NR$^h$)NR$^j$R$^k$, Z—NR$^m$—NR$^n$—C(=NR$^h$)R$^i$, Z—NR$^g$—C(=CHR$^q$)NR$^j$R$^k$, or Z—NR$^m$-NR$^n$—C(=NR$^h$)NR$^j$R$^k$.

23. The compound of claim 3, wherein R⁴ is Z—C(=NR$^h$)NR$^j$R$^k$.

24. The compound of claim 3, wherein R⁴ is Z—O—NR$^g$C(=NR$^h$)NR$^j$R$^k$, Z—O—NR$^g$—C(=NR$^h$)R$^i$, Z—O—NR$^j$R$^k$, Z—O—Z—C(=NR$^h$)NR$^j$R$^k$, or Z—O—N=C(R$^r$)₂.

25. The compound of claim 3, wherein R⁴ is selected from the following structures:

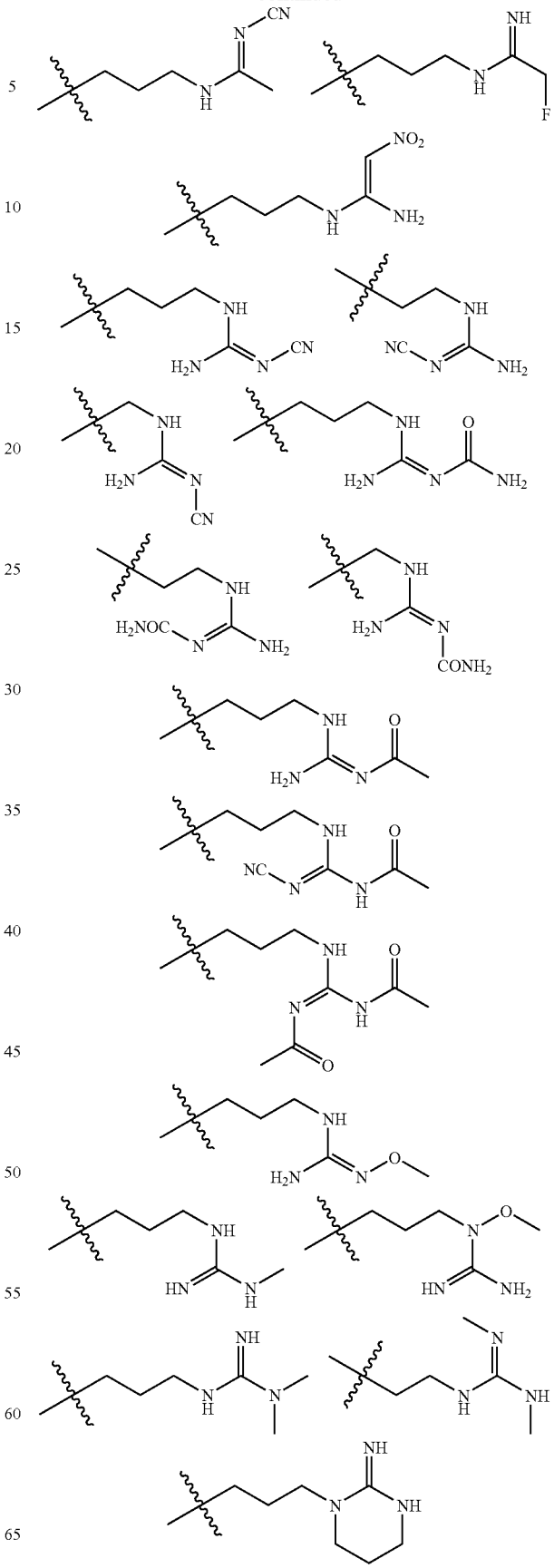

125
-continued
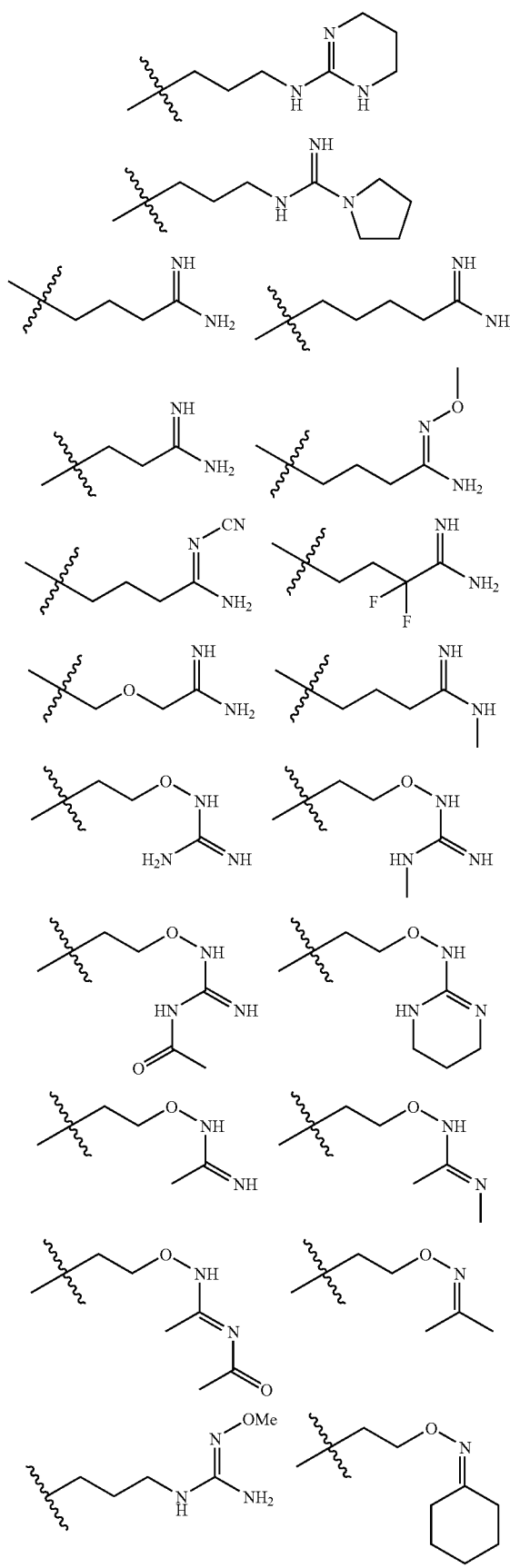
126
-continued
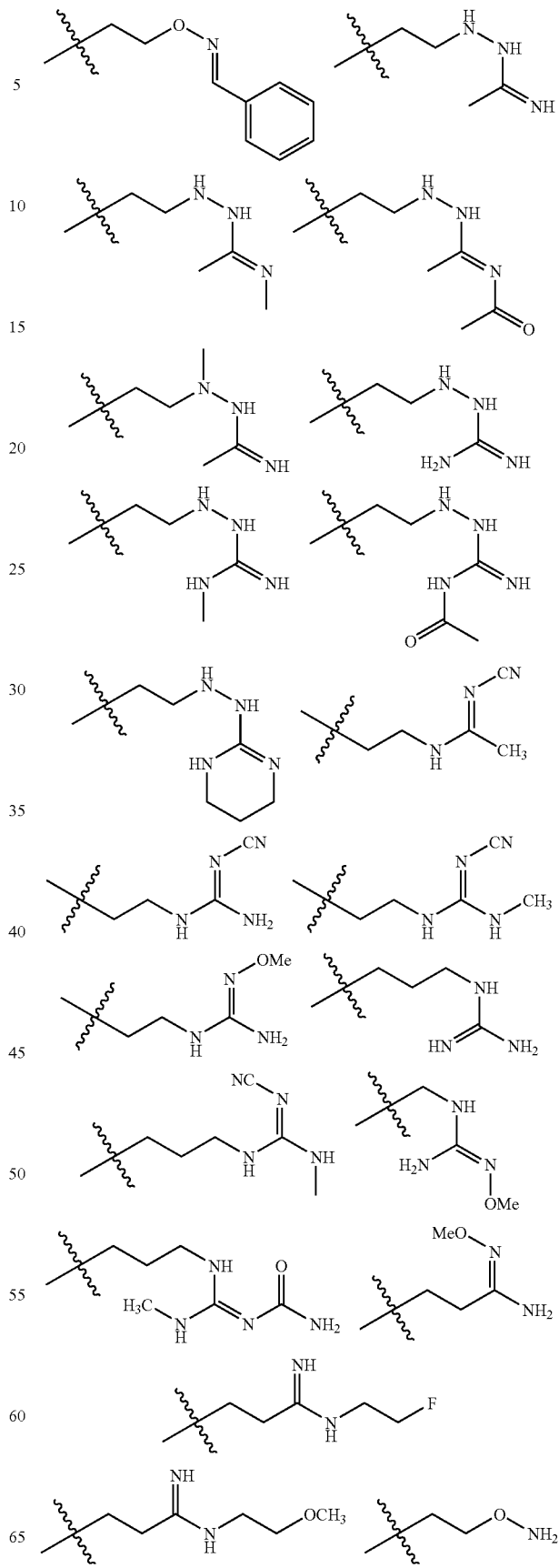

-continued

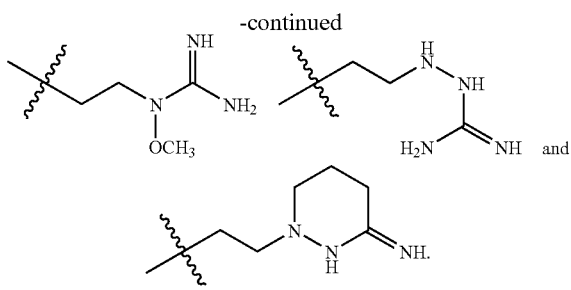

26. The compound of claim 3, wherein $R^4$ has the following structure:

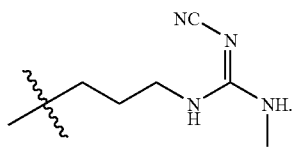

27. The compound of claim 3, wherein Z is $(C_1$-$C_{10})$alkylene, optionally substituted with one or more halogen.

28. The compound of claim 27, wherein Z is ethylene, propylene, methylene, or —$CH_2CH_2CF_2$—.

29. A composition comprising a compound of claim 1 and a pharmaceutically acceptable carrier.

30. A method for inhibiting one or more kinesins, comprising contacting the one or more kinesins with an effective amount of a compound as described in claim 1 to the animal.

31. A method for inhibiting one or more kinesins in an animal, comprising administering an effective amount of a compound as described in claim 1 to the animal.

32. A kit for treating an abnormal cell growth condition, wherein said kit comprises:
    a) a compound as described in claim 1; and
    b) instructions for use.

33. A compound as described in claim 1 for use in therapy.

34. A method for preparing a compound of Formula I or a salt thereof comprising:
    a) deprotecting a corresponding compound that comprises one or more protecting groups;
    b) for a salt of a compound of Formula I, forming a salt from a corresponding compound of Formula I;
    c) for a compound of Formula I, wherein $R^4$ is Z—C(=NH)$NR^jR^k$, by reacting a corresponding compound wherein $R^4$ is Z—C(=NH)$OR_d$, wherein $R_d$ is $(C_1$-$C_{10})$ alkyl with a corresponding amine $HNR^jR^k$;
    d) for a compound of Formula I, wherein $R^4$ is Z—C(=NCN)$NR^jR^k$, reacting a corresponding compound wherein $R^4$ is Z—C(=NH)$OR_d$, wherein $R_d$ is $(C_1$-$C_{10})$ alkyl with cyanamide followed by treatment with a corresponding amine $HNR^jR^k$;
    e) for a compound of Formula I, wherein $R^4$ is Z—C(=$NOR^p$)$NH_2$, reacting a corresponding compound wherein $R^4$ is Z—C(=NH)$OR_d$, wherein $R_d$ is $(C_1$-$C_{10})$ alkyl with a corresponding amine $NH_2(OR^p)$;
    f) for a compound of Formula I, wherein $R^4$ is Z—$NR^g$—C(=$NR^h$)$NR^jR^k$, reacting a corresponding compound wherein $R^4$ is Z—$NHR^g$ with a guanidinylating reagent;
    g) for a compound of Formula I, wherein $R^4$ is Z—$NR^g$—C(=$NR^h$)$NR^jR^k$, reacting a corresponding compound wherein $R^4$ is Z—$NHR^g$ with an N-protected guanidinylating reagent, followed by deprotection;
    h) for a compound of Formula I, wherein $R^4$ is Z—$NR^g$—C(=$NR^h$)$R^i$, reacting a corresponding compound wherein $R^4$ is Z—$NHR^g$ with a corresponding imidate or imidate salt;
    i) for a compound of Formula I, wherein $R^4$ is Z—$NR^g$—C(=NCN)$R^i$, reacting a corresponding compound wherein $R^4$ is Z—$NHR^g$ with a corresponding cyanoimidate or cyanoimidate salt;
    j) for a compound of Formula I, wherein $R^4$ is Z—$NR^g$—C(=NH)$NR^j(OR^p)$, treating a corresponding compound wherein $R^4$ is Z—$NR^g$—CN with a corresponding alkoxyamine or alkoxyamine salt;
    k) for a compound of Formula I, wherein $R^4$ is Z—$NR^g$—C(=$NR^h$)$NR^jR^k$, wherein $R^h$ is aminocarbonyl, treating a corresponding compound wherein $R^h$ is cyano with acid in an aqueous solvent;
    l) for a compound of Formula I, wherein $R^4$ is Z—O—$NR^g$—C(=$NR^h$)$R^i$, treating a corresponding compound wherein $R^4$ is Z—O—$NHR^g$ with a corresponding imidate or imidate salt;
    m) for a compound of Formula I, wherein $R^4$ is Z—O—$NR^g$C(=$NR^h$)$NR^jR^k$, treating a corresponding compound wherein $R^4$ is Z—O—$NHR^g$ with a corresponding guanidinylating reagent;
    n) for a compound of Formula I, wherein $R^4$ is Z—O—$NR^g$C(=$NR^h$)$NR^jR^k$, treating a corresponding compound wherein $R^4$ is Z—O—$NHR^g$ with an N-protected guanidinylating reagent, followed by deprotection;
    o) for a compound of Formula I, wherein $R^4$ is Z—N($OR^p$)C(=$NR^h$)$R^i$, treating a corresponding compound wherein $R^4$ is Z—NH($OR^p$) with a corresponding imidate or imidate salt;
    p) for a compound of Formula I, wherein $R^4$ is Z—N($OR^p$)C(=$NR^h$)$NR^jR^k$, treating a corresponding compound wherein $R^4$ is Z—NH($OR^p$) with a corresponding guanidinylating reagent;
    q) for a compound of Formula I, wherein $R^4$ is Z—N($OR^p$)C(=$NR^h$)$NR^jR^k$, treating a corresponding compound wherein $R^4$ is Z—NH($OR^p$) with a corresponding N-protected guanidinylating reagent, followed by deprotection;
    r) for a compound of Formula I, wherein $R^4$ is Z—$NR^m$—$NR^n$—C(=$NR^h$)$R^i$, treating a corresponding compound wherein $R^4$ is Z—$NR^m$—$NR^n$—H with a corresponding imidate or imidate salt;
    s) for a compound of Formula I, wherein $R^4$ is Z—$NR^m$—$NR^n$—C(=$NR^h$)$NR^jR^k$, treating a corresponding compound wherein $R^4$ is Z—$NR^m$—$NR^n$—H with a corresponding guanidinylating reagent; or
    t) for a compound of Formula I, wherein $R^4$ is Z—$NR^m$—$NR^n$—C(=$NR^h$)$NR^jR^k$, treating a corresponding compound wherein $R^4$ is Z—$NR^m$—$NR^n$—H with a corresponding N-protected guanidinylating reagent, followed by deprotection.

35. A compound of Formula I as defined in claim 1 and having the structure:

131
-continued
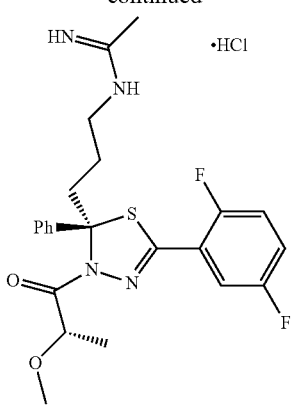
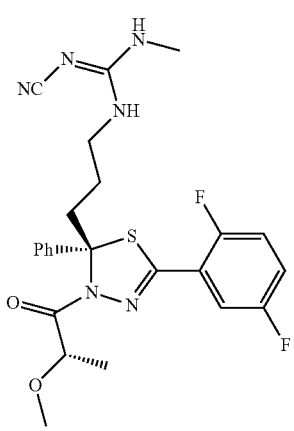
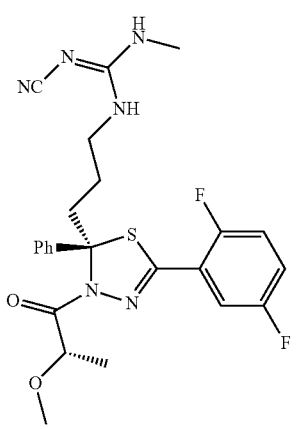
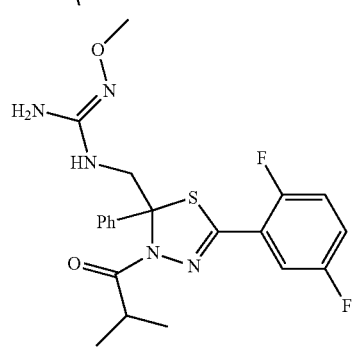
132
-continued
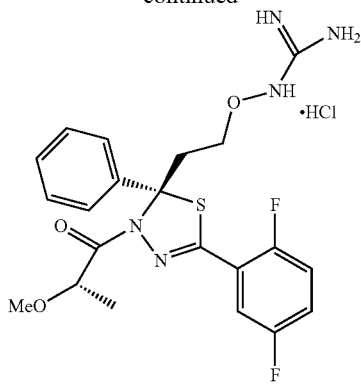
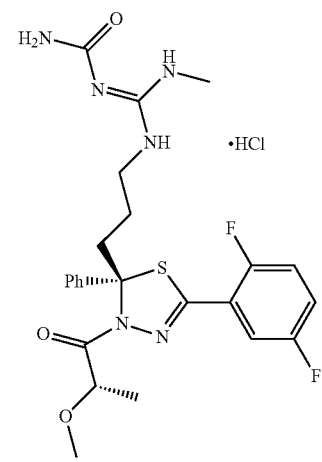
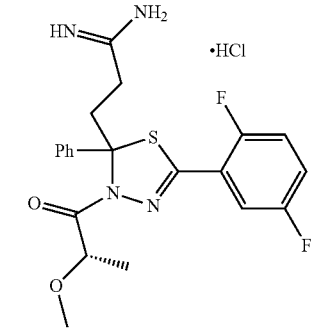
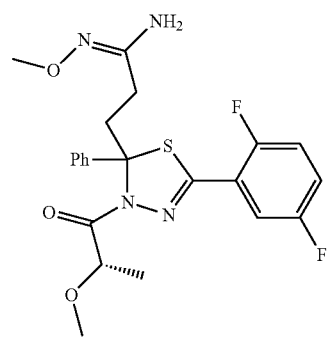

133
-continued
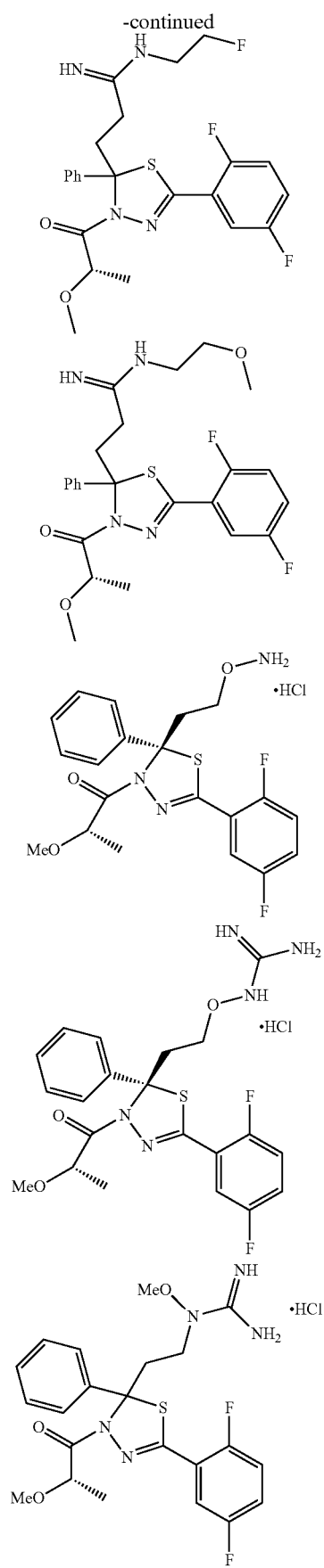
134
-continued
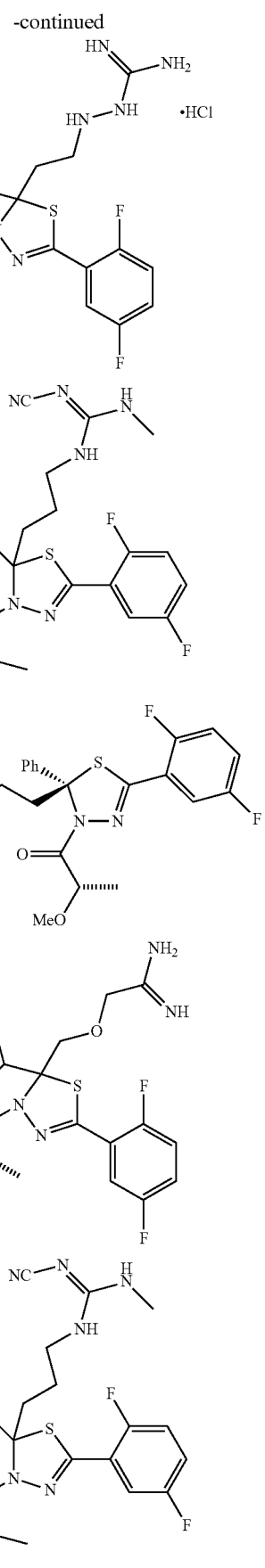

-continued
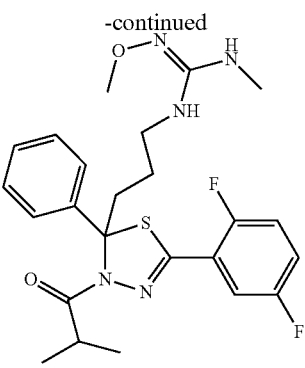
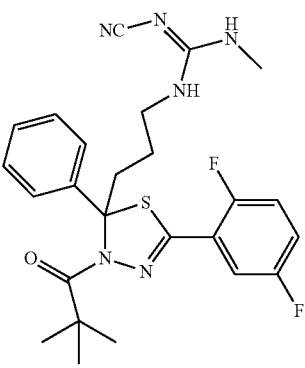
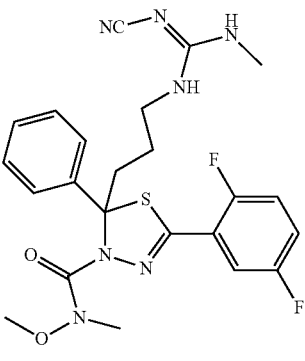
-continued
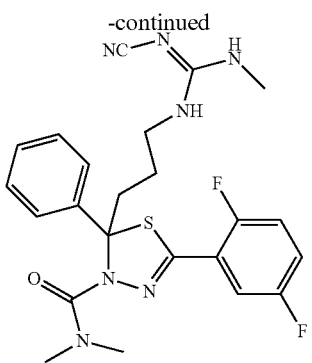
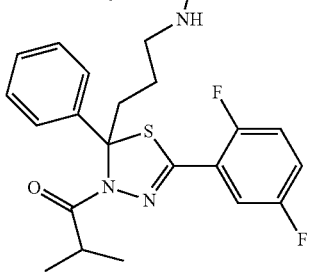
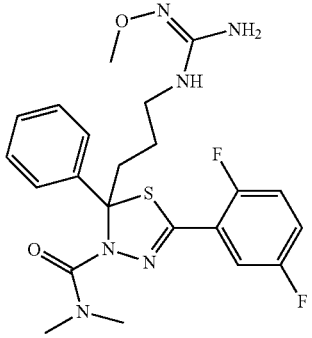
or a pharmaceutically acceptable salt thereof.
36. A composition comprising a compound of claim 35 and a pharmaceutically acceptable carrier.
37. A method for inhibiting one or more kinesins in an animal, comprising administering an effective amount of a compound as described in claim 35 to the animal.
* * * * *